US009181306B2

(12) United States Patent
Berkower et al.

(10) Patent No.: US 9,181,306 B2
(45) Date of Patent: Nov. 10, 2015

(54) INSERTION OF FOREIGN GENES IN RUBELLA VIRUS AND THEIR STABLE EXPRESSION IN A LIVE, ATTENUATED VIRAL VACCINE

(75) Inventors: Ira Berkower, Washington, DC (US); Angelo Spadaccini, Carine (AU)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 276 days.

(21) Appl. No.: 13/501,893

(22) PCT Filed: Oct. 15, 2010

(86) PCT No.: PCT/US2010/052948
§ 371 (c)(1),
(2), (4) Date: Apr. 13, 2012

(87) PCT Pub. No.: WO2011/047340
PCT Pub. Date: Apr. 21, 2011

(65) Prior Publication Data
US 2012/0207784 A1    Aug. 16, 2012

Related U.S. Application Data

(60) Provisional application No. 61/252,568, filed on Oct. 16, 2009.

(51) Int. Cl.
| C07K 14/005 | (2006.01) |
| A61K 39/21 | (2006.01) |
| C12N 7/00 | (2006.01) |
| C12N 15/86 | (2006.01) |
| A61K 39/12 | (2006.01) |
| A61K 39/00 | (2006.01) |

(52) U.S. Cl.
CPC .............. *C07K 14/005* (2013.01); *A61K 39/12* (2013.01); *A61K 39/21* (2013.01); *C12N 7/00* (2013.01); *C12N 15/86* (2013.01); *A61K 2039/5254* (2013.01); *A61K 2039/5256* (2013.01); *A61K 2039/5258* (2013.01); *A61K 2039/545* (2013.01); *C12N 2740/15022* (2013.01); *C12N 2740/16034* (2013.01); *C12N 2740/16122* (2013.01); *C12N 2770/36223* (2013.01); *C12N 2770/36243* (2013.01)

(58) Field of Classification Search
None
See application file for complete search history.

(56) References Cited

U.S. PATENT DOCUMENTS 6,958,237 B2 * 10/2005 Frey et al. ................... 435/320.1
7,211,659 B2 *  5/2007 zur Megede ............... 536/23.72
2003/0130498 A1  7/2003 Frey et al.

FOREIGN PATENT DOCUMENTS

WO    WO 2006010106    *  1/2006

OTHER PUBLICATIONS

Zhou et al. Analysis of base and codon usage by rubella virus. Archives of Virology, 2012, vol. 157, p. 889-899.*
Finberg et al. Toll like receptors and viruses. Reviews in Medical Virology, 2007, vol. 17, p. 35-43.*
Potter et al. Obstacles to successful antiretroviral treatment of HIV-1 infection: problems & perspectives. Indian Journal of Medical Research, 2004, vol. 119, p. 217-237.*
UniProtKB/Swiss-Prot: Q8Q413. submitted by Kunstman et al. 2002.*
Matthews et al., "Determinants of subcellular localization of the rubella virus nonstructural replicase proteins," *Virology*, vol. 390, No. 2, pp. 315-323, Aug. 1, 2009.
Pugachev et al., "Development of a Rubella Virus Vaccine Expression Vector: Use of a Picornavirus Internal Ribosome Entry Site Increases Stability of Expression," *Journal of Virology*, vol. 74, No. 22, pp. 10811-10815, Nov. 2000.
Pugachev et al., "Improvement of the Specific Infectivity of the Rubella Virus (RUB) Infectious Clone: Determinants of Cytopathogenicity Induced by Rub Map to the Nonstructural Proteins," *Journal of Virology*, vol. 71, No. 1, pp. 562-568, Jan. 1997.
Spadaccini et al., "Stable expression of a foreign protein by a replication-competent rubella viral vector," *Vaccine*, vol. 28, No. 5, pp. 1181-1187, Feb. 3, 2010.
Tzeng, et al., "Complementation of a Deletion in the Rubella Virus P150 Nonstructural Protein by the Viral Capsid Protein," *Journal of Virology*, vol. 77, No. 17, pp. 9502-9510, Sep. 2003.
Tzeng et al., "Functional Replacement of a Domain in the Rubella Virus P150 Replicase Protein by the Virus Capsid Protein," *Journal of Virology*, vol. 83, No. 8, pp. 3549-3555, Apr. 2009.

* cited by examiner

*Primary Examiner* — Michelle S Horning
(74) *Attorney, Agent, or Firm* — Klarquist Sparkman, LLP

(57) ABSTRACT

Disclosed herein are isolated rubella viral vector constructs that include a rubella non-structural protein open reading frame (ORF) with an in-frame deletion, a rubella structural protein ORF, and a heterologous antigenic insert. In one example, the in-frame deletion within the rubella non-structural protein ORF is an in-frame deletion between two NotI restriction enzyme sites. In some examples, the heterologous antigenic insert is positioned within the rubella non-structural protein ORF. In other examples, the heterologous antigenic insert is positioned within the rubella structural protein ORF. Exemplary antigenic inserts include a Gag antigenic insert, a gp41 antigenic insert or a gp120 antigenic insert. Also disclosed are uses of the isolated rubella viral vector, such as to induce an immune response to HIV-1, testing sensitivity to neutralizing antibodies, or screening antiviral drugs (such as protease inhibitors).

4 Claims, 8 Drawing Sheets

INSERTION OF FOREIGN GENES IN RUBELLA VIRUS AND THEIR STABLE EXPRESSION IN A LIVE, ATTENUATED VIRAL VACCINE

CROSS REFERENCE TO RELATED APPLICATION

This is the U.S. National Stage of International Application No. PCT/US2010/052948, filed Oct. 15, 2010, which was published in English under PCT Article 21(2), which in turn claims the benefit of U.S. Provisional Application No. 61/252,568, filed Oct. 16, 2009, which is which is incorporated herein by reference in its entirety.

FIELD

This disclosure relates to the field of viral vectors, specifically to a rubella viral vector platform capable of expressing a heterologous antigen, and the use of this platform to induce an immune response.

BACKGROUND

Acquired immune deficiency syndrome (AIDS) is recognized as one of the greatest health threats facing modern society. Treatments for HIV-infected individuals as well as the development of vaccines to protect against infection are urgently needed. One difficulty has been in eliciting neutralizing antibodies to the virus.

The HIV-1 envelope glycoproteins (gp120-gp41), which mediate receptor binding and entry, are the major targets for neutralizing antibodies. Although the envelope glycoproteins are immunogenic and induce a variety of antibodies, the neutralizing antibodies that are induced are strain-specific, and the majority of the immune response is diverted to non-neutralizing determinants. Broadly neutralizing monoclonal antibodies have been isolated only rarely from natural HIV infection. For example, only three gp41-directed neutralizing antibodies (2F5, 4E10 and Z13) and a few gp120-directed neutralizing antibodies have been identified to date.

The HIV envelope spike mediates binding to receptors and virus entry. The spike is trimeric and composed of three gp120 exterior and three gp41 transmembrane envelope glycoproteins. CD4 binding to gp120 in the spike induces conformational changes that allow binding to a coreceptor, either CCR5 or CXCR4, which is required for viral entry.

The mature gp120 glycoprotein is approximately 470-490 amino acids long depending on the HIV strain of origin. N-linked glycosylation at approximately 20 to 25 sites makes up nearly half of the mass of the molecule. Sequence analysis shows that the polypeptide is composed of five conserved regions (C1-C5) and five regions of high variability (V1-V5).

With the number of individuals infected with HIV-I approaching 1% of the world's population, an effective vaccine is urgently needed. As an enveloped virus, HIV-I hides most of its proteins and genes from humoral recognition behind a protective lipid bilayer. An available exposed viral target for neutralizing antibodies is the envelope spike. Genetic, immunologic and structural studies of the HIV-I envelope glycoproteins have revealed extraordinary diversity as well as multiple overlapping mechanisms of humoral evasion, including self-masquerading glycan, immunodominant variable loops, and conformational masking. These evolutionarily-honed barriers of antigenic diversity and immune evasion have confounded traditional means of vaccine development. The need exists for immunogens that are capable of eliciting a protective immune response in a suitable subject. In order to be effective, the antibodies raised must be capable of neutralizing a broad range of HIV strains and subtypes.

Some of our most successful vaccines, such as oral polio virus and measles, mumps, and rubella virus vaccine, consist of live attenuated viruses. These are given at very low doses, so the vaccine strain must grow in the host to produce sufficient viral antigens to elicit an immune response. By simulating a viral infection, they can elicit innate and adaptive immune responses, resulting in antigen-specific T cells and antibody-producing B cells. Through a process of attenuation, the vaccine strains have retained the growth and immunogenicity of wild type virus while losing its pathogenicity and virulence. However, for many pathogenic viruses, such as HIV, it has not been possible to produce a live attenuated vaccine.

SUMMARY

Historically, viral vaccines have been live-attenuated or chemically inactivated forms of the virus. However, this approach has limited utility when used for certain pathogenic viruses, including HIV. Thus additional approaches for creating vaccines are needed. Disclosed herein is a rubella vector platform capable of expressing a heterologous antigen, such as an HIV antigen (for example, an envelope glycoprotein antigen, such as, a gp41 or a gp120), a Gag antigen (such as an HIV or SIV Gag antigen), or hepatitis B surface antigen (HBsAg), and the use of this platform to induce an immune response.

In some embodiments, an isolated rubella viral vector includes a rubella non-structural protein open reading frame (ORF) with an in-frame deletion, a rubella structural protein ORF, and a heterologous antigenic insert. In some example, the in-frame deletion within the rubella non-structural protein ORF is an in-frame deletion between two NotI restriction enzyme sites. In some examples, the heterologous antigenic insert is positioned within the rubella non-structural protein ORF. In other examples, the heterologous antigenic insert is positioned within the rubella structural protein ORF.

Exemplary antigenic inserts can include cytotoxic T lymphocyte (CTL) epitopes, HIV envelope protein epitopes and HBsAg inserts. For example, an antigenic insert can include a CTL epitope of HIV or SIV Gag, an epitope of HIV gp41, or an epitope of HIV gp120. The antigenic insert can include repeats of any one of the disclosed antigenic epitopes, such as one to ten copies of one or more of the disclosed antigenic envelope or CTL epitopes.

In some examples, an antigenic insert is a wildtype or variant of a CTL epitope of a Gag polypeptide or a fragment thereof. In some examples, the antigenic peptide includes one or more major CTL epitopes of Gag, and can be from about 8 to about 300 amino acids in length, such from about 10 to about 280 amino acids in length, such as 20 to about 270 amino acids in length, such as from about 40 to about 250 amino acids in length, including 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 57, 60, 63, 65, 67, 70, 73, 75, 77, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300. In some examples, an antigenic insert includes one or more CTL epitopes, such as one or more CTL HIV or SIV epitopes, including those set forth as SEQ ID NOs: 92-102. In some examples, an antigenic insert includes one or more antigenic polypeptide fragments of Gag, such as one o more antigenic polypeptides with an amino acid sequence provided by SEQ ID NOs: 82-88, 90 or 91.

In some examples, an antigenic insert is a wildtype or variant gp41 polypeptide or a fragment thereof. In some examples, a gp41 antigenic insert can include (a) an antigenic polypeptide fragment of gp41 and (b) a transmembrane spanning region of gp41. For example, the gp41 antigenic insert includes (a) an antigenic polypeptide fragment, such as an antigenic polypeptide fragment with the amino acid sequence set forth in SEQ ID NO:1 (in which wherein $X_1$, $X_2$ and $X_3$ are any amino acid) and the polypeptide is between 10 and 200 amino acids in length, such as from about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, or 145 amino acids; and (b) a transmembrane spanning gp41 region, such as a transmembrane spanning gp41 region with the amino acid sequence set forth in SEQ ID NO: 25 (in which $X_4$, $X_5$, and $X_6$ are any hydrophobic amino acid) and is between 22 and 40 amino acids in length, such as about 23 and 38 amino acids in length, including 24, 25, 26, 27, 28, 29, 30, 31, 32, 33, 34, 35, 36, 37, 38 amino acids. In certain examples, an antigenic insert includes an antigenic polypeptide fragment of gp41 with an amino acid sequence provided by SEQ ID NOs: 1-22, 30, 81 or 89 and a transmembrane region of gp41 with an amino acid sequence provided by SEQ ID NOs: 25-28.

In some examples, an antigenic insert is a wildtype or variant gp120 polypeptide. In an example, a wildtype gp120 polypeptide has an amino acid provided by SEQ ID NO: 63 or a fragment thereof. In other examples, a variant gp120 polypeptide includes a gp120 polypeptide in which at least 8 consecutive residues of the fourth conserved loop (C4) between residues 419 and 434 of gp120 according HXB2 numbering of SEQ ID NO: 63 are deleted. This deletion within the β20-21 loop of the gp120 polypeptide exposes the CD4 binding site thereby providing improved antibody binding and antibody induction. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 63 have been deleted.

In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63). In other embodiments, variant gp120 polypeptides include combinations of the amino and carboxyl ends between residues 419 and 434.

In some embodiments, a variant gp120 polypeptide does not include a variant in which residues 419-428 of SEQ ID NO: 63 are deleted. In other embodiments, a variant gp120 polypeptide does not include a variant in which residues 437-452 of SEQ ID NO: 63 are deleted. In certain examples, an antigenic insert includes an amino acid sequence set forth by SEQ ID NOs: 63, 66, 67, 69, 71, 73 or 74.

Viral-like particles including the isolated viral vector construct are provided herein. Compositions comprising the viral-like particles are also provided.

The disclosed isolated viral vectors can be used to induce an immune response, such as a protective immune response, when introduced into a subject. The provided rubella viral vector platforms can also be used in assays to diagnose an HIV infection. Thus, methods are provided for inhibiting HIV infection in a subject, for inducing an immune response to HIV in a subject, and for diagnosing HIV infection in a subject. The disclosed viral vector platforms can also be use for measuring host range, testing sensitivity to neutralizing antibodies, or screening antiviral drugs. In one example, methods of screening antiviral drugs including methods of identifying protease inhibitors are disclosed.

The foregoing and other features of the disclosure will become more apparent from the following detailed description, which proceeds with reference to the accompanying figures and sequence listing.

BRIEF DESCRIPTION OF SEQUENCES

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. All sequence database accession numbers referenced herein are understood to refer to the version of the sequence identified by that accession number as it was available on the designated date. In the accompanying sequence listing:

SEQ ID NO: 1 is a consensus amino acid sequence for the membrane proximal region (MPR) of gp41 of HIV-1. An X represents specific amino acids where alterations can be tolerated.

SEQ ID NO: 2 is a consensus amino acid sequence based on each clade consensus sequence of the MPR region from HIV-1.

SEQ ID NO: 3 is the ancestral amino acid sequence of the MPR region from HIV-1 clade M. This sequence is also the consensus amino acid sequence of the MPR region from HIV-1 clade AG.

SEQ ID NO: 4 is the consensus amino acid sequence of the MPR region from HIV-1 clade A1. This sequence is also the ancestral amino acid sequence of the MPR region from HIV-1 clade A1.

SEQ ID NO: 5 is the consensus amino acid sequence of the MPR region from HIV-1 clade A2.

SEQ ID NO: 6 is the consensus amino acid sequence of the MPR region from HIV-1 clade B. This sequence is also the ancestral amino acid sequence of the MPR region from HIV-1 clade B.

SEQ ID NO: 7 is the consensus amino acid sequence of the MPR region from HIV-1 clade C.

SEQ ID NO: 8 is the ancestral amino acid sequence of the MPR region from HIV-1 clade C.

SEQ ID NO: 9 is the consensus amino acid sequence of the MPR region from HIV-1 clade D.

SEQ ID NO: 10 is the consensus amino acid sequence of the MPR region from HIV-1 clade F1.

SEQ ID NO: 11 is the consensus amino acid sequence of the MPR region from HIV-1 clade F2.

SEQ ID NO: 12 is the consensus amino acid sequence of the MPR region from HIV-1 clade G.

SEQ ID NO: 13 is the consensus amino acid sequence of the MPR region from HIV-1 clade H.

SEQ ID NO: 14 is the consensus amino acid sequence of the MPR region from HIV-1 clade AE.

SEQ ID NO: 15 is the consensus amino acid sequence of the MPR region from HIV-1 clade AB.

SEQ ID NO: 16 is the consensus amino acid sequence of the MPR region from HIV-1 clade 04CPX.

SEQ ID NO: 17 is the consensus amino acid sequence of the MPR region from HIV-1 clade 06CPX.

SEQ ID NO: 18 is the consensus amino acid sequence of the MPR region from HIV-1 clade 08BC.

SEQ ID NO: 19 is the consensus amino acid sequence of the MPR region from HIV-1 clade 10CD.

SEQ ID NO: 20 is the consensus amino acid sequence of the MPR region from HIV-1 clade 11CPX.

SEQ ID NO: 21 is the consensus amino acid sequence of the MPR region from HIV-1 clade 12BF.

SEQ ID NO: 22 is the consensus amino acid sequence of the MPR region from HIV-1 clade 14BG.

SEQ ID NOs: 23-24 are oligonucleotide primers used to amplify a rubella sequence flanking a zGFP insert.

SEQ ID NO: 25 is a consensus amino acid sequence for the transmembrane region of gp41. An X represents any hydrophobic amino acid.

SEQ ID NOs: 26-28 are amino acid sequences for a transmembrane spanning region of gp41.

SEQ ID NO: 29 is an amino acid sequence for a disclosed isolated immunogen in which the first transmembrane domain of hepatitis B surface antigen is replaced with the MPR and transmembrane domain of gp41.

SEQ ID NO: 30 is an exemplary MPR region from HIV-1 amino acid sequence.

SEQ ID NO: 31 is an exemplary wildtype amino acid sequence of HBsAg.

SEQ ID NO: 32 is an example of a nucleotide sequence for a T helper cell epitope.

SEQ ID NO: 33 is an example of an amino acid sequence for a T helper cell epitope.

SEQ ID NO: 34 is the CAAX amino acid sequence, where C is cystein, A is an aliphatic amino acid and X is any amino acid.

SEQ ID NO: 35 is the core amino acid sequence of the 2F5 epitope.

SEQ ID NO: 36 is the core amino acid sequence of the 4E10 epitope.

SEQ ID NO: 37 is the linker sequence GPGP.

SEQ ID NO: 38 is a forward primer for amplification of the HBsAg.

SEQ ID NO: 39 is a reverse primer for amplification of the HBsAg.

SEQ ID NO: 40 is a forward primer for amplification of MPR.

SEQ ID NO: 41 is a reverse primer for amplification of MPR.

SEQ ID NO: 42 is a reverse primer for amplification of MPR-Foldon.

SEQ ID NO: 43 is a forward primer for amplification of C-heptad.

SEQ ID NO: 44 is a reverse primer for amplification of MPR-Tm5.

SEQ ID NO: 45 is a reverse primer for amplification of MPR-Tm10.

SEQ ID NO: 46 is a reverse primer for amplification of MPR-Tm15.

SEQ ID NO: 47 is a reverse primer for amplification of MPR-Tm23.

SEQ ID NO: 48 is a forward primer for amplification of the MPR region with AgeI.

SEQ ID NO: 49 is a reverse primer for amplification of the MPR region with AgeI.

SEQ ID NO: 50 is a forward primer for amplification of the MPR region with AgeI.

SEQ ID NO: 51 is a reverse primer for amplification of the MPR region with AgeI.

SEQ ID NO: 52 is a forward primer for amplification of the MPR region with HBsAg (MPRSAG or MPR-N-term).

SEQ ID NO: 53 is a reverse primer for amplification of the MPR region with HBsAg (MPRSAG or MPR-N-term).

SEQ ID NO: 54 is a forward primer for amplification of SAGMPR-R1 (HBsAg at the N-terminus of MPR).

SEQ ID NO: 55 is a reverse primer for amplification of SAGMPR-R1 (HBsAg at the N-terminus of MPR).

SEQ ID NO: 56 is an nucleic acid sequence which encodes the Gag antigenic insert with an amino acid sequence set forth as SEQ ID NO: 103

SEQ ID NO: 57 is an amino acid sequence for a disclosed isolated immunogen in which the first and third transmembrane domains of hepatitis B surface antigen are each replaced with the MPR and transmembrane domain of gp41.

SEQ ID NO: 58 is a nucleic acid sequence for a disclosed isolated immunogen in which the third transmembrane domains of HBsAg is replaced with the MPR and transmembrane domain of gp41.

SEQ ID NO: 59 is an amino acid sequence for a disclosed isolated immunogen in which the third transmembrane domain of hepatitis B surface antigen is replaced with the MPR and transmembrane domain of gp41.

SEQ ID NO: 60 is an amino acid sequence of the MPR region in the TM32 or TM32F constructs.

SEQ ID NO: 61 is an amino acid sequence of the MPR region in the TM34 construct.

SEQ ID NO: 62 is an amino acid sequence of a disclosed variant HbsAg construct (TM16+34) in which the first domain is replaced with a MPR and transmembrane domain of gp41 and an additional MPR is inserted between a second and third domain in the variant HBsAg.

SEQ ID NO: 63 is an amino acid sequence of a variant gp120 with a V1V2 deleted gp120.

SEQ ID NO: 64 is an amino acid sequence of a disclosed variant HbsAg construct (TM16+32F) in which the first domain is replaced with a MPR and transmembrane domain of gp41 and four additional MPRs are inserted between a second and third domain in the variant HBsAg.

SEQ ID NO: 65 is an amino acid sequence of a disclosed variant HbsAg construct (32F) in which four MPRs are inserted between a second and third domain in the variant HBsAg.

SEQ ID NO: 66 is an amino acid sequence for a variant gp120 with a V1V2 deletion with a beta 20-21 loop deletion.

SEQ ID NO: 67 is an amino acid sequence for a variant gp120 from HIV isolate JR-FL.

SEQ ID NO: 68 is a nucleic acid sequence for a variant gp120 from HIV isolate JR-FL.

SEQ ID NO: 69 is an amino acid sequence for a variant gp120 from HIV isolate AD8.

SEQ ID NO: 70 is a nucleic acid sequence for a variant gp120 from HIV isolate AD8.

SEQ ID NO: 71 is an amino acid sequence for a variant gp120 from HIV isolate BaL.

SEQ ID NO: 72 is a nucleic acid sequence for a variant gp120 from HIV isolate BaL.

SEQ ID NO: 73 is an amino acid sequence for a variant gp120 from HIV isolate IIIB.

SEQ ID NO: 74 is a nucleic acid sequence for a variant gp120 from HIV isolate IIB.

SEQ ID NOS: 75-76 are oligonucleotide primers used to amplify Zoanthus sp. green fluorescent protein (zGFP).

SEQ ID NOS: 77-80 are amino acid sequences of disclosed variant rubella constructs in which one MPR is inserted into the structural open reading frame of the rubella construct.

SEQ ID NO: 81 is an amino acid sequence of $MPR_f$ which contains the epitope recognized by neutralizing monoclonal antibody 2F5.

SEQ ID NOS: 82-88 are amino acid sequences of Gag antigenic inserts.

SEQ ID NO: 89 is an amino acid sequence of $MPR_e$ which contains the epitope recognized by neutralizing monoclonal antibody 4E1.

SEQ ID NOs: 90-91 are amino acid sequences of Gag antigenic inserts.

SEQ ID NOs: 92-96 are amino acid sequences of CTL epitopes of SIV Gag.

SEQ ID NOs: 97-102 are amino acid sequences of CTL epitopes of HIV Gag.

SEQ ID NO: 103 is an amino acid sequence of a Gag antigenic insert.

The Sequence Listing is submitted as an ASCII text file in the form of the file named Sequence.txt, which was created on Oct. 15, 2010, and is 118,557 bytes, which is incorporated by reference herein.

DETAILED DESCRIPTION

I. Abbreviations and Terms

Figure 1A:
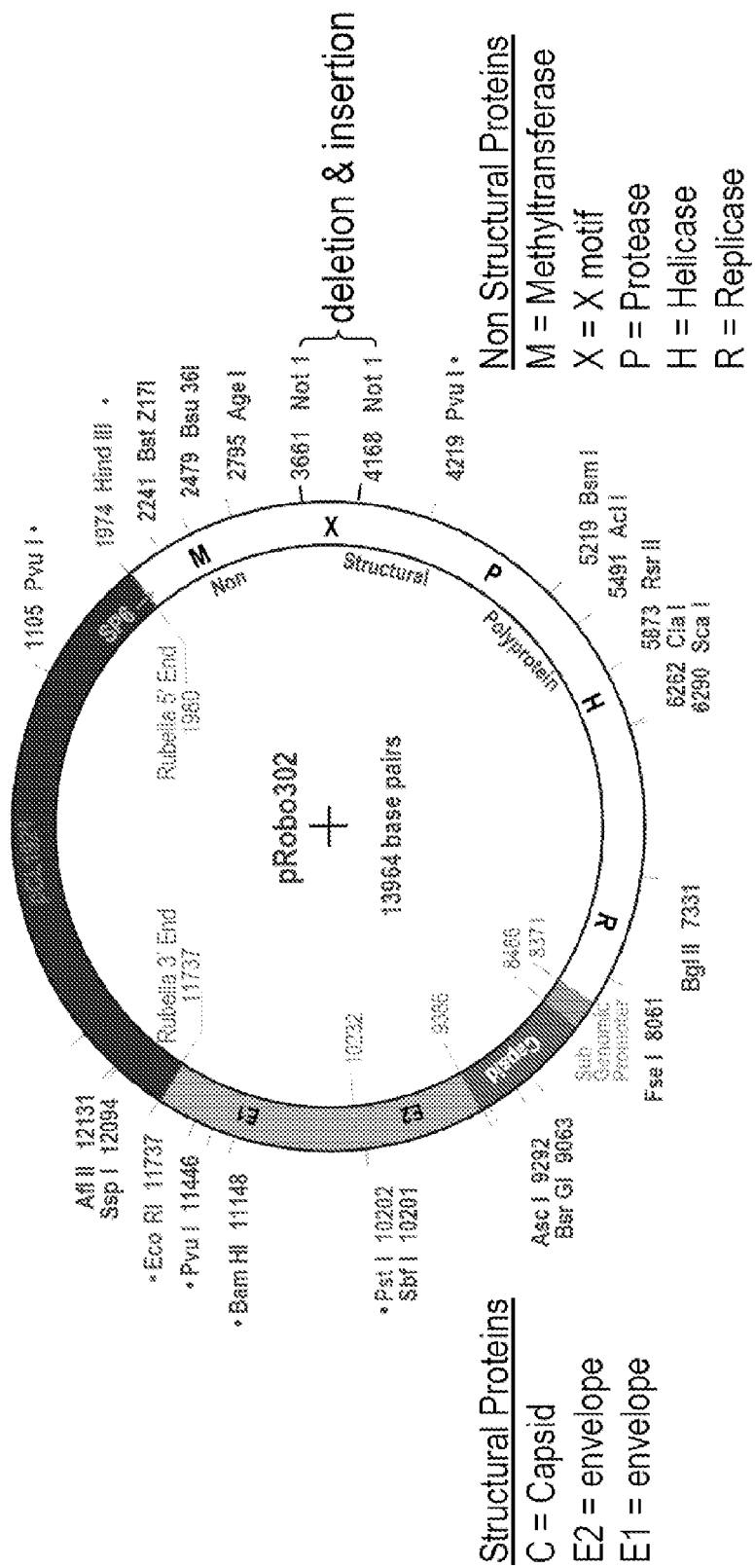
FIG. 1A is a restriction map of a rubella cDNA plasmid in which the two Not I sites are shown and the deletion between such sites becomes the site of zGFP insertion.
Figure 1B:
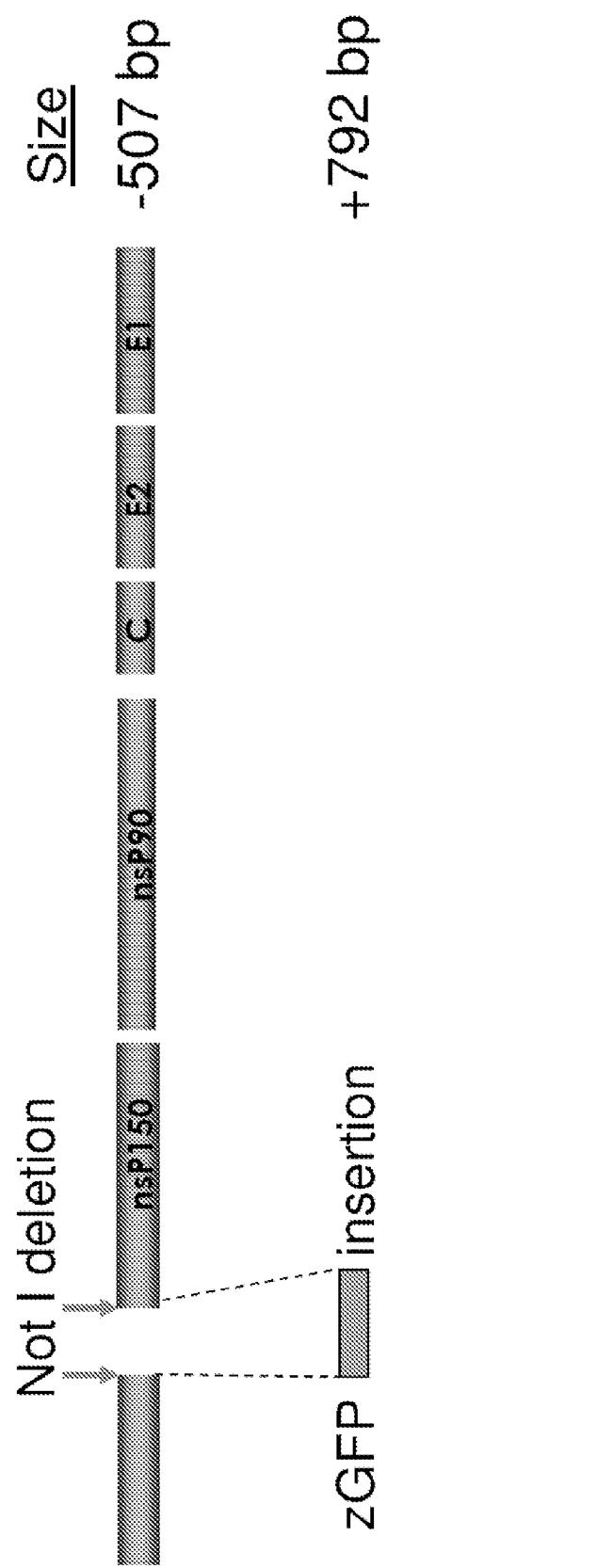
FIG. 1B is a schematic drawing of the expressed nonstructural proteins nsP150 and nsP90 and the structural proteins C, E2 and E1. The zGFP insert is expressed as part of the nsP150 polyprotein.
Figure 2:
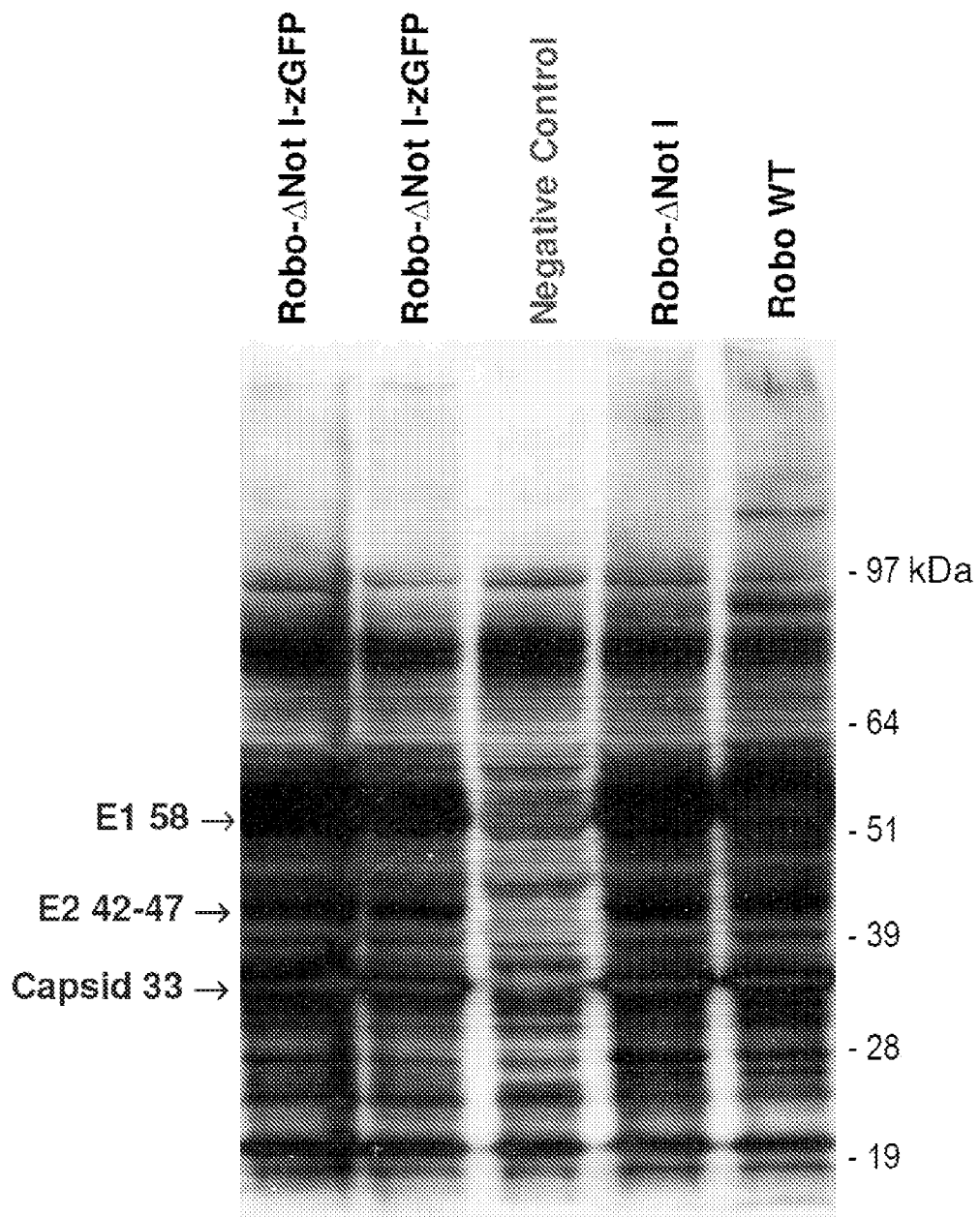
FIG. 2 is a digital image of a Western blot illustrating expression of rubella genes in Not I deletion/insertion mutants. Each full length rubella cDNA was transcribed, capped, and transfected into Vero cells. Expression of rubella structural proteins was detected by western blot of the $P_0$ cell lysates on day 12. Wild type rubella expressed Capsid 33, E1 and E2 proteins (lane 5) at the same level as Not I deleted rubella (lane 4). Two clones with zGFP inserted at the Not I site expressed normal levels of rubella proteins (lanes 1 and 2).
Figure 3:
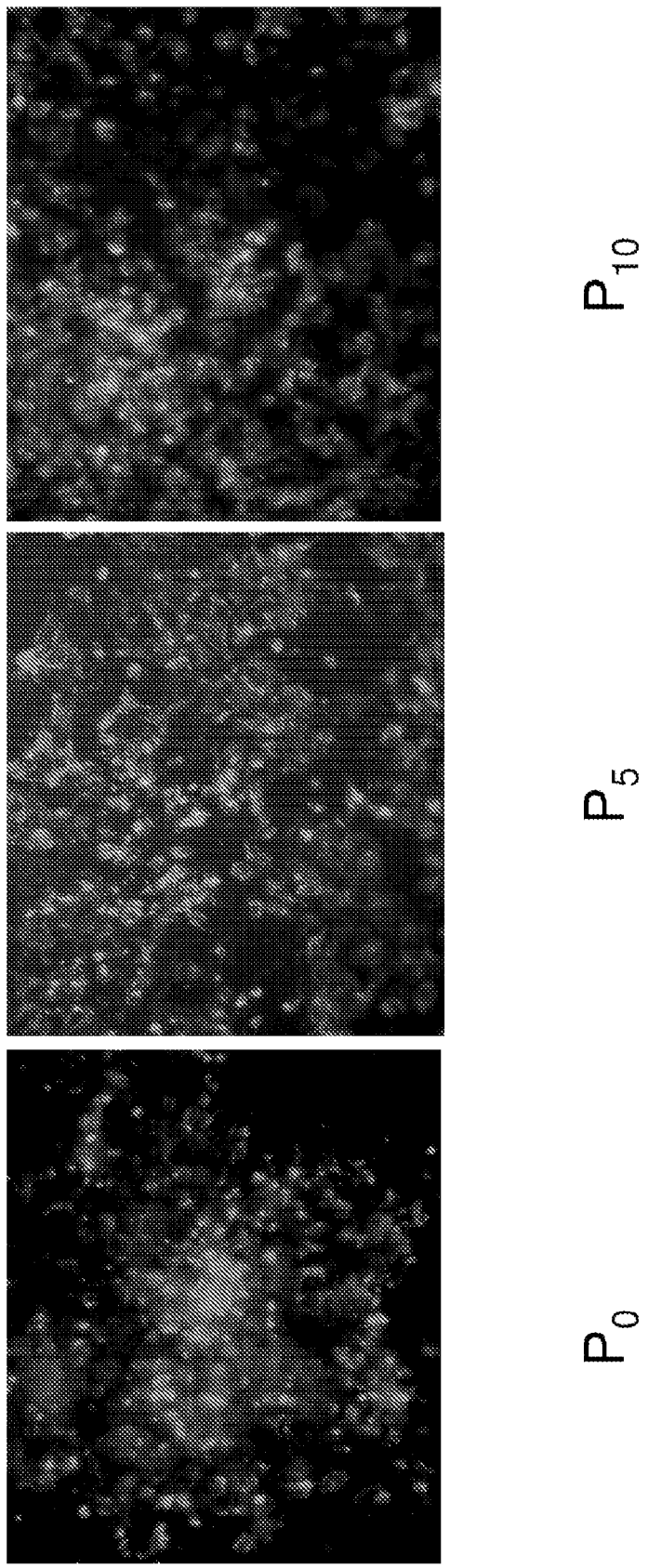
FIG. 3 is a series of digital images illustrating stable expression of zGFP in a live rubella vector at various cell passages. Culture supernatants were used to infect Vero cells over 10 passages. Multiple brightly fluorescent foci were observed after each passage, and the results after transfection ($P_0$), and passages $P_5$ and $P_{10}$ are shown. zGFP was expressed for at least 10 passages.
Figure 4:
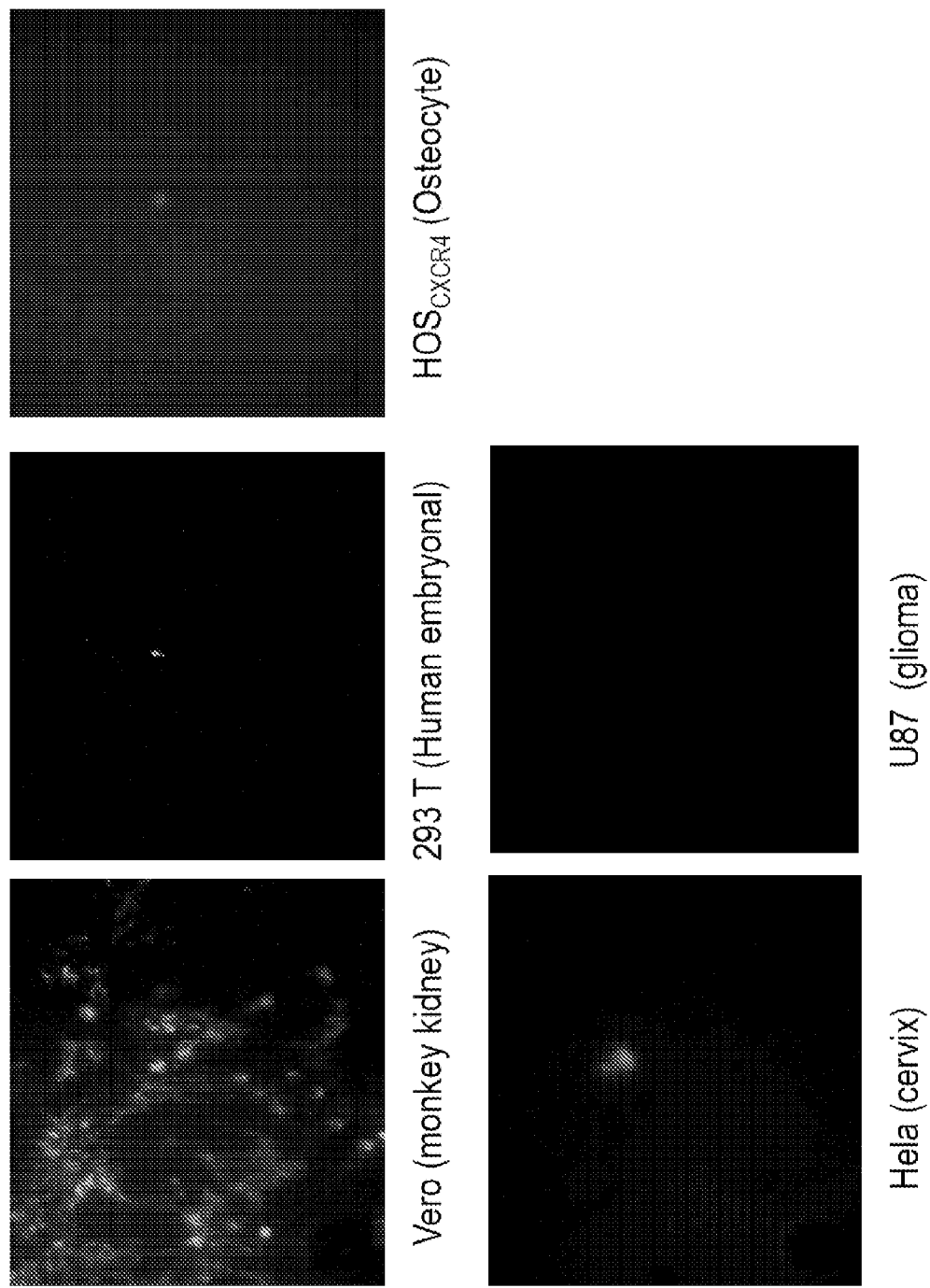
FIG. 4 is a series of digital images illustrating the host range and sensitivity to interferon of rubella-GFP in HeLa cervical cells, 293T embryonic neuronal cells, HOS osteocytes, and U87 glioma cells, as compared to monkey-derived Vero cells. Infection was limited to monkey-derived Vero cells as the viral growth was limited, if present at all, on fibroblasts, osteocytes, epithelial cells or glioma cells.

AIDS: acquired immune deficiency syndrome
bp: base pair
CTL: cytotoxic T lymphocyte
ELISA: enzyme linked immunosorbent assay
Gag: group-specific antigen
GFP: green fluorescent protein
Gp41: glycoprotein 41
Gp120: glycoprotein 120
HBsAg: hepatitis B surface antigen
HIV: human immunodeficiency virus
MHC: major histocompatibility complex
MPR: membrane proximal region
MW molecular weight
ORF: open reading frame
PCR: polymerase chain reaction
VLP: viral like particle Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting To facilitate review of the various embodiments of this disclosure, the following explanations of specific terms are provided:

Adjuvant: A vehicle used to enhance antigenicity; such as a suspension of minerals (alum, aluminum hydroxide, or phosphate) on which antigen is adsorbed; or water-in-oil emulsion in which antigen solution is emulsified in mineral oil (Freund incomplete adjuvant), sometimes with the inclusion of killed mycobacteria (Freund's complete adjuvant) to further enhance antigenicity (inhibits degradation of antigen and/or causes influx of macrophages). Immunstimulatory oligonucleotides (such as those including a CpG motif) can also be used as adjuvants (for example, see U.S. Pat. No. 6,194,388; U.S. Pat. No. 6,207,646; U.S. Pat. No. 6,214,806; U.S. Pat. No. 6,218,371; U.S. Pat. No. 6,239,116; U.S. Pat. No. 6,339,068; U.S. Pat. No. 6,406,705; and U.S. Pat. No. 6,429,199).

Amplification: Of a nucleic acid molecule (e.g., a DNA or RNA molecule) refers to use of a technique that increases the number of copies of a nucleic acid molecule in a specimen. An example of amplification is the polymerase chain reaction (PCR), in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Antibody: Immunoglobulin molecules and immunologically active portions of immunoglobulin molecules, that is, molecules that contain an antigen binding site that specifically binds (immunoreacts with) an antigen.

A naturally occurring antibody (e.g., IgG, IgM, IgD) includes four polypeptide chains, two heavy (H) chains and two light (L) chains interconnected by disulfide bonds. However, it has been shown that the antigen-binding function of an antibody can be performed by fragments of a naturally occurring antibody. Thus, these antigen-binding fragments are also intended to be designated by the term "antibody." Specific, non-limiting examples of binding fragments encompassed within the term antibody include (i) a Fab fragment consisting of the $V_L$, $V_H$, $C_L$ and $C_{H1}$ domains; (ii) an $F_d$ fragment consisting of the $V_H$ and $C_{H1}$ domains; (iii) an Fv fragment consisting of the $V_L$ and $V_H$ domains of a single arm of an antibody, (iv) a dAb fragment (Ward et al., Nature 341:544-546, 1989) which consists of a $V_H$ domain; (v) an isolated complimentarity determining region (CDR); and (vi) a F(ab')$_2$ fragment, a bivalent fragment comprising two Fab fragments linked by a disulfide bridge at the hinge region.

Methods of producing polyclonal and monoclonal antibodies are known to those of ordinary skill in the art, and many antibodies are available. See, e.g., Coligan, *Current Protocols in Immunology* Wiley/Greene, NY, 1991; and Harlow and Lane, *Antibodies: A Laboratory Manual* Cold Spring Harbor Press, NY, 1989; Stites et al., (eds.) *Basic and Clinical Immunology* (4th ed.) Lange Medical Publications, Los Altos, Calif., and references cited therein; Goding, *Monoclonal Antibodies: Principles and Practice* (2d ed.) Academic Press, New York, N.Y. 1986; and Kohler and Milstein, *Nature* 256: 495-497, 1975. Other suitable techniques for antibody preparation include selection of libraries of recombinant antibodies in phage or similar vectors. See, Huse et al., *Science* 246: 1275-1281, 1989; and Ward et al., *Nature* 341: 544-546, 1989. "Specific" monoclonal and polyclonal antibodies and antisera (or antiserum) will usually bind with a $K_D$ of at least about 0.1 µM, preferably at least about 0.01 µM or better, and most typically and preferably, 0.001 µM or better.

Immunoglobulins and certain variants thereof are known and many have been prepared in recombinant cell culture (e.g., see U.S. Pat. No. 4,745,055; U.S. Pat. No. 4,444,487; WO 88/03565; EP 256,654; EP 120,694; EP 125,023; Faoulkner et al., *Nature* 298:286, 1982; Morrison, *J. Immunol.* 123:793, 1979; Morrison et al., *Ann Rev. Immunol* 2:239, 1984). Detailed methods for preparation of chimeric (humanized) antibodies can be found in U.S. Pat. No. 5,482,856. Additional details on humanization and other antibody production and engineering techniques can be found in Borrebaeck (ed), *Antibody Engineering, $2^{nd}$ Edition* Freeman and Company, NY, 1995; McCafferty et al., *Antibody Engineering, A Practical Approach*, IRL at Oxford Press, Oxford, England, 1996, and Paul *Antibody Engineering Protocols* Humana Press, Towata, N.J., 1995.

Antigen: A compound, composition, or substance that can stimulate the production of antibodies or a T cell response in an animal, including compositions that are injected or absorbed into an animal. An antigen reacts with the products of specific humoral or cellular immunity, including those induced by heterologous immunogens. The term is used interchangeably with the term "immunogen." The term "antigen" includes all related antigenic epitopes. An "antigenic polypeptide" is a polypeptide to which an immune response, such as a T cell response or an antibody response, can be stimulated. "Epitope" or "antigenic determinant" refers to a site on an antigen to which B and/or T cells respond. In one embodiment, T cells respond to the epitope when the epitope is presented in conjunction with an MHC molecule. Epitopes can be formed both from contiguous amino acids (linear) or noncontiguous amino acids juxtaposed by tertiary folding of an antigenic polypeptide (conformational). Epitopes formed from contiguous amino acids are typically retained on exposure to denaturing solvents whereas epitopes formed by tertiary folding are typically lost on treatment with denaturing solvents. Normally, a B-cell epitope will include at least about 5 amino acids but can be as small as 3-4 amino acids. A T-cell epitope, such as a CTL epitope, will include at least about 7-9 amino acids, and a helper T-cell epitope at least about 12-20 amino acids. Normally, an epitope will include between about 5 and 15 amino acids, such as, 9, 10, 12 or 15 amino acids. The amino acids are in a unique spatial conformation. Methods of determining spatial conformation of epitopes include, for example, x-ray crystallography and multi-dimensional nuclear magnetic resonance spectroscopy. The term "antigen" denotes both subunit antigens, (for example, antigens which are separate and discrete from a whole organism with which the antigen is associated in nature), as well as killed, attenuated or inactivated bacteria, viruses, fungi, parasites or other microbes. Antibodies such as anti-idiotype antibodies, or fragments thereof, and synthetic peptide mimotopes, which can mimic an antigen or antigenic determinant, are also captured under the definition of antigen as used herein. Similarly, an oligonucleotide or polynucleotide which expresses an antigen or antigenic determinant in vivo, such as in gene therapy and DNA immunization applications, is also included in the definition of antigen herein.

An "antigen," when referring to a protein, includes a protein with modifications, such as deletions, additions and substitutions (generally conservative in nature) to the native sequence, so long as the protein maintains the ability to elicit an immunological response, as defined herein. These modifications may be deliberate, as through site-directed mutagenesis, or may be accidental, such as through mutations of hosts which produce the antigens.

Antigen Delivery Platform or Epitope Mounting Platform: In the context of the present disclosure, the terms "antigen delivery platform" and "epitope mounting platform" refer to a macromolecular complex including one or more antigenic epitopes. Delivery of an antigen (including one or more epitopes) in the context of an epitope mounting platform enhances, increases, ameliorates or otherwise improves a desired antigen-specific immune response to the antigenic epitope(s). The molecular constituents of the antigen delivery platform may be antigenically neutral or may be immunologically active, that is, capable of generating a specific immune response. Nonetheless, the term antigen delivery platform is utilized to indicate that a desired immune response is generated against a selected antigen that is a component of the macromolecular complex other than the platform polypeptide to which the antigen is attached. Accordingly, the epitope mounting platform is useful for delivering a wide variety of antigenic epitopes, including antigenic epitopes of pathogenic organisms such as bacteria and viruses. The antigen delivery platform of the present disclosure is particularly useful for the delivery of complex peptide or polypeptide antigens, which may include one or many distinct epitopes.

Antigenic polypeptide fragment: A polypeptide that is antigenic. In an example, an antigenic polypeptide fragment includes an HIV antigenic polypeptide fragment, such as a Gag, gp41 or gp120 antigenic polypeptide fragment or a HBsAg antigenic polypeptide fragment.

Conservative variants: "Conservative" amino acid substitutions are those substitutions that do not substantially affect or decrease a desired activity of a protein or polypeptide. For example, in the context of the present disclosure, a conservative amino acid substitution does not substantially alter or decrease the immunogenicity of an antigenic epitope. Similarly, a conservative amino acid substitution does not substantially affect the structure or, for example, the stability of a protein or polypeptide. Specific, non-limiting examples of a conservative substitution include the following examples:

| Original Residue Substitutions | Conservative |
|---|---|
| Ala | Ser |
| Arg | Lys |
| Asn | Gln; His |
| Asp | Glu |
| Cys | Ser |
| Gln | Asn |
| Glu | Asp |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity or antigenicity or substantially alter a structure, such as a secondary or tertiary structure, of a protein or polypeptide.

cDNA (complementary DNA): A piece of DNA lacking internal, non-coding segments (introns) and regulatory sequences that determine transcription. cDNA is typically synthesized in the laboratory by reverse transcription from messenger RNA extracted from cells.

Cytotoxic T lymphocyte (CTL): A type of lymphocyte (white blood cell) that is involved in the immune defenses of the body. Cytotoxic T cells are capable of inducing the death of inducing the death of infected somatic or tumor cells. They are also capable of killing cells infected with viruses (or other pathogens) or are otherwise damaged or dysfunctional. Most CTLs express T-cell receptors that can recognize a specific antigenic peptide bound to Class I MHC molecules.

Deletion: Removal or loss of a sequence of nucleic or amino acids. In one example, a deletion is an "in-frame deletion" (a deletion of a number of base pairs that is a multiple of three and thus constitutes a codon, and therefore does not disrupt the triplet reading frame.)

Diagnostic: Identifying the presence or nature of a pathologic condition, such as, but not limited to a condition induced by a viral or other pathogen. Diagnostic methods differ in their sensitivity and specificity. The "sensitivity" of a diagnostic assay is the percentage of diseased individuals who test positive (percent of true positives). The "specificity" of a diagnostic assay is 1 minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (or for example, the probability of severity) of a pathologic condition, such as a symptom induced by a viral infection or other pathogenic organism, or resulting indirectly from such an infection.

Epitope: An antigenic determinant. These are particular chemical groups or peptide sequences on a molecule that are antigenic, that is, that elicit a specific immune response. An antibody specifically binds a particular antigenic epitope on a polypeptide. Epitopes can be formed both from contiguous amino acids or noncontiguous amino acids juxtaposed by tertiary folding of a protein. Epitopes formed from contiguous amino acids are typically retained on exposure to denaturing solvents whereas epitopes formed by tertiary folding are typically lost on treatment with denaturing solvents. An epitope typically includes at least 3, and more usually, at least 5, about 9, or 8-10 amino acids in a unique spatial conformation. Methods of determining spatial conformation of epitopes include, for example, x-ray crystallography and multi-dimensional nuclear magnetic resonance spectroscopy. See, e.g., "Epitope Mapping Protocols" in *Methods in Molecular Biology*, Vol. 66, Glenn E. Morris, Ed (1996). In some embodiments, an epitope binds an MHC molecule, e.g., an HLA molecule or a DR molecule. In some embodiments, an epitope is a cytotoxic T lymphocyte (CTL) epitope, such as a CTL epitope of Gag.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (typically, ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences.

Glycoprotein 41 (gp41): An HIV-1 envelope glycoprotein that mediates receptor binding and HIV entry into a cell. Gp41 includes a membrane proximal region (MPR) and a transmembrane spanning domain. Gp41 is immunogenic and induces a variety of neutralizing antibodies, such as neutralizing antibodies directed to 2F5, 4E10 and Z13. These three gp41 neutralizing antibodies recognize the MPR of the HIV-1 gp41 glycoprotein.

Gp41 antigenic insert: A peptide fragment that includes a MPR of gp41 and a transmembrane spanning region of gp41. In an example, the MPR (also referred to as the antigenic polypeptide fragment) of gp41 includes the amino acid sequence of SEQ ID NO: 1 and a transmembrane spanning region of gp41 including the amino acid sequence set forth as SEQ ID NO: 25 ($X_4$FIMIVGGL$X_5$GLRIVFTX$_6$LSIV, $X_1$, $X_2$ and $X_3$ are any amino acid and $X_4$, $X_5$, and $X_6$ are any hydrophobic amino acid). For example, the antigenic polypeptide fragment of gp41 is between 16 and 150 amino acids in length (such as 28 and 150 amino acids in length) and the transmembrane spanning region of gp41 is between 22 and 40 amino acids in length and wherein the transmembrane spanning region of gp41 is C-terminal to the antigenic polypeptide fragment of gp41.

Glycoprotein 120 (gp120): An envelope protein from Human Immunodeficiency Virus (HIV). The envelope protein is initially synthesized as a longer precursor protein of 845-870 amino acids in size, designated gp160. Gp160 forms a homotrimer and undergoes glycosylation within the Golgi apparatus. It is then cleaved by a cellular protease into gp120 and gp41. Gp41 contains a transmembrane domain and remains in a trimeric configuration; it interacts with gp120 in a non-covalent manner. Gp120 contains most of the external, surface-exposed, domains of the envelope glycoprotein complex, and it is gp120 which binds both to the cellular CD4 receptor and to the cellular chemokine receptors (such as CCR5).

Mature gp120 wildtype polypeptides have about 500 amino acids in the primary sequence. Gp120 is heavily N-glycosylated giving rise to an apparent molecular weight of 120 kD. Exemplary sequence of wt gp160 polypeptides are shown on GENBANK®, for example accession numbers AAB05604 and AAD12142 incorporated herein by reference in their entirety as available on Oct. 16, 2009.

The gp120 core has a unique molecular structure, which comprises two domains: an "inner" domain (which faces gp41) and an "outer" domain (which is mostly exposed on the surface of the oligomeric envelope glycoprotein complex). The two gp120 domains are separated by a "bridging sheet" that is not part of either domain. The gp120 core comprises 25 beta strands, 5 alpha helices, and 10 defined loop segments. The 10 defined loop segments include five conserved regions (C1-C5) and five regions of high variability (V1-V5).

Gp120 polypeptides also include "gp120-derived molecules" which encompasses analogs (non-protein organic molecules), derivatives (chemically functionalized protein molecules obtained starting with the disclosed protein sequences) or mimetics (three-dimensionally similar chemicals) of the native gp120 structure, as well as proteins sequence variants (such as mutants, for example deletions, such as loop deletions, insertions or point mutation in any combination), genetic alleles, fusions proteins of gp120, or combinations thereof.

The numbering used in gp120 polypeptides disclosed herein is relative to the HXB2 numbering scheme as set forth in *Numbering Positions in HIV Relative to HXB2CG* Bette Korber et al., Human Retroviruses and AIDS 1998: A Compilation and Analysis of Nucleic Acid and Amino Acid Sequences. Korber B, Kuiken C L, Foley B, Hahn B, McCutchan F, Mellors J W, and Sodroski J, Eds. Theoretical Biology and Biophysics Group, Los Alamos National Laboratory, Los Alamos, N. Mex. which is incorporated by reference herein in its entirety.

As used herein, a variant gp120 polypeptide is a gp120 polypeptide in which one or more amino acids have been altered (e.g., deleted or substituted). In one example, a variant gp120 polypeptide is a gp120 polypeptide in which at least 8 consecutive residues, such as 9, 10, 11 or 12 consecutive residues, of the fourth conserved loop (C4) between residues 419 and 434 of gp120 of SEQ ID NO: 63 has been deleted. In a particular example, a variant gp120 polypeptide includes a gp120 polypeptide in which residues 424-432 are deleted. Additional variant gp120 polypeptides include deletions of INMWQKVGK (residues 424-432 of SEQ ID NO:63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), IINMWQKVGK (residues 423-432 of SEQ ID NO: 63). In other embodiments, variant gp120 polypeptides include combinations of the amino and carboxyl ends between residues 419 and 434.

Any of the disclosed variant gp120 polypeptide including deletions in C4 can also include a deletion in the V1V2 loop region (with an amino acid sequence set forth in SEQ ID NO: 63); see S R Pollard and D C Wiley, *EMBO J.* 11:585-91, 1992 which is hereby incorporated by reference in its entirety.

Group-specific antigen (Gag): A gene which encodes core structural proteins of HIV or SIV. In particular, Gag contains approximately 1500 nucleotides and encodes four separate proteins (capsid protein (p24), matrix protein (p17), nucleocapsid (p9) and p6) which form the building blocks for the viral core. Gag forms a spherical shell underlying the membrane of an immature viral particle. After proteolytic maturation of Gag, the capsid (CA) domain of Gag reforms into a conical shell enclosing the RNA genome. This mature shell contains 1,000-1,500 CA proteins assembled into a hexameric lattice with a spacing of 10 nm. Exemplary nucleic acid and amino acid sequences are known to those of skill in the art including the amino acid sequences provided in Table 1 below.

Hepatitis B Surface Antigen (HBsAg): HBsAg is composed of 3 polypeptides, preS1, preS2 and S that are produced from alternative translation start sites. The surface proteins have many functions, including attachment and penetration of the virus into hepatocytes at the beginning of the infection process. The surface antigen is a principal component of the hepatitis B envelope. HBsAg has four membrane spanning domains. Exemplary nucleic acid and amino acid sequences are known to those of skill in the art and are shown on GENBANK®, for example accession numbers NM_001166119, NM_001130714, NM_001130713, NM_016269, BAF48754, BAF48753, BAF48752, BAF48751, AAA35977, AAA35976, AAA35975, AAA35974 and AAA35973 all of which are incorporated herein by reference in their entirety as available on Oct. 16, 2009.

As used herein, a variant HBsAg can include natural variants or recombinant variants such as a HBsAg that includes a MPR from gp41. In a particular example, a variant HBsAg includes a MPR and a membrane spanning domain from gp41.

Heterologous antigenic insert: An insert with an antigenic sequence that is not normally (in the wild-type sequence) found adjacent to a second sequence. In one embodiment, the antigenic insert is from a different genetic source, such as a virus or organism, than the second sequence. In one particular example, the antigenic insert is an HIV envelope protein or an HIV Gag protein. For example, the heterologous antigenic insert is a MPR of the HIV-1 gp41 glycoprotein. In other examples, the heterologous antigenic insert is not a rubella structural protein, such as a capsid.

Host cells: Cells in which a polynucleotide, for example, a polynucleotide vector or a viral vector, can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Human Immunodeficiency Virus (HIV): A virus, known to cause AIDS, that includes HIV-1 and HIV-2. HIV-1 is composed of two copies of single-stranded RNA enclosed by a conical capsid including the viral protein p24, typical of lentiviruses. The capsid is surrounded by a plasma membrane of host-cell origin.

The RNA genome has at least three genes, gag, pol, and env, which contain information needed to make the structural proteins for new virus particles. For example, the envelope protein of HIV-1 is made up of a glycoprotein called gp160. The mature, virion associated envelope protein is a trimeric molecule composed of three gp120 and three gp41 subunits held together by weak noncovalent interactions. This structure is highly flexible and undergoes substantial conformational changes upon gp120 binding with CD4 and chemokine coreceptors, which leads to exposure of the fusion peptides of gp41 that insert into the target cell membrane and mediate viral entry. Following oligomerization in the endoplasmic reticulum, the gp160 precursor protein is cleaved by cellular proteases and is transported to the cell surface. During the course of HIV-1 infection, the gp120 and gp41 subunits are shed from virions and virus-infected cells due to the noncovalent interactions between gp120 and gp41 and between gp41 subunits.

Immune response: A response of a cell of the immune system, such as a B cell, T cell, or monocyte, to a stimulus. In some cases, the response is specific for a particular antigen (that is, an "antigen-specific response"). In some cases, an immune response is a T cell response, such as a CD4+ response or a CD8+ response. Alternatively, the response is a B cell response, and results in the production of specific antibodies. For purposes of the present invention, a "humoral immune response" refers to an immune response mediated by antibody molecules, while a "cellular immune response" is one mediated by T-lymphocytes and/or other white blood cells. A "protective immune response" is an immune response that inhibits a detrimental function or activity (such as a detrimental effect of a pathogenic organism such as a virus), reduces infection by a pathogenic organism (such as, a virus), or decreases symptoms that result from infection by the pathogenic organism. A protective immune response can be measured, for example, by the inhibition of viral replication or plaque formation in a plaque reduction assay or ELISA-neutralization assay (NELISA), or by measuring resistance to viral challenge in vivo.

An immunogenic composition can induce a B cell response. The ability of a particular antigen to stimulate a B cell response can be measured by determining if antibodies are present that bind the antigen. In one example, neutralizing antibodies are produced.

One aspect of cellular immunity involves an antigen-specific response by cytolytic T-cells ("CTL"s). CTLs have specificity for peptide antigens that are presented in association with proteins encoded by the major histocompatibility complex (MHC) and expressed on the surface of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

The ability of a particular antigen to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, for example, Erickson et al. (1993) *J. Immunol.* 151:4189-4199; Doe et al. (1994) *Eur. J. Immunol.* 24:2369-2376. Recent methods of measuring cell-mediated immune response include measurement of intracellular cytokines or cytokine secretion by T-cell populations, or by measurement of epitope specific T-cells (for example, by the tetramer technique) (reviewed by McMichael and O'Callaghan (1998) *J. Exp. Med.* 187 (9) 1367-1371; Mcheyzer-Williams et al. (1996) *Immunol. Rev.* 150:5-21; Lalvani et al. (1997) *J. Exp. Med.* 186: 859-865).

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or gamma-delta T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

Immunogenic composition: A composition comprising at least one epitope of a virus, or other pathogenic organism, that induces a measurable CTL response, or induces a measurable B cell response (for example, production of antibodies that specifically bind the epitope). It further refers to isolated nucleic acids encoding an immunogenic epitope of virus or other pathogen that can be used to express the epitope (and thus be used to elicit an immune response against this polypeptide or a related polypeptide expressed by the pathogen). For in vitro use, the immunogenic composition may consist of the isolated nucleic acid, protein or peptide. For in vivo use, the immunogenic composition will typically include the nucleic acid, protein or peptide in pharmaceutically acceptable carriers or excipients, and/or other agents, for example, adjuvants. An immunogenic polypeptide (such as an antigenic polypeptide), or nucleic acid encoding the polypeptide, can be readily tested for its ability to induce a CTL or antibody response by art-recognized assays.

Immunogenic peptide: A peptide which comprises an allele-specific motif or other sequence such that the peptide will bind an MHC molecule and induce a cytotoxic T lymphocyte ("CTL") response, or a B cell response (e.g. antibody production) against the antigen from which the immunogenic peptide is derived.

Inhibiting an infection: Inhibiting infection by a pathogen such as a virus, such as a lentivirus, or other virus, refers to inhibiting the full development of a disease either by avoiding initial infection or inhibiting development of the disease process once it is initiated. For example, inhibiting a viral infection refers to lessening symptoms resulting from infection by the virus, such as preventing the development of symptoms in a person who is known to have been exposed to the virus, or to lessening virus number or infectivity of a virus in a subject exposed to the virus.

Isolated: An "isolated" biological component (such as a nucleic acid or protein or organelle) has been substantially separated or purified away from other biological components in the cell of the organism in which the component naturally occurs, for example, other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, affinity tags, enzymatic linkages, and radioactive isotopes. An affinity tag is a peptide or polypeptide sequence capable of specifically binding to a specified substrate, for example, an organic, non-organic or enzymatic substrate or cofactor. A polypeptide including a peptide or polypeptide affinity tag can typically be recovered, for example, purified or isolated, by means of the specific interaction between the affinity tag and its substrate. An exemplary affinity tag is a poly-histidine (e.g., six-histidine) affinity tag which can specifically bind to non-organic metals such as nickel and/or cobalt. Additional affinity tags are well known in the art.

Linking peptide: A linking peptide (or linker sequence) is an amino acid sequence that covalently links two polypeptide domains. Linking peptides can be included between a polypeptide and an antigenic epitope to provide rotational freedom to the linked polypeptide domains and thereby to promote proper domain folding. Linking peptides, which are generally between 2 and 25 amino acids in length, are well known in the art and include, but are not limited to the amino acid sequences glycine-proline-glycine-proline (GPGP) (SEQ ID NO: 37) and glycine-glycine-serine (GGS), as well as the glycine(4)-serine spacer described by Chaudhary et al., Nature 339:394-397, 1989. In some cases multiple repeats of a linking peptide are present.

Lymphocytes: A type of white blood cell that is involved in the immune defenses of the body. There are two main types of lymphocytes: B cells and T cells. "T lymphocytes" or "T cells" are non-antibody producing lymphocytes that constitute a part of the cell-mediated arm of the immune system. T cells arise from immature lymphocytes that migrate from the bone marrow to the thymus, where they undergo a maturation process under the direction of thymic hormones. Here, the mature lymphocytes rapidly divide increasing to very large numbers. The maturing T cells become immunocompetent based on their ability to recognize and bind a specific antigen. Activation of immunocompetent T cells is triggered when an antigen binds to the lymphocyte's surface receptors. T cells include, but are not limited to, CD4+ T cells and CD8+ T cells. A CD4+ T lymphocyte is an immune cell that carries a marker on its surface known as "cluster of differentiation 4" (CD4). These cells, also known as helper T cells, help orchestrate the immune response, including antibody responses as well as killer T cell responses. CD8+ T cells carry the "cluster of differentiation 8" (CD8) marker. In one embodiment, a CD8 T cell is a cytotoxic T lymphocyte. In another embodiment, a CD8 cell is a suppressor T cell.

Membrane proximal region (MPR) of gp41: A region that is immediately N-terminal of the transmembrane region of gp41. The MPR is highly hydrophobic (50% of residues are hydrophobic) and is highly conserved across many HIV clades (Zwick, M. B., et al., *J Virol,* 75 (22): p. 10892-905, 2001). The conserved MPR of HIV-1 gp41 is a target of two broadly neutralizing human monoclonal antibodies, 2F5 and 4E10. The core of the 2F5 epitope has been shown to be ELDKWAS (SEQ ID NO: 35). With this epitope, the residues D, K, and W were found to be most critical for recognition by 2F5. The core of the 4E10 epitope, NWFDIT (SEQ ID NO: 36), maps just C-terminal to the 2F5 epitope on the gp41 ectodomain.

Oligonucleotide: A linear polynucleotide sequence of up to about 100 nucleotide bases in length.

Open reading frame ("ORF"): A series of nucleotide triplets (codons) coding for amino acids without any internal termination codons. These sequences are usually translatable into a polypeptide (peptide or protein). In one example, an open reading frame is a rubella non-structural protein open reading frame, such as one coding amino acids that include two NotI restriction enzyme sites. In other examples, an open reading frame is a rubella structural protein open reading frame.

Operatively linked: A first nucleic acid sequence is operatively linked with a second nucleic acid sequence when the first nucleic acid sequence is placed in a functional relationship with the second nucleic acid sequence. For instance, a promoter is operatively linked to a coding sequence if the promoter affects the transcription or expression of the coding sequence. Generally, operatively linked DNA sequences are contiguous and, where necessary to join two protein-coding regions, in the same reading frame, for example, two polypeptide domains or components of a fusion protein.

Pharmaceutically acceptable carriers and/or pharmaceutically acceptable excipients: The pharmaceutically acceptable carriers or excipients of use are conventional. *Remingtons: The Science and Practice of Pharmacy,* University of the Sciences in Philadelphia, Lippincott Williams & Wilkins, Philadelphia, Pa., 21st Edition (2005), describes compositions and formulations suitable for pharmaceutical delivery of the constructs disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (e.g., powder, pill, tablet, or capsule forms), conventional non-toxic solid carriers can include, for example, pharmaceutical grades of mannitol, lactose, starch or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition used to achieve a desired effect in a subject. For instance, this can be the amount of the composition necessary to inhibit viral (or other pathogen) replication or to prevent or measurably alter outward symptoms of viral (or other pathogenic) infection. When administered to a subject, a dosage will generally be used that will achieve target tissue concentrations (for example, in lymphocytes) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Polypeptide: Any chain of amino acids, regardless of length or post-translational modification (for example, glycosylation or phosphorylation), such as a protein or a fragment or subsequence of a protein. The term "peptide" is typically used to refer to a chain of amino acids of between 3 and 30 amino acids in length. For example an immunologically relevant peptide may be between about 7 and about 25 amino acids in length, e.g., between about 8 and about 10 amino acids.

In the context of the present disclosure, a polypeptide can be a fusion protein comprising a plurality of constituent polypeptide (or peptide) elements. Typically, the constituents of the fusion protein are genetically distinct, that is, they originate from distinct genetic elements, such as genetic elements of different organisms or from different genetic elements (genomic components) or from different locations on a single genetic element, or in a different relationship than found in their natural environment. Nonetheless, in the context of a fusion protein the distinct elements are translated as a single polypeptide. The term monomeric fusion protein (or monomeric fusion protein subunit) is used synonymously with such a single fusion protein polypeptide to clarify reference to a single constituent subunit where the translated fusion proteins assume a multimeric tertiary structure.

Probes and primers: A probe comprises an isolated nucleic acid attached to a detectable label or reporter molecule. Primers are short nucleic acids, preferably DNA oligonucleotides, for example, a nucleotide sequence of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example, by the polymerase chain reaction (PCR) or other nucleic-acid amplification methods known in the art. One of skill in the art will appreciate that the specificity of a particular probe or primer increases with its length. Thus, for example, a primer comprising 20 consecutive nucleotides will anneal to a target with a higher specificity than a corresponding primer of only about 15 nucleotides. Thus, in order to obtain greater specificity, probes and primers may be selected that comprise 20, 25, 30, 35, 40, 50 or more consecutive nucleotides.

Promoter: A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (for example, metallothionein promoter) or from mammalian viruses (for example, the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Purified: The term "purified" does not require absolute purity; rather, it is intended as a relative term. Thus, for example, a purified nucleic acid is one in which the nucleic acid is more enriched than the nucleic acid in its natural environment within a cell. Similarly, a purified peptide preparation is one in which the peptide or protein is more enriched than the peptide or protein is in its natural environment within a cell. In one embodiment, a preparation is purified such that the protein or peptide represents at least 50% (such as, but not limited to, 70%, 80%, 90%, 95%, 98% or 99%) of the total peptide or protein content of the preparation.

Recombinant: A recombinant nucleic acid is one that has a sequence that is not naturally occurring or has a sequence that is made by an artificial combination of two otherwise separated segments of sequence, for example, a polynucleotide encoding a fusion protein. This artificial combination is often accomplished by chemical synthesis or, more commonly, by the artificial manipulation of isolated segments of nucleic acids, e.g., by genetic engineering techniques.

Rubella: A small, quasi-spherical, enveloped, nonsegmented, plus-strand RNA virus that is a member of the rubivirus genus of the togavirus family (Togaviridae). Molecular biology of rubella virus is summarized by Frey, T. K. in *Adv. Virus Res.* 44:69-160 (1994) which is hereby incorporated by reference in its entirety. The rubella virion (virus particle) includes a single-stranded RNA encapsidated in an icosahedral nucleocapsid surrounded by a lipid envelope. This virion has at least two RdRp nonstructural proteins (nsP150 and nsP90) and three structural proteins (Capsid (C), E2 and E1). Multiple copies of a viral protein, designated the C protein (molecular weight (MW)=32,000-38,000 daltons), make up the nucleocapsid. Two types of viral glycoprotein, designated E1 and E2 (MW=53,000-58,000 daltons and 42,000-48,000 daltons, respectively), are embedded in the envelope. The E2 glycoprotein has been further subdivided into two subgroups, designated E2a and E2b, by their ability to migrate differently when resolved by polyacrylamide gel electrophoresis. E1 is the viral hemagglutinin. Neutralizing epitopes have been found on both E1 and E2. In one example, MPR and other HIV antigenic determinants are linked to E2 and E1 to elicit similar neutralizing antibodies against HIV.

The rubella genome consists of RNA of positive polarity that is roughly 10,000 nucleotides long and is capped and polyadenylated. In infected cells, three viral RNA species are synthesized: the genomic RNA, which also is the mRNA for translation of the nonstructural proteins (whose function is in viral RNA synthesis) from a long open reading frame (ORF) at the 5' end of the genome; a complementary genome-length RNA of minus polarity which is the template for synthesis of plus-strand RNA species; and a subgenomic (SG) RNA which is initiated internally and contains the sequences of the 3'-terminal one-third of the genome (3327 nucleotides) and serves as the mRNA for the translation of the structural proteins. The structural proteins are proteolytically processed from a polyprotein precursor during translation. The order of these proteins in the polyprotein is NH2-C-E2-E1-COOH.

Sequence identity: The similarity between amino acid (and polynucleotide) sequences is expressed in terms of the similarity between the sequences, otherwise referred to as sequence identity. Sequence identity is frequently measured in terms of percentage identity (or similarity); the higher the percentage, the more similar are the primary structures of the two sequences. In general, the more similar the primary structures of two amino acid sequences, the more similar are the higher order structures resulting from folding and assembly. However, the converse is not necessarily true, and polypeptides with low sequence identity at the amino acid level can nonetheless have highly similar tertiary and quaternary structures.

Methods of determining sequence identity are well known in the art. Various programs and alignment algorithms are described in: Smith and Waterman, *Adv. Appl. Math.* 2:482, 1981; Needleman and Wunsch, *J. Mol. Biol.* 48:443, 1970; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Another indicia of sequence similarity between two nucleic acids is the ability to hybridize. The more similar are the sequences of the two nucleic acids, the more stringent the conditions at which they will hybridize. The stringency of hybridization conditions are sequence-dependent and are different under different environmental parameters. Thus, hybridization conditions resulting in particular degrees of stringency will vary depending upon the nature of the hybridization method of choice and the composition and length of the hybridizing nucleic acid sequences. Generally, the temperature of hybridization and the ionic strength (especially the $Na^+$ and/or $Mg^{++}$ concentration) of the hybridization buffer will determine the stringency of hybridization, though wash times also influence stringency. Generally, stringent conditions are selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Conditions for nucleic acid hybridization and calculation of stringencies can be found, for example, in Sambrook et al., *Molecular Cloning: A Laboratory Manual*, Cold Spring Harbor Laboratory Press, Cold Spring Harbor, N.Y., 2001; Tijssen, *Hybridization With Nucleic Acid Probes, Part I: Theory and Nucleic Acid Preparation*, Laboratory Techniques in Biochemistry and Molecular Biology, Elsevier Science Ltd., NY, N.Y., 1993. and Ausubel et al. *Short Protocols in Molecular Biology*, 4th ed., John Wiley & Sons, Inc., 1999.

For purposes of the present disclosure, "stringent conditions" encompass conditions under which hybridization will only occur if there is less than 25% mismatch between the hybridization molecule and the target sequence. "Stringent conditions" may be broken down into particular levels of stringency for more precise definition. Thus, as used herein, "moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 6% mismatch will not hybridize. In contrast nucleic acids that hybridize under "low stringency conditions include those with much less sequence identity, or with sequence identity over only short subsequences of the nucleic acid.

For example, a specific example of progressively higher stringency conditions is as follows: 2×SSC/0.1% SDS at about room temperature (hybridization conditions); 0.2× SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., *Molecular Cloning: A Laboratory Manual*, 2nd ed., vol. 1-3, ed. Sambrook et al., Cold Spring Harbor Laboratory Press, Cold Spring Harbor, N.Y., 1989). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Subject: Living multi-cellular vertebrate organisms, a category that includes both human and veterinary subjects, including human and non-human mammals.

Therapeutically active polypeptide: An agent, such as an epitope of a virus or other pathogen that causes induction of an immune response, as measured by clinical response (for example increase in a population of immune cells, increased cytolytic activity against the epitope). Therapeutically active molecules can also be made from nucleic acids. Examples of a nucleic acid based therapeutically active molecule is a nucleic acid sequence that encodes an epitope of a protein of a virus or other pathogen, wherein the nucleic acid sequence is operatively linked to a control element such as a promoter.

Therapeutically Effective Amount: An amount of a composition that alone, or together with an additional therapeutic agent(s) (for example nucleoside/nucleotide reverse transcriptase inhibitors, a non-nucleoside reverse transcriptase inhibitors, protease inhibitors, fusion/entry inhibitors or integrase inhibitors) induces the desired response (e.g., inhibition of HIV infection or replication). In one example, a desired response is to inhibit HIV replication in a cell to which the therapy is administered. HIV replication does not need to be completely eliminated for the composition to be effective. For example, a composition can decrease HIV replication by a desired amount, for example by at least 10%, at least 20%, at least 50%, at least 60%, at least 70%, at least 80%, at least 90%, at least 95%, at least 98%, or even at least 100% (elimination of HIV), as compared to HIV replication in the absence of the composition.

In another example, a desired response is to inhibit HIV infection. The HIV infected cells do not need to be completely eliminated for the composition to be effective. For example, a composition can decrease the number of HIV infected cells by a desired amount, for example by at least 10%, at least 20%, at least 50%, at least 60%, at least 70%, at least 80%, at least 90%, at least 95%, at least 98%, or even at least 100% (elimination of detectable HIV infected cells), as compared to the number of HIV infected cells in the absence of the composition.

A therapeutically effective amount of a composition can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 μg-10 mg per 70 kg body weight if administered intravenously.

Transformed or Transfected: A transformed cell is a cell into which a nucleic acid molecule has been introduced by molecular biology techniques. As used herein, the term introduction or transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transmembrane spanning region or membrane spanning domain of gp41: A region or domain of gp41 that is immediately C-terminal to the membrane proximal region of gp41. An example of a transmembrane spanning region is provided in SEQ ID NO: 25.

Treating a disease: "Treatment" refers to a therapeutic intervention that ameliorates a sign or symptom of a disease or other pathological condition, such as an infection, for example a sign or symptom of HIV. Treatment can also induce remission or cure of a condition, such as elimination of detectable HIV infected cells. In particular examples, treatment includes preventing a disease, for example by inhibiting the full development of a disease, such as HIV, by inhibiting HIV replication or infection or the development of AIDS. Prevention of a disease does not require a total absence of disease. For example, a decrease of at least 50% can be sufficient.

Vaccine: A vaccine is a pharmaceutical composition that elicits a prophylactic or therapeutic immune response in a subject. In some cases, the immune response is a protective immune response. Typically, a vaccine elicits an antigen-specific immune response to an antigen of a pathogen, for example, a bacterial or viral pathogen, or to a cellular constituent correlated with a pathological condition. A vaccine may include a polynucleotide, a peptide or polypeptide, a virus, a bacteria, a cell or one or more cellular constituents. In some cases, the virus, bacteria or cell may be inactivated or attenuated to prevent or reduce the likelihood of infection, while maintaining the immunogenicity of the vaccine constituent.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art.

Virus: Microscopic infectious organism that reproduces inside living cells. A virus consists essentially of a core of a single nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so.

"Retroviruses" are RNA viruses wherein the viral genome is RNA. When a host cell is infected with a retrovirus, the genomic RNA is reverse transcribed into a DNA intermediate which is integrated very efficiently into the chromosomal DNA of infected cells. The integrated DNA intermediate is referred to as a provirus. The term "lentivirus" is used in its conventional sense to describe a genus of viruses containing reverse transcriptase. The lentiviruses include the "immunodeficiency viruses" which include human immunodeficiency virus (HIV) type 1 and type 2 (HIV-1 and HIV-2), simian immunodeficiency virus (SIV), and feline immunodeficiency virus (FIV). HIV-1 is a retrovirus that causes immunosuppression in humans (HIV disease), and leads to a disease complex known as AIDS. "HIV infection" refers to the process in which HIV enters macrophages and CD4+ T cells by the adsorption of glycoproteins on its surface to receptors on the target cell followed by fusion of the viral envelope with the cell membrane and the release of the HIV capsid into the cell. "HIV disease" refers to a well-recognized constellation of signs and symptoms (including the development of opportunistic infections) in persons who are infected by an HIV virus, as determined by antibody or western blot studies. Laboratory findings associated with this disease are a progressive decline in T cells.

Virus-like particle or VLP: A nonreplicating, viral shell, derived from any of several viruses. VLPs are generally composed of one or more viral proteins, such as, but not limited to, those proteins referred to as capsid, coat, shell, surface and/or envelope proteins, or particle-forming polypeptides derived from these proteins. VLPs can form spontaneously upon recombinant expression of the protein in an appropriate expression system. Methods for producing particular VLPs are known in the art. The presence of VLPs following recombinant expression of viral proteins can be detected using conventional techniques known in the art, such as by electron microscopy, biophysical characterization, and the like. See, for example, Baker et al. (1991) *Biophys. J.* 60:1445-1456; Hagensee et al. (1994) *J. Virol.* 68:4503-4505. For example, VLPs can be isolated by density gradient centrifugation and/or identified by characteristic density banding. Alternatively, cryoelectron microscopy can be performed on vitrified aqueous samples of the VLP preparation in question, and images recorded under appropriate exposure conditions.

II. Description of Several Embodiments

Some of the most successful vaccines consist of live attenuated viruses. However, for many pathogenic viruses, such as HIV, it has not been possible to produce a live attenuated vaccine.

Rubella virus has a number of desirable properties for a live vector. The live attenuated rubella vaccine strain is immunogenic in humans at a dose of just 5,000 PFU. Its safety and immunogenicity have been demonstrated in millions of people, so a vector based on this strain might be used without further attenuation. One dose protects for life (against rubella). In monkeys, rubella virus grows exponentially until antibodies appear at around day 10, and it is shed for another week in mucosal secretions. It elicits systemic and mucosal immunity. It has no DNA intermediate, cannot integrate into host DNA, and does not persist after the acute infection. A full length, infectious cDNA clone is available, both for wild type rubella and for the RA27/3 vaccine strain, making it possible to manipulate rubella genetically.

Despite these desirable properties, the use of rubella virus for a live vector has been unsuccessful because of the inability to maintain stable expression of foreign genes in a live rubella vector. Moreover, it remained unclear which foreign genes could be inserted, where to insert them, and how large an insert could be accommodated in viral RNA and packaged into virions. For example, if the insert exceeded the size limit, selective pressure resulted in an unstable construct with loss of gene expression.

Disclosed herein is a rubella viral vector construct that is capable of expressing foreign genes at a high level without interfering with expression of essential rubella genes and packaging of live virus. This vector construct maintains stable expression of foreign genes for multiple passages. Thus, the inventors have created a new way to use rubella vaccine as a viral vector to express an additional protein antigen of a second virus. In this way, the safety and immunogenicity of a rubella vaccine can be combined with the antigenicity of another virus.

For example, previous vectors, with up to 1000 fold less potency, have been tested for immunization with HIV antigens, and they all failed to protect against HIV infection. The vector construct disclosed herein is believed to be the first vector that can actually immunize against this pathogen. Further, unlike previous vectors, the safety and immunogenicity of a live attenuated rubella vaccine has been demonstrated in tens of millions of children throughout the world. Vaccine potency is based on the fact that this is a replicating vector that simulates infection. One dose protects for life against rubella. The vaccine induces mucosal as well as systemic immunity. Each of these properties would be desirable in a vaccine against HIV or other pathogens.

At the same time, the disclosed vector construct can also be the lowest cost vector for virtually any viral pathogen, since the immunizing dose is so low that one ml of culture fluid can make up to 1,000 doses of vaccine. The market could be more than 100 million doses per year. Moreover, in the United States, the disclosed vector construct can be used to generate a rubella vaccine that could be substituted for the current rubella vaccine, at almost zero cost, and used to immunize against rubella plus the inserted antigen. Without vaccination, the average age of becoming seropositive to rubella is about 9 years old in many parts of the world. Thus, it could be given to 1-2 year olds with a boost at 9 years old, with a high likelihood of success in immunizing against rubella as well as the foreign antigen (such as HBsAg or HIV antigen).

In one embodiment, an isolated rubella viral vector construct is disclosed that includes a rubella non-structural protein ORF with an in-frame deletion, a rubella structural protein ORF, and a heterologous antigenic insert. In one example, the in-frame deletion within the rubella non-structural protein ORF is an in-frame deletion between two NotI restriction enzyme sites. In some examples, the heterologous antigenic insert is positioned within the rubella non-structural protein ORF. In other examples, the heterologous antigenic insert is positioned within the rubella structural protein ORF.

Exemplary antigenic inserts include an HIV antigenic insert (such as a Gag antigenic insert, a gp41 antigenic insert or a gp120 antigenic insert) or a hepatitis B antigenic insert. In some examples, a Gag antigenic insert includes an antigenic polypeptide fragment with an amino acid sequence provided by SEQ ID NOs: 82-88. In some examples, a gp41 antigenic insert includes an antigenic polypeptide fragment of gp41 with an amino acid sequence provided by SEQ ID NOs: 1-22, 30, 81 or 89 and a transmembrane region of gp41 with an amino acid sequence provided by SEQ ID NOs: 25-28. In certain examples, a gp120 antigenic insert includes an amino acid sequence set forth by SEQ ID NOs: 63, 66, 67, 69, 71, 73 or 74. For example, the gp120 antigenic insert includes a variant gp120 polypeptide comprising a deletion of at least 8 consecutive residues of the fourth conserved loop (C4) between residues 423 and 433 of SEQ ID NO: 63.

Viral-like particles including the isolated viral vector construct are provided herein. Compositions comprising the viral-like particles are also provided.

Also disclosed are methods of using the disclosed isolated viral vectors to induce an immune response, such as a protective immune response, when introduced into a subject or to diagnose an HIV infection. For example, methods are provided for inhibiting HIV infection in a subject, for inducing an immune response to HIV in a subject, and for diagnosing HIV infection in a subject. Also disclosed are methods for measuring host range, testing sensitivity to neutralizing antibodies, or screening antiviral drugs, such as protease inhibitors.

A. Rubella Viral Vector Constructs

Disclosed herein are rubella viral vector constructs. In one example, an isolated rubella viral vector construct is disclosed that includes a rubella non-structural ORF with an in-frame deletion, a rubella structural protein ORF, and a heterologous antigenic insert. In some examples, an isolated rubella viral vector includes a sub genomic promoter. For example, the sub genomic promoter can control the expression of the structural proteins.

In one example, an in-frame deletion is within the rubella non-structural protein ORF. For example, the in-frame deletion is within nsP150. In one particular example, the in-frame deletion is an in-frame deletion between two NotI restriction enzyme sites located in nsP150, such as between base pairs (bp) 1685 and 2192.

In some examples, the heterologous antigenic insert is positioned within the rubella non-structural protein ORF. For example, the heterologous antigenic insert is positioned into nsP150, such as into the site of the Not I deletion (see FIG. 1A).

In other examples, the heterologous antigenic insert is positioned at either end of the three rubella structural proteins, capsid (C), E2 and E1. For example, the construct includes the Not I deletion which then provides space for an MPR insertion at either end of at least one of the three rubella structural proteins. This construct is advantageous as it allows an MPR to be attached to at least one of the rubella structural proteins which in turn permits the MPR to be accessible on the viral surface. Thus, the MPR is expressed on a lipid surface that resembles its natural milieu on the surface of HIV. In some examples, the MPR is over-expressed by being placed under control of the viral subgenomic promoter.

Four exemplary, non-limiting DNA and protein sequences for each of these constructs are indicated below. In one example, the MPR sequence is expressed at the carboxyl end of rubella capsid protein. For example, the MPR sequence (underlined) is expressed at the carboxyl end of rubella capsid protein:

(SEQ ID NO: 77)
PQGARMASTTPITMEDLQKALEAQSRALRADLAAGASQSRRPRPPRQRD

SSTSGDDSGRDSGGPRRRRGNRGRGQRRDWSRAPPPPEERQESRSQTPA

PKPSRAPPQQPQPPRMQTGRGGSAPRPELGPPTNPFQAAVARGLRPPLH

DPDTEAPTEACVTSWLWSEGEGAVFYRVDLHFTNLGTPPLDEDGRWDPA

LMYNPCGPEPPAHVVRAYNQPAGDVRGVWGKGERTYAEQDFRVGGTRWH

RLLRMPVRGLDGDSAPLPPYTTERIETRSARHPWRIRFGAPQAFLAGLL

LATVAVGTARAGLQPRADMAAPPTLPRSAQEKNEKELLELDKWASLWNW

FDITNWLWYIRLFIDASTRSARH.

In a second construct of this type, the MPR sequence (underlined) is expressed at the amino end of envelope protein E2 (MPER-E2):

(SEQ ID NO: 78)
DSAPLPPHTTERIETRSARHPWRIRFGAPQAFLAGLLLATVAVGTARAG

PRSAQEKNEKELLELDKWASLWNWFDITNWLWYIRLFIDASAGLQPRAD

MAAPPTLPQPPCAHGQHYGHHHHQLPFLGHDGHHGGTLRVGQHYRNASD

VLPGHWLQGGWGCYNLSDWHQGTHVCHTKHMDFWCVEHDRPPPATPTPL

TTAANSTTAATPATAPAPCHAGLNDSCGGFLSGCGPMRLRHGADTRCGR

LICGLSTTAQYPPTRFGCAMRWGLPPWELVVLTARPEDGWTCRGVPAHP

GARCPELVSPMGRATCSPASALWLATANALSLDHALAAFVLLVPWVLIF

MVCRRACRRRGAAAALTAVVLQGY.

In another exemplary construct, MPR is expressed at the carboxyl end of E2 (E2-MPER), as follows:

(SEQ ID NO: 79)
AGLLLATVAVGTARAGLQPRADMAAPPTLPQPPCAHGQHYGHHHHQLPF

LGHDGHHGGTLRVGQHYRNASDVLPGHWLQGGWGCYNLSDWHQGTHVCH

TKHMDFWCVEHDRPPPATPTPLTTAANSTTAATPATAPAPCHAGLNDSC

GGFLSGCGPMRLRHGADTRCGRLICGLSTTAQYPPTRFGCAMRWGLPPW

ELVVLTARPEDGWTCRGVPAHPGARCPELVSPMGRATCSPASALWLATA

NALSLDHALAAFVLLVPWVLIFMVCRRACRRRGAAAALTAVVLQGPRSA

QEKNEKELLELDKWASLWNWFDITNWLWYIRLFIDASRRRGAAAALTAV

VLQGYNPPAYGEEAFTYLCTAPGC.

In the fourth construct of this type, MPR is expressed at the amino end of envelope protein E1 (MPER-E1):

(SEQ ID NO: 80)
MVCRRACRRRGAAAALTAVVLQGYNPPAYGEAPRSAQEKNEKELLELDK

WASLWNWFDITNWLWYIRLFIDASLQGYNPPAYGEEAFTYLCTAPGCAT

QAPVPVRLAGVRFESKIVDGGCFAPWDLEATGACICEIPTDVSCEGLGA

WVPAAPCARIWNGTQRACTFWAVNAYSSGGYAQLASYFNPGGSYYKQYH

PTACEVEPAFGHSDAACWGFPTDTVMSVFALASYVQHPHKTVRVKFHTE

TRTVWQLSVAGVSCNVTTEHPFCNTPHGQLEVQVPPDPGDLVEYIMNYT

GNQQSRWGLGSPNCHGPDWASPVCQRHSPDCSRLVGATPERPRLRLVDA

DDPLLRTAPGPGEVWVTPVIGSQARKCGLHIRAGPYGHATVEMPEWIHA

HTTSDPWHPPGPLGLKFKTVRPVALPRTLAPPRNVRVTGCYQCGTPALV

EGLAPGGGNCHLTVNGEDLGAVPPGKFVTAALLNTPPPYQVSCGGESDR

ATARVIDPAAQSFTGVVYGTHTTAVSETRQTWAEWAAAHWWQLTLGAIC

ALPLAGLLACCAKCLYYLRGAIAPR*WA.

In additional examples, a deletion is made within the P150 of the rubella construct, such as in the middle in a size comparable to the Not I deletion to allow for the insertion and expression of genes coding for heterologous antigens, such as one or more HIV envelope protein. In one particular example, a deletion comparable to the Not I deletion is present in the middle of the P150 of the rubella vaccine strain RA27/3. Various heterologous antigens, including any of those described herein are inserted into either the nonstructural ORF or structural ORF in this strain known to be safe and immunogenic in humans.

For use, the disclosed vector constructs are chemically introduced into susceptible culture cells, for example, *E. coli*, for amplification and production of large amounts of the cDNA clone by methods known to those of ordinary skill in the art, including chemical introduction. In one particular example, the purified infectious clone is digested with an restriction endonuclease such as EcoRI (New England Biolabs, Beverly, Mass.) for linearization at the termination of the rubella virus cDNA sequences. The linearized plasmid is then transcribed in vitro with an RNA polymerase such as SP6 RNA polymerase, which results in production of RNA transcripts. The resulting RNA transcripts are used to transfect the cells by transfection procedures known to those skilled in the art. The cells, in turn, will produce both the native structural proteins of the rubella virus and the protein encoded by the foreign gene (such as HIV antigens, SIV antigens or HBsAgs). The replication of the RNA sequences and the expression of the encoded protein by the cells may be monitored by various means known to the ones skilled in the art. In some examples, the cells will further produce recombinant virus particles which, in turn, may be used to infect cells or organisms.

The recombinant virus particles can be recovered in quantity using any purification process known to those of skill in the art, such as a nickel (NTA-agarose) affinity chromatography purification procedure. These particles can be combined with a pharmaceutically acceptable carrier to provide a safe, effective vaccine, such as a HIV or Hepatitis B vaccine. The carrier can be oil, water, saline, phosphate buffer, polyethylene glycol, glycerine, propylene glycol, and combinations thereof, or other vehicles routinely used by the pharmaceutical industry for these purposes (as described in detail below). The vaccine is usually provided in lyophilized form and therefore is free of preservatives.

The disclosed recombinant virus particles can also be used to identify antibodies, such as antibodies within a subject. The immunogenic compositions of this disclosure can be employed to generate antibodies that recognize the antigens disclosed herein and the antigen from which the disclosed antigen was derived. The methods include administering to a subject an immunogenic composition including a disclosed antigen or administering to the subject a polynucleotide encoding a disclosed antigen to generate antibodies that recognize the disclosed antigen. The subject employed in this embodiment is one typically employed for antibody production. Mammals, such as, rodents, rabbits, goats, sheep, etc., are preferred.

The antibodies generated can be either polyclonal or monoclonal antibodies. Polyclonal antibodies are raised by injecting (for example subcutaneous or intramuscular injection) antigenic polypeptides into a suitable animal (for example, a mouse or a rabbit). The antibodies are then obtained from blood samples taken from the animal. The techniques used to produce polyclonal antibodies are extensively described in the literature. Polyclonal antibodies produced by the subjects can be further purified, for example, by binding to and elution from a matrix that is bound with the polypeptide against which the antibodies were raised. Those of skill in the art will know of various standard techniques for purification and/or concentration of polyclonal, as well as monoclonal, antibodies. Monoclonal antibodies can also be generated using techniques known in the art.

i. Wildtype and Variant gp41 Antigenic Inserts

In some examples, isolated rubella viral vectors disclosed herein include an antigenic insert that is a wildtype or variant gp41 polypeptide. In an example, an antigenic insert is a wildtype gp41 polypeptide or a fragment thereof. Exemplary sequence of wildtype gp41 polypeptides are shown on GENBANK®, for example accession number CAD23678 incorporated herein by reference in its entirety as available on Oct. 15, 2009. In other examples, a gp41 antigenic insert can include (a) an antigenic polypeptide fragment of gp41 and (b) a transmembrane spanning region of gp41.

In an example, the gp41 antigenic insert includes (a) an antigenic polypeptide fragment, such as an antigenic polypeptide fragment with the amino acid sequence set forth in SEQ ID NO:1 and is between 10 and 200 amino acids in length, such as from about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, or 145 amino acids; and (b) a transmembrane spanning gp41 region, such as a transmembrane spanning gp41 region with the amino acid sequence set forth in SEQ ID NO: 25 (in which wherein $X_1$, $X_2$ and $X_3$ are any amino acid; and $X_4$, $X_5$, and $X_6$ are any hydrophobic amino acid) and is between 22 and 40 amino acids in length, such as about 23 and 38 amino acids in length, including 24, 25, 26, 27, 28, 29, 30, 31, 32, 33, 34, 35, 36, 37, 38 amino acids.

In one example, the antigenic polypeptide includes the amino acid sequence of NEX$_1$X$_2$LLX$_3$LDKWASLWN (SEQ ID NO: 1). In this sequence, $X_1$, $X_2$ and $X_3$ are any amino acid. The antigenic epitope can include repeats of this sequence, such as one to five copies of SEQ ID NO: 1. As noted above, the antigenic peptide includes one or more antigenic epitopes, such as one or more envelope proteins of HIV-1, and, including SEQ ID NO: 1, can be from about 10 to about 200 amino acids in length, such as from about 16 to about 160 amino acids, such as from about 28 to about 150 amino acids in length, such as from about 28 to about 140 amino acids in length, including 29, 30, 35, 40, 45, 50, 55, 60, 65, 70, 75, 80, 85, 90, 95, 100, 105, 110, 120, 125, 130, 135, 140, or 145 amino acids.

In several examples, the antigenic polypeptide includes one or more of the amino acid sequences set forth below:

a) (NEQELLALDKWASLWNWFDITNWLWYIK); SEQ ID NO: 2 b) (NEQDLLALDKWASLWNWFDITNWLWYIK); SEQ ID NO: 3 c) (NEQDLLALDKWANLWNWFDISNWLWYIK); SEQ ID NO: 4 d) (NEQDLLALDKWANLWNWFNITNWLWYIR); SEQ ID NO: 5 e) (NEQELLELDKWASLWNWFDITNWLWYIK); SEQ ID NO: 6 f) (NEKDLLALDSWKNLWNWFDITNWLWYIK); SEQ ID NO: 7 g) (NEQDLLALDSWENLWNWFDITNWLWYIK); SEQ ID NO: 8 h) (NEQELLELDKWASLWNWFSITQWLWYIK); SEQ ID NO: 9 i) (NEQELLALDKWASLWNWFDISNWLWYIK); SEQ ID NO: 10 j) (NEQDLLALDKWDNLWSWFTITNWLWYIK); SEQ ID NO: 11 k) (NEQDLLALDKWASLWNWFDITKWLWYIK); SEQ ID NO: 12 l) (NEQDLLALDKWASLWNWFSITNWLWYIK); SEQ ID NO: 13 m) (NEKDLLELDKWASLWNWFDITNWLWYIK); SEQ ID NO: 14 n) (NEQEILALDKWASLWNWFDISKWLWYIK); SEQ ID NO: 15 o) (NEQDLLALDKWANLWNWFNISNWLWYIK); SEQ ID NO: 16 p) (NEQDLLALDKWASLWSWFDISNWLWYIK); SEQ ID NO: 17 q) (NEKDLLALDSWKNLWSWFDITNWLWYIK); SEQ ID NO: 18 r) (NEQELLQLDKWASLWNWFSITNWLWYIK); SEQ ID NO: 19 s) (NEQDLLALDKWASLWNWFDISNWLWYIK); SEQ ID NO: 20 t) (NEQELLALDKWASLWNWFDISNWLWYIR); SEQ ID NO: 21

-continued u)
(NEQELLELDKWASLWNWFNITNWLWYIK); SEQ ID NO: 22 v)
(PSAQEKNEKELLELDKWASLWN); SEQ ID NO: 30 w)
(QEKNEKELLELDKWASLWNWFDITNWLWYIRLFI); SEQ ID NO: 81
or x)
(PSWNWFDITNWLWYIRLDA). SEQ ID NO: 89

The antigenic polypeptide can include one of the amino acid sequences set forth as SEQ ID NOs: 2-22, 30, 81 or 89. A single copy of one of SEQ ID NOs: 2-22, 30, 81 or 89 can be included as the antigenic polypeptide. Alternatively, multiple copies of one of SEQ ID NOs: 2-22, 30, 81 or 89 can be included as the antigenic polypeptide. Thus, one, two, three, four or five copies of one of the amino acid sequences set forth as SEQ ID NOs: 2-22, 30, 81 or 89 can be included as the antigenic polypeptide.

In additional embodiments, more than one of these sequences can be included in the antigenic polypeptide. Thus, in several examples, two, three, four or five of the amino acid sequences set forth as SEQ ID NOs: 2-22, 30, 81 or 89 can be included as the antigenic polypeptide in tandem. Each amino acid sequence included in the antigenic polypeptide can be present only a single time, or can be repeated.

In some embodiments, the transmembrane spanning gp41 region includes the amino acid sequence set forth in SEQ ID NO: 25. In this sequence, $X_1$, $X_2$ and $X_3$ are any amino acid and $X_4$, $X_5$, and $X_6$ are any hydrophobic amino acid and the transmembrane spanning gp41 region is between 22 and 40 amino acids in length, such as 23, 24, 25, 26, 27, 28, 29, 30, 31, 32, 33, 34, 35, 36, 37, 38, 39 or 40 amino acids. In several examples, the antigenic polypeptide includes one or more of the amino acid sequences set forth below:

a)
(IFIMIVGGLIGLRIVFTVLSIV) SEQ ID NO: 26 b)
(LFIMIVGGLIGLRIVFTALSIV); SEQ ID NO: 27
or c)
(IFIMIVGGLVGLRIVFTALSIV) SEQ ID NO: 28

A gp41 polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the bound molecule which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as HBsAg and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

ii. Wildtype and Variant gp120 Antigenic Inserts

In some examples, isolated rubella viral vectors disclosed herein include an antigenic insert that is a wildtype or variant gp120 polypeptide. In an example, a wildtype gp120 polypeptide has an amino acid provided by SEQ ID NO: 63 or a fragment thereof. In other examples, a variant gp120 polypeptide includes a gp120 polypeptide in which at least 8 consecutive residues of the fourth conserved loop (C4) between residues 419 and 434 of gp120 according HXB2 numbering of SEQ ID NO: 63 are deleted. This deletion within the β20-21 loop of the gp120 polypeptide exposes the CD4 binding site thereby providing improved antibody binding and antibody induction. In one example, a variant gp120 polypeptide is a gp120 polypeptide in which at least 8 consecutive residues, such as between 8-12, 8-11, 8-10, or 8-9 (for example, 9, 10, 11 or 12) consecutive residues of C4 between residues 419 and 434 of gp120 of SEQ ID NO: 63 have been deleted.

In a particular example, a variant gp120 polypeptide includes a gp120 polypeptide in which residues 424-432 are deleted. Additional variant gp120 polypeptides include deletions of INMWQKVGK (residues 424-432 of SEQ ID NO: 63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63). In other embodiments, variant gp120 polypeptides include combinations of the amino and carboxyl ends between residues 419 and 434.

In some embodiments, a variant gp120 polypeptide does not include a variant in which residues 419-428 of SEQ ID NO: 63 are deleted. In other embodiments, a variant gp120 polypeptide does not include a variant in which residues 437-452 of SEQ ID NO: 63 are deleted.

Any of the disclosed variant gp120 polypeptide including deletions in C4 can also include a deletion in the V1V2 loop region (spanning from amino acids 125 to 205 of wild-type gp120, such as demonstrated in SEQ ID NO: 63); see S R Pollard and D C Wiley, *EMBO J.* 11:585-91, 1992 which is hereby incorporated by reference in its entirety.

The gp120 polypeptides disclosed herein can be chemically synthesized by standard methods, or can be produced recombinantly. An exemplary process for polypeptide production is described in Lu et al., *Federation of European Biochemical Societies Letters.* 429:31-35, 1998. They can also be isolated by methods including preparative chromatography and immunological separations.

Exemplary sequences for the amino acid sequence for full-length gp120 can be found on Genbank, EMBL and SwissProt websites. Exemplary non-limiting sequence information can be found for example, as SwissProt Accession No. P04578, (includes gp41 and gp120, initial entry Aug. 13, 1987, last modified on Jul. 15, 1999) and Genbank Accession No. AAF69493 (Oct. 2, 2000, gp120), all of which are incorporated herein by reference.

In other embodiments, the antigenic insert is a fusion protein. For example, fusion proteins are provided including a first and second polypeptide moiety in which one of the protein moieties includes a variant gp120 polypeptide such as a variant gp120 polypeptide with an amino acid sequence in which INMWQKVGK (residues 424-432 of SEQ ID NO:63), INMWQKVGKA (residues 424-433 of SEQ ID NO: 63), INMWQKVGKAM (residues 424-434 of SEQ ID NO: 63), RIKQIINMWQKVGK (residues 419-432 of SEQ ID NO: 63), IKQIINMWQKVGK (residues 420-432 of SEQ ID NO: 63), KQIINMWQKVGK (residues 421-432 of SEQ ID NO: 63), QIINMWQKVGK (residues 422-432 of SEQ ID NO: 63), or IINMWQKVGK (residues 423-432 of SEQ ID NO: 63) has been deleted. The other moiety is a heterologous protein such as a carrier protein and/or an immunogenic protein. Such fusions also are useful to evoke an immune response against gp120. In certain embodiments the gp120 polypeptides disclosed herein are covalent or non-covalent addition of toll like receptor (TLR) ligands or dendritic cell or B cell targeting moieties to produce self-adjuvanting proteins (e.g., IL-21).

In certain embodiments, a variant gp120 includes a V1V2 deletion without a beta 20-21 loop deletion with an amino acid sequence as set forth as:

```
                                             (SEQ ID NO: 63)
VPVWREATTTLFCASDAKAYDTEVHNVWATHACVPTDPNPQEVVLGNVT

ENFNMWKNNMVDQMHEDIISLWDESLKPCVKLTPLSVQACPKVSFQPIP

IHYCVPAGFAMLKCNNKTFNGSGPCTNVSTVQCTHGIRPVVSTQLLLNG

SLAEEDIVIRSENFTDNAKTIIVQLNESVVINCTRPNNNTRRRLSIGPG

RAFYARRNIIGDIRQAHCNISRAKWNNTLQQIVIKLREKFRNKTIAFNQ

SSGGDPEIVMHSFNCGGEFFYCNTAQLFNSTWNVTGGTNGTEGNDIITL

QCRIKQIINMWQKVGKAMYAPPITGQIRCSSNITGLLLTRDGGNSTETE

TEIFRPGGGDMRDNWRSELYKYKVVRIEPIGVAPTRAKR.
```

In some embodiments, a variant gp120 includes a V1V2 deletion with a beta 20-21 loop deletion with an amino acid sequence as set forth as: VPVWREATTTLFCASDAKAY-DTEVHNVWATHACVPTDPNPQEVVLGNVTE NFNM-WKNNMVDQMHEDIISLWDESLKPCVKLT-PLSVQACPKVSFQPIPIHY CVPAGFAMLKCNNKTFNGSGPCT-NVSTVQCTHGIRPVVSTQLLLNGSLAEE DIVIRSEN-FTDNAKTIIVQLNESVVINCTRPNNNTR-RRLSIGPGRAFYARRNII GDIRQAHCNISRAKWNNTLQQIVIKL-REKFRNKTIAFNQSSGGDPEIVMHSF NCGGEFFYCN-TAQLFNSTWNVTGGTNGTEGNDI-ITLQCRIKQLAMYAPPITG QIRCSSNITGLLLTRDGGNSTETETE-IFRPGGGDMRDNWRSELYKYKVVRIEP IGVAP-TRAKR (SEQ ID NO: 66). Sequences for deletion to generate gp120 variant with an amino acid sequence set forth in SEQ ID NO: 66 are shown in bold.

In other embodiments, a variant gp120 from a HIV isolate JRFL includes an amino acid sequence as set forth in SEQ ID NO: 67 and nucleic acid sequence set forth in SEQ ID NO: 68:

```
                                             (SEQ ID NO: 67)
IIHTVPPSGADPGPKRAEFKGLRRQQKQGIILLTMKTIIALSYILCLVLAQKLP

GNDNNSEFITSGFLGPLLVLQAGFFLLTRILTIPQSLDSWWTSLNFLGGSPVC

LGQNSQSPTSNHSPTSCPPICPGYRMCLRRFIIFLFILLLCLIFLLVLLDYQGML

PVCPLIPGSTTTSTGPCKTCTTPAQGNSKFPSCCCTKPTDGNCTCIPIPSSWAF

AKYLWEWASVRFSWLSLLVPFVQWFVGLSPTVWLSAIWMMWYWGPSLYS

IVSPFIPLLPIFFCLWVYIGVPVWKEATTTLFCASDAKAYDTEVHNVWATHA

CVPTDPNPQEVVLENVTEHFNMWKNNMVEQMQEDIISLWDQSLKPCVKLT

PLQACPKISFEPIPIHYCAPAGFAILKCNDKTFNGKGPCKNVSTVQCTHGIRP

VVSTQLLLNGSLAEEEVVIRSDNFTNNAKTIIVQLKESVEINCTRPNNNTRKSI

HIGPGRAFYTTGEIIGDIRQAHCNISRAKWNDTLKQIVIKLREQFENKTIVFNH

SSGGDPEIVMHSFNCGGEFFYCNSTQLFNSTWNNNTEGSNNTEGNTITLPCRI

KQLAMYAPPIRGQIRCSSNITGLLLTRDGGINENGTEIFRPGGGDMRDNWRS

ELYKYKVVKIEPLGVAPTKAKR*LVAAAFESR.
```

```
                                             (SEQ ID NO: 68)
ggattattcataccgtcccaccatcgggcgcggatcccggtccgaagcgcgcggaattcaaaggcctacgt cgacagcaaaagcaggggataattctattaaccatgaagactatcattgctttgagctacattttatgtctggttctcgctcaa aaacttcccggaaatgacaacaacagcgaattcatcacctccggcttcctgggcccctgctggtgctgcaggccggctt cttcctgctgacccgcatcctgaccatcccccagtccctggactcctggtggaccccctgaacttcctgggcggctcccc cgtgtgcctgggccagaactcccagtcccccacctccaaccactccccacctcctgccccccatctgccccggctac
```

-continued

```
cgctggatgtgcctgcgccgcttcatcatcttcctgttcatcctgctgctgtgcctgatcttcctgctggtgctgctggactac cagggcatgctgcccgtgtgcccctgatccccggctccaccaccacctccaccggccctgcaagacctgcaccacc cccgcccagggcaactccaagttcccctcctgctgctgcaccaagcccaccgacggcaactgcacctgcatccccatc ccctcctcctgggccttcgccaagtacctgtgggagtgggcctccgtgcgcttctcctggctgtccctgctggtgcccttc gtgcagtggttcgtgggcctgtcccccaccgtgtggctgtccgccatctggatgatggtactggggcccctccctgtac tccatcgtgtccccttcatcccctgctgcccatcttcttctgcctgtgggtgtacatcggggtacctgtgtggaaagaagc aaccaccactctattttgtgcatcagatgctaaagcatatgatacagaggtacataatgtttgggccacacatgcctgtgtac ccacagaccccaacccacaagaagtagtattggaaaatgtaacagaacattttaacatgtggaaaaataacatggtagaa cagatgcaggaggatataatcagtttatgggatcaaagcctaaagccatgtgtaaaattaaccccactccaggcctgtcca aagatatcctttgagccaattcccatacattattgtgccccggctggttttgcgattctaaagtgtaatgataagacgttcaat ggaaaaggaccatgtaaaaatgtcagcacagtacaatgtacacatggaattaggccagtagtatcaactcaactgctgct aaatggcagtctagcagaagaagaggtagtaattagatctgacaatttcacgaacaatgctaaaaccataatagtacagct gaaagaatctgtagaaattaattgtacaagacccaacaacaatacaagaaaaagtatacatataggaccagggagagca ttttatactacaggagaaataataggagatataagacaagcacattgtaacattagtagagcaaaatggaatgacactttaa aacagatagttataaaattaagagaacaatttgagaataaaacaatagtctttaatcactcctcaggaggggacccagaaa ttgtaatgcacagttttaattgtggaggagaattttttctactgtaattcaacacaactgtttaatagtacttggaataataatactg aagggtcaaataacactgaaggaaatactatcacactcccatgcagaataaaacagctagcaatgtatgcccctcccatc agaggacaaattagatgttcatcaaatattacagggctgctattaacaagagatggtggtattaatgagaatgggaccgag atcttcagacctggaggaggagatatgagggacaattggagaagtgaattatataaatataaagtagtaaaaattgaacca ttaggagtagcacccaccaaggcaaagagatgactagtcgcggccgctttcgaatctaga
```

In other embodiments, a variant gp120 from a HIV isolate AD8 includes an amino acid sequence as set forth in SEQ ID NO: 69 or nucleic acid sequence set forth in SEQ ID NO: 70:

(SEQ ID NO: 69)
```
IIHTVPPSGADPGPKRAEFKGLRRQQKQGIILLTMKTIIALSYILCLVLAQKLP
GNDNNSEFITSGFLGPLLVLQAGFFLLTRILTIPQSLDSWWTSLNFLGGSPVC
LGQNSQSPTSNHSPTSCPPICPGYRWMCLRRFIIFLFILLLCLIFLLVLLDYQG
MLPVCPLIPGSTTTSTGPCKTCTTPAQGNSKFPSCCCTKPTDGNCTCIPIPSSW
AFAKYLWEWASVRFSWLSLLVPFVQWFVGLSPTVWLSAIWMMWYWGPSL
YSIVSPFIPLLPIFFCLWVYIGVPVWKEATTTLFCASDAKAYDTEVHNVWAT
HACVPTDPNPQEVVLENVTENFNMWKNNMVEQMHEDIISLWDQSLKPCVK
LTPLQACPKVSFEPIPIHYCTPAGFAILKCKDKKFNGTGPCKNVSTVQCTHGI
RPVVSTQLLLNGSLAEEEVVIRSSNFTDNAKNIIVQLKESVEINCTRPNNNTR
KSIHIGPGRAFYTTGEIIGDIRQAHCNISRTKWNNTLNQIATKLKEQFGNNKTI
VFNQSSGGDPEIVMHSFNCGGEFFYCNSTQLFNSTWNFNGTWNLTQSNGTE
GNDTITLPCRIKQLAMYAPPIRGQIRCSSNITGLILTRDGGNNHNNDTETFRP
GGGDMRDNWRSELYKYKVVKIEPLGVAPTKAKR*LV.
```

(SEQ ID NO: 70)
```
ggattattcataccgtcccaccatcgggcgcggatcccggtccgaagcgcgcggaattcaaaggcctacgt cgacagcaaaagcaggggataattctattaaccatgaagactatcattgctttgagctacattttatgtctggttctcgctcaa aaacttcccggaaatgacaacaacagcgaattcatcacctccggcttcctgggcccctgctggtgctgcaggccggctt
```

-continued

```
cttcctgctgacccgcatcctgaccatcccccagtccctggactcctggtggacctccctgaacttcctgggcggctcccc cgtgtgcctgggccagaactcccagtcccccacctccaaccactcccccacctcctgcccccccatctgccccggctac cgctggatgtgcctgcgccgcttcatcatcttcctgttcatcctgctgctgtgcctgatcttcctgctggtgctgctggactac cagggcatgctgcccgtgtgcccccctgatcccggctccaccaccacctccaccggcccctgcaagacctgcaccacc cccgcccagggcaactccaagttcccctcctgctgctgcaccaagcccaccgacggcaactgcacctgcatccccatc ccctcctcctgggccttcgccaagtacctgtgggagtgggcctccgtgcgcttctcctggctgtccctgctggtgcccttc gtgcagtggttcgtgggcctgtccccaccgtgtggctgtccgccatctggatgatggtactggggcccctccctgtac tccatcgtgtccccttcatcccctgctgcccatcttcttctgcctgtgggtgtacatcggggtacctgtgtggaaagaagc aaccaccactctattttgtgcatcagatgctaaagcatatgatacagaggtacataatgtttgggccacacatgcctgtgtac ccacagaccccaacccacaagaagtagtattggaaaatgtgacagaaaattttaacatgtggaaaaataacatggtagaa cagatgcatgaggatataatcagtttatgggatcaaagcctaaagccatgtgtaaaattaacccccactccaggcctgtcca aaggtatcctttgagccaattcccatacattattgtaccccggctggttttgcgattctaaagtgtaaagacaagaagttcaat ggaacagggccatgtaaaaatgtcagcacagtacaatgtacacatggaattaggccagtagtgtcaactcaactgctgtt aaatggcagtctagcagaagaagaggtagtaattagatctagtaatttcacagacaatgcaaaaaacataatagtacagtt gaaagaatctgtagaaattaattgtacaagacccaacaacaatacaaggaaaagtatacatataggaccaggaagagca ttttatacaacaggagaaataataggagatataagacaagcacattgcaacattagtagaacaaaatggaataacactttaa atcaaatagctacaaaattaaaagaacaatttgggaataataaaacaatagtctttaatcaatcctcaggaggggacccag aaattgtaatgcacagttttaattgtggaggggaattttttctactgtaattcaacacaactgtttaatagtacttggaatttaatg gtacttggaatttaacacaatcgaatggtactgaaggaaatgacactatcacactcccatgtagaataaaacagctagcaa tgtatgcccctcccatcagaggacaaattagatgctcatcaaatattacagggctaatattaacaagagatggtggaaataa ccacaataatgataccgagacctttagacctggaggaggagatatgagggacaattggagaagtgaattatataaatata aagtagtaaaaattgaaccattaggagtagcacccaccaaggcaaaaagatgactagtc.
```

In other embodiments, a variant gp120 from a HIV isolate BaL includes an amino acid sequence as set forth in SEQ ID NO: 71 or a nucleic acid sequence as set forth in SEQ ID NO: 72:

(SEQ ID NO: 71)

IIHTVPPSGADPGPKRAEFKGLRRQQKQGIILLTMKTIIALSYILCLVL

AQKLPGNDNNSEFITSGFLGPLLVLQAGFFLLTRILTIPQSLDSWWTSLNFLG

GSPVCLGQNSQSPTSNHSPTSCPPICPGYRWMCLRRFIIFLFILLLCLIFLLVLL

DYQGMLPVCPLIPGSTTTSTGPCKTCTTPAQGNSKFPSCCCTKPTDGNCTCIP

IPSSWAFAKYLWEWASVRFSWLSLLVPFVQWFVGLSPTVWLSAIWMMWY

WGPSLYSIVSPFIPLLPIFFCLWVYIGVPVWKEATTTLFCASDAKAYDTEVHN

VWATHACVPTDPNPQEVELENVTENFNMWKNNMVEQMHEDIISLWDQSL

KPCVKLTPLQACPKISFEPIPIHYCAPAGFAILKCKDKKFNGKGPCSNVSTVQ

CTHGIRPVVSTQLLLNGSLAEEEVVIRSENFADNAKTIIVQLNESVEINCTRPN

NNTRKSIHIGPGRALYTTGEIIGDIRQAHCNLSRAKWNDTLNKIVIKLREQFG

NKTIVFKHSSGGDPEIVTHSFNCGGEFFYCNSTQLFNSTWNVTEESNNTVEN

NTITLPCRIKQLAMYAPPIRGQIRCSSNITGLLLTRDGGPEDNKTEVFRPGGG

DMRDNWRSELYKYKVVKIEPLGVAPTKAKR*LVAAAFESR.

-continued (SEQ ID NO: 72)

ggattattcataccgtcccaccatcgggcgcggatcccggtccgaagcgcgcggaattcaaaggcctacgt cgacagcaaaagcaggggataattctattaaccatgaagactatcattgctttgagctacattttatgtctggttctcgctcaa aaacttcccggaaatgacaacaacagcgaattcatcacctccggcttcctgggcccctgctggtgctgcaggccggctt cttcctgctgacccgcatcctgaccatcccccagtccctggactcctggtggacctccctgaacttcctgggcggctcccc cgtgtgcctgggccagaactcccagtcccccacctccaaccactcccccacctcctgcccccccatctgccccggctac cgctggatgtgcctgcgccgcttcatcatcttcctgttcatcctgctgctgtgcctgatcttcctgctggtgctgctggactac cagggcatgctgcccgtgtgcccccctgatccccggctccaccaccacctccaccggcccctgcaagacctgcaccacc cccgcccagggcaactccaagttcccctcctgctgctgcaccaagcccaccgacggcaactgcacctgcatccccatc ccctcctcctgggccttcgccaagtacctgtgggagtgggcctccgtgcgcttctcctggctgtccctgctggtgcccttc gtgcagtggttcgtgggcctgtcccccaccgtgtggctgtccgccatctggatgatgtggtactggggcccctccctgtac tccatcgtgtccccettcatcccectgctgcccatcttcttctgcctgtgggtgtacatcggggtacctgtgtggaaagaagc aaccaccactctattttgtgcatcagatgctaaagcatatgatacagaggtacataatgtttgggccacacatgcctgtgtac ccacagaccccaacccacaagaagtagaattggaaaatgtgacagaaaattttaacatgtggaaaaataacatggtaga acagatgcatgaggatataatcagtttatgggatcaaagcctaaagccatgtgtaaaattaactccactccaggcctgtcca aagatatcctttgagccaattcccatacattattgtgccccggctggttttgcgattctaaagtgtaaagataagaagttcaat ggaaaaggaccatgttcaaatgtcagcacagtacaatgtacacatgggattaggccagtagtatcaactcaactgctgtta aatggcagtctagcagaagaagaggtagtaattagatccgaaaatttcgcggacaatgctaaaaccataatagtacagct gaatgaatctgtagaaattaattgtacaagacccaacaacaatacaagaaaaagtatacatataggaccaggcagagcat tatatacaacaggagaaataataggagatataagacaagcacattgtaaccttagtagagcaaaatggaatgacactttaa ataagatagttataaaattaagagaacaatttgggaataaaacaatagtctttaagcattcctcaggaggggacccagaaat tgtgacgcacagttttaattgtggaggggaatttttctactgtaattcaacacaactgtttaatagtacttggaatgttactgaa gagtcaaataacactgtagaaaataacacaatcacactcccatgcagaataaaacagctagcaatgtatgcccctcccat cagaggacaaattagatgttcatcaaatattacagggctgctattaacaagagatggtggtccagaggacaacaagaccg aggtcttcagacctggaggaggagatatgagggacaattggagaagtgaattatataaatataaagtagtaaaaattgaa ccattaggagtagcacccaccaaggcaaagagatgactagtcgcggccgctttcgaatctaga.

In other embodiments, a variant gp120 from a HIV isolate IIIB includes an amino acid sequence as set forth in SEQ ID NO: 73 or a nucleic acid sequence as set forth in SEQ ID NO: 74:

(SEQ ID NO: 73)

IIHTVPPSGADPGPKRAEFKGLRRQQKQGIILLTMKTIIALSYILCLVL

AQKLPGNDNNSEFITSGFLGPLLVLQAGFFLLTRILTIPQSLDSWWTSLNFLG

GSPVCLGQNSQSPTSNHSPTSCPPICPGYRWMCLRRFIIFLFILLLCLIFLLVLL

DYQGMLPVCPLIPGSTTTSTGPCKTCTTPAQGNSKFPSCCCTKPTDGNCTCIP

IPSSWAFAKYLWEWASVRFSWLSLLVPFVQWFVGLSPTVWLSAIWMMWY

WGPSLYSIVSPFIPLLPIFFCLWVYIGVPVWKEATTTLFCASDAKAYDTEVHN

VWATHACVPTDPNPQEVVLVNVTENFNMWKNDMVEQMHEDIISLWDQSL

KPCVKLTPLSVQACPKVSFEPIPIHYCAPAGFAILKCNNKTFNGTGPCTNVST

VQCTHGIRPVVSTQLLLNGSLAEEEVVIRSVNFTDNAKTIIVQLNTSVEINCT

RPSVNFTDNAKTIIVQLNTSVEINCTRPMRQAHCNISRAKWNNTLKQIASKL

-continued
```
REQFGNNKTIIFKQSSGGDPEIVTHSFNCGGEFFYCNSTQLFNSTWFNSTWST

EGSNNTEGSDTITLPCRIKQSIAMYAPPISGQIRCSSNITGLLLTRDGGNSNNE

SEIFRPGGGDMRDNWRSELYKYKVVKIEPLGVAPTKAKR.
```

(SEQ ID NO: 74)
```
ggattattcataccgtcccaccatcgggcgcggatcccggtccgaagcgcgcggaattcaaaggcctacgt cgacagcaaaagcaggggataattctattaaccatgaagactatcattgctttgagctacattttatgtctggttctcgctcaa aaacttcccggaaatgacaacaacagcgaattcatcacctccggcttcctgggcccctgctggtgctgcaggccggctt cttcctgctgacccgcatcctgaccatccccagtccctggactcctggtggacctccctgaacttcctgggcggctcccc cgtgtgcctgggccagaactcccagtcccccacctccaaccactccccacctcctgcccccccatctgcccggctac cgctggatgtgcctgcgccgcttcatcatcttcctgttcatcctgctgctgtgcctgatcttcctgctggtgctgctggactac cagggcatgctgcccgtgtgcccctgatcccggctccaccaccacctccaccggccctgcaagacctgcaccacc cccgcccagggcaactccaagttcccctcctgctgctgcaccaagcccaccgacggcaactgcacctgcatccccatc ccctcctcctgggccttcgccaagtacctgtgggagtgggcctccgtgcgcttctcctggctgtccctgctggtgcccttc gtgcagtggttcgtgggcctgtccccaccgtgtggctgtccgccatctggatgatgtggtactggggcccctccctgtac tccatcgtgtccccttcatccctgctgcccatcttcttctgcctgtgggtgtacatcggggtacctgtgtggaaggaag caaccaccactctattttgtgcatcagatgctaaagcatatgatacagaggtacataatgtttgggccacacatgcctgtgta cccacagaccccaacccacaagaagtagtattggtaaatgtgacagaaaattttaacatgtggaaaaatgacatggtaga acagatgcatgaggatataatcagtttatgggatcaaagcctaaagccatgtgtaaaattaaccccactctcggtccaggc ctgtccaaaggtatcctttgagccaattcccatacattattgtgccccggctggttttgcgattctaaaatgtaataataagac gttcaatggaacaggaccatgtacaaatgtcagcacagtacaatgtacacatggaattaggccagtagtatcaactcaact gctgttaaatggcagtctagcagaagaagaggtagtaattagatctgtcaatttcacggacaatgctaaaaccataatagta cagctgaacacatctgtagaaattaattgtacaagacctctgtcaatttcacggacaatgctaaaaccataatagtacagc tgaacacatctgtagaaattaattgtacaagacccatgagacaagcacattgtaacattagtagagcaaaatggaataaca cttttaaaacagatagctagcaaattaagagaacaatttggaaataataaaacaataatctttaagcaatcctcaggagggg acccagaaattgtaacgcacagttttaattgtggaggggaattttctactgtaattcaacacaactgtttaatagtacttggttt aatagtacttggagtactgaagggtcaaataacactgaaggaagtgacacaatcaccctcccatgcagaataaaacaatc gatagcaatgtatgcccctcccatcagtggacaaattagatgttcatcaaatattacagggctgctattaacaagagatggt ggtaatagcaacaatgagtccgagatcttcagacctggaggaggagatatgagggacaattggagaagtgaattatata aatataaagtagtaaaaattgaaccattaggagtagcacccaccaaggcaaagagataa.
```

A gp120 polypeptide can be covalently linked to a carrier, which is an immunogenic macromolecule to which an antigenic molecule can be bound. When bound to a 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300. Exemplary sequences of wildtype CTL epitopes are publicly available such as those provided on the World Wide Web address hiv.lan1.gov/content/immunology/tables/ctl_summary.html which is incorporated herein by reference in its entirety as available on Oct. 15, 2010. In some examples, a CTL epitope is a CTL epitope of Gag listed in Tables 1 and 2 below.

TABLE 1

CTL epitope sequence table for SIV-Gag epitopes.

| Name | MHC Class I or Class II | Gag Epitope | Residues | Location | Sequence | SEQ ID NO: |
|---|---|---|---|---|---|---|
| D | A01 | CM9 | 181-189 | p27 gag | CTPYDINQM | 92 |
| B | A02 | GY9 | 71-79 | P17MA | GSENLKSLY | 93 |
| A | $DP_{B1-06}$ | KP11 | 59-70 | P17MA | KILSVLAPLVP | 94 |
| C | $DR_{B-W606}$ | TE15/KT15 | 97-111 | | TEEAKQIVQRHLVVET | 95 |
| E | $DR_{B1-0306}$ | ME11 | 200-210 | p27 gag | MQIIRDIINEE | 96 |

TABLE 2

CTL epitope sequence table for SIV-Gag epitopes.

| Epitope | Protein | FIXB2 location | Subtype | SEQ ID NO: |
|---|---|---|---|---|
| TRANSPTRR | Gag_Pol_TF | 21-29 | B | 97 |
| NSPTRREL | Gag_Pol_TF | 24-31 | B | 98 |
| PTRRELQVW | Gag_Pol_TF | 26-34 | B | 99 |
| PTSRELQVW | Gag_Pol_TF | 26-34 | A1 | 100 |
| AGAERQGTL | Gag_Pol_TF | 44-52 | C | 101 |
| FSFPQITLW | Gag_Pol_TF | 54-6 | B | 102 |

In some examples, an antigenic polypeptide includes one or more of CTL epitopes of Gag, such as one or more of the epitopes listed in Table 1 or 2. In some examples, an antigenic polypeptide includes one or more of the amino acid sequences set forth by SEQ ID NOs: 92-102. The antigenic epitope can include repeats of any one of these sequences, such as at least two repeats, such as between two to ten copies, such as three to five copies, such as one, two, three, four, five, six, seven, eight, nine or ten copies of SEQ ID NOs: 92-102 or combinations thereof.

In some examples, an antigenic polypeptide includes the amino acid sequence FQALSEGCTPYDIN-QMLNCVGDHQAAMQIIRDIINEEA (SEQ ID NO: 83) or REGSQKILSVLAPLVPTGSENLKSLYN-TVSVIWSIHAED (SEQ ID NO: 82). For example, the isolated rubella viral vector includes a Gag antigenic insert including the amino acids FQALSEGCTPYDIN-QMLNCVGDHQAAMQIIRDIINEEA (SEQ ID NO: 83). In some examples, the Gag antigenic insert includes the amino acids LPLSPRTLNAWVKLIEEKKFGAEVVPG (residues 1 to 27 of SEQ ID NO: 84). In additional examples, the Gag antigenic insert includes the amino acids SQKILSVLAPL (residues 4-14 of SEQ ID NO: 82). In some examples, the antigenic insert includes a Gag antigenic insert, comprising the amino acids GSENLKSLYNT (residues 4-14 of SEQ ID NO: 88).

The antigenic epitope can include repeats of any one of these sequences, such as at least two repeats, such as between two to ten copies, such as three to five copies, such as one, two, three, four, five, six, seven, eight, nine or ten copies of SEQ ID NOs: 82-88 or combinations thereof (e.g., one or more copies of FQALSEGCTPYDINQMLNCVGDHQAAMQIIRDIINEEA (SEQ ID NO: 83); LPLSPRTLNAWVKLIEEKKFGAEVVPG (residues 1 to 27 of SEQ ID NO: 84). SQKILSVLAPL (residues 4-14 of SEQ ID NO: 82); or GSENLKSLYNT (residues 4-14 of SEQ ID NO: 88)).

In several examples, the antigenic polypeptide includes one or more of the amino acid sequences set forth below:

(SEQ ID NO: 82)
REGSQKILSVLAPLVPTGSENLKSLYNTVSVIWSIHAED;

(SEQ ID NO: 83)
FQALSEGCTPYDINQMLNCVGDHQAAMQIIRDIINEEA;

(SEQ ID NO: 84)
LPLSPRTLNAWVKLIEEKKFGAEVVPGFQALSEGCTPYDINQMLNCV

GDHQAAMQIIRDIINEEA;

(SEQ ID NO: 85)
LPLSPRTLNAWVKLIEEKKFGAEVVPGFQALSEGCTPYDINQMLNCV

GDHQAAMQIIRDIINEEATRSQKILSVLAPLVPT;

(SEQ ID NO: 86)
LPLSPRTLNAWVKLIEEKKFGAEVVPGFQALSEGCTPYDINQMLNCV

GDHQAAMQIIRDIINEEATRTGSENLKSLYNT;

(SEQ ID NO: 87)
LPLSPRTLNAWVKLIEEKKFGAEVVPGFQALSEGCTPYDINQMLNCV

GDHQAAMQIIRDIINEEATRHTEEAKQIVQRHLVVETGTT;

(SEQ ID NO: 88)
VPTGSENLKSLYNTVTRVKHTEEAKQIVQRHLVVETGTTSDAFQALS

EGCTPYDINQMLNCVGDHQAAMQIIRDIINEEA;

-continued (SEQ ID NO: 90)
LDRFGLAESLLENKEGSQKILSVLAPLVPTGSENLKSLYNTVTRVKHT

EEAKQIVQRHLVVETGTTETSDAFQALSEGCTPYDINQMLNCVGDHQA

AMQIIRDIINEEA;
or (SEQ ID NO: 91)
LDRFGLAESLLENKEGSQKILSVLAPLVPTGSENLKSLYNTVTRVKHT

EEAKQIVQRHLVVETGTTETRLPLSPRTLNAWVKLIEEKKFGAEVVPG

FQALSEGCTPYDINQMLNCVGDHQAAMQIIRDIINEEA.

The antigenic polypeptide can include one of the amino acid sequences set forth as SEQ ID NOs: 82-88, 90 and 91. A single copy of one of SEQ ID NOs: 82-88, 90 and 91 can be included as the antigenic polypeptide. Alternatively, multiple copies of one of SEQ ID NOs: 82-88, 90 and 91 can be included as the antigenic polypeptide. Thus, one, two, three, four, five, six, seven, eight, nine or more copies of one of the amino acid sequences set forth as SEQ ID NOs: 82-88, 90 and 91 can be included as the antigenic polypeptide.

In additional embodiments, more than one of these sequences can be included in the antigenic polypeptide. Thus, in several examples, two, three, four or five of the amino acid sequences set forth as SEQ ID NOs: 82-88, 90 and 91, can be included as the antigenic polypeptide in tandem. Each amino acid sequence included in the antigenic polypeptide can be present only a single time, or can be repeated.

In some examples, an antigenic polypeptide includes an amino acid sequence set forth as (SEQ ID NO: 103)
LDRFGLAESLLENKEGCQKILSVLAPLVPTGSENLKSLYNTVCVIWCIHA

EEKVKHTEEAKQIVQRHLVVETGTTETMPKTSRPTAPSSGRGGNYPVQQI

GGNYVHLPLSPRTLNAWVKLIEEKKFGAEVVPGFQALSEGCTPYDINQML

NCVGDHQAAMQIIRDIINEEA and is encoded by a nucleic acid sequence set forth as (SEQ ID NO: 56)
ATTAGATAGATTTGGATTAGCAGAAAGCCTGTTGGAGAACAAAGAAGGAT

GTCAAAAAATACTTTCGGTCTTAGCTCCATTAGTGCCAACAGGCTCAGAA

AATTTAAAAAGCCTTTATAATACTGTCTGCGTCATCTGGTGCATTCACGC

AGAAGAGAAAGTGAAACACACTGAGGAAGCAAAACAGATAGTGCAGAGAC

ACCTAGTGGTGGAAACAGGAACAACAGAAACTATGCCAAAAACAAGTAGA

CCAACAGCACCATCTAGCGGCAGAGGAGGAAATTACCCAGTACAACAAAT

AGGTGGTAACTATGTCCACCTGCCATTAAGCCCGAGAACATTAAATGCCT

GGGTAAAATTGATAGAGGAAAAGAAATTTGGAGCAGAAGTAGTGCCAGGA

TTTCAGGCACTGTCAGAAGGTTGCACCCCCTATGACATTAATCAGATGTT

AAATTGTGTGGGAGACCATCAAGCGGCTATGCAGATTATCAGAGATATTA

TAAACGAGGAGGCTG.

An antigenic insert of a CTL epitope of a Gag polypeptide can be covalently linked to a carrier, which is an immunogenic macromolecule to which an antigenic molecule can be bound. When bound to a carrier, the bound polypeptide becomes more immunogenic. Carriers are chosen to increase the immunogenicity of the bound molecule and/or to elicit higher titers of antibodies against the bound molecule which are diagnostically, analytically, and/or therapeutically beneficial. Covalent linking of a molecule to a carrier can confer enhanced immunogenicity and T cell dependence (see Pozsgay et al., *PNAS* 96:5194-97, 1999; Lee et al., *J. Immunol.* 116:1711-18, 1976; Dintzis et al., *PNAS* 73:3671-75, 1976). Useful carriers include polymeric carriers, which can be natural (for example, polysaccharides, polypeptides or proteins from bacteria or viruses), semi-synthetic or synthetic materials containing one or more functional groups to which a reactant moiety can be attached. Bacterial products and viral proteins (such as HBsAg and core antigen) can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include bacterial wall proteins and other products (for example, streptococcal or staphylococcal cell walls and lipopolysaccharide (LPS)).

iv. Wildtype and Variant HBsAgs

In an example, a disclosed isolated rubella viral vector includes a wildtype or variant HBsAg. Suitable amino acid sequences for HBsAg are known in the art, and are disclosed, for example, in PCT Publication No. WO 2002/079217, which is incorporated herein by reference. Additional sequences for hepatitis B surface antigen can be found, for example, in PCT Publication No. 2004/113369 and PCT Publication No. WO 2004/09849. An exemplary HBsAg amino acid sequence, and the sequence of a nucleic acid encoding HBsAg, is shown in Berkower et al., *Virology* 321: 74-86, 2004, which is incorporated herein by reference in its entirety. An amino acid sequence of an exemplary HBsAg is set forth as follows:

(SEQ ID NO: 31)
EFITSGFLGPLLVLQAGFFLLTRILTIPQSLDSWWTSLNFLGGSPVCLG

QNSQSPTSNHSPTSCPPICPGYRWMCLRRFIIFLFILLLCLIFLLVLLD

YQGMLPVCPLIPGSTTTSTGPCKTCTTPAQGNSKFPSCCCTKPTDGNCT

CISIPSSWAFAKYLWEWASVRFSWLSLLVPFVQWFVGLSPTVWLSAIWM

MWYWGPSLYSIVSPFIPLLPIFFCLWVYIG.

Naturally occurring variants of HBsAg are found in other hepadnaviruses and also self assemble. These include: woodchuck hepatitis, ground squirrel hepatitis and duck hepatitis virus variants. Any of these naturally occurring HBsAg variants can be included within the disclosed constructs.

By itself, HBsAg assembles into approximately 22 nm virus-like particles. When expressed together with an HIV-1 antigenic epitope, the HBsAg fusion proteins assemble spontaneously and efficiently into virus-like particles (see Berkower et al., *Virology* 321: 75-86, 2004, which is incorporated herein by reference). Without being bound by theory, the multimeric form expresses the one or more antigenic epitopes at the lipid-water interface. These epitopes can be used to induce an immune response, such as to induce the production of neutralizing antibodies.

The preparation of HBsAg is well documented. See, for example, Harford et al. (1983) *Develop. Biol. Standard* 54:125; Greg et al. (1987) *Biotechnology* 5:479; EP-A-0 226 846; and EP-A-0 299 108.

Fragments and variants of HBsAgs as disclosed herein are fragments and variants that retain the ability to spontaneously assemble into virus-like particles. By "fragment" of an HBsAg is intended a portion of a nucleotide sequence encoding a HBsAg, or a portion of the amino acid sequence of the protein. By "homologue" or "variant" is intended a nucleotide or amino acid sequence sufficiently identical to the reference nucleotide or amino acid sequence, respectively.

It is recognized that the gene or cDNA encoding a polypeptide can be considerably mutated without materially altering one or more the polypeptide's functions. The genetic code is well known to be degenerate, and thus different codons encode the same amino acids. Even where an amino acid substitution is introduced, the mutation can be conservative and have no material impact on the essential functions of a protein (see Stryer, *Biochemistry* 4th Ed., W. Freeman & Co., New York, N.Y., 1995). Part of a polypeptide chain can be deleted without impairing or eliminating all of its functions. Sequence variants of a protein, such as a 5' or 3' variant, can retain the full function of an entire protein. Moreover, insertions or additions can be made in the polypeptide chain for example, adding epitope tags, without impairing or eliminating its functions (Ausubel et al., *Current Protocols in Molecular Biology*, Greene Publ. Assoc. and Wiley-Intersciences, 1998). Specific substitutions include replacing one or more transmembrane spanning domains of HBsAg with a gp41 transmembrane spanning domain, such as replacing the first domain and/or third domain of HBsAg with a gp41 transmembrane spanning domain. Other modifications that can be made without materially impairing one or more functions of a polypeptide include, for example, in vivo or in vitro chemical and biochemical modifications or the incorporation of unusual amino acids. Such modifications include, for example, acetylation, carboxylation, phosphorylation, glycosylation, ubiquitination, labeling, such as with radionucleides, and various enzymatic modifications, as will be readily appreciated by those well skilled in the art. A variety of methods for labeling polypeptides and labels useful for such purposes is well known in the art, and includes radioactive isotopes such as $^{125}I$ or $^{3}H$, ligands that bind to or are bound by labeled specific binding partners (such as antibodies), fluorophores, chemiluminescent agents, enzymes, and antiligands or crosslinkers to produce dimers or multimers.

Functional fragments and variants of HBsAg include those fragments and variants that are encoded by nucleotide sequences that retain the ability to spontaneously assemble into virus-like particles. Functional fragments and variants can be of varying length. For example, a fragment may consist of 10 or more, 25 or more, 50 or more, 75 or more, 100 or more, or 200 or more amino acid residues of a HBsAg amino acid sequence.

A functional fragment or variant of HBsAg is defined herein as a polypeptide that is capable of spontaneously assembling into virus-like particles and/or self-aggregating into stable multimers. This includes, for example, any polypeptide six or more amino acid residues in length that is capable of spontaneously assembling into virus-like particles. Methods to assay for virus-like particle formation are well known in the art (see, for example, Berkower et al. (2004) *Virology* 321:75-86, herein incorporated by reference in its entirety).

"Homologues" or "variants" of a HBsAg are encoded by a nucleotide sequence sufficiently identical to a nucleotide sequence of hepatitis B surface antigen, examples of which are described above. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98% or 99% sequence identity over its full length as compared to a reference sequence, for example using the NCBI Blast 2.0 gapped BLAST set to default parameters. Alignment may also be performed manually by inspection. For comparisons of amino acid sequences of greater than about 30 amino acids, the Blast 2 sequences function is employed using the default BLOSUM62 matrix set to default parameters (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). In one embodiment, the HBsAg protein is at least about 85%, at least about 90%, at least about 95%, at least about 96%, at least about 97%, at least about 98%, at least about 99% identical to the polypeptide set forth as SEQ ID NO: 31.

One or more conservative amino acid modifications can be made in the HBsAg amino acid sequence, whether an addition, deletion or modification, that does not substantially alter the 3-dimensional structure of the polypeptide. For example, a conservative amino acid substitution does not affect the ability of the HBsAg polypeptide to self-aggregate into stable multimers. HBsAg proteins having deletions of a small number of amino acids, for example, less than about 20% (such as less than about 18%, less than about 15%, less than about 10%, less than about 8%, less than about 5%, less than about 2%, or less than about 1%) of the total number of amino acids in the wild type HBsAg protein can also be included in the fusion proteins described herein. The deletion may be a terminal deletion, or an internal deletion, so long as the deletion does not substantially affect the structure or aggregation of the fusion protein.

In certain embodiments, a variant HBsAg can include a linker sequence. This peptide is a short amino acid sequence providing a flexible linker that permits attachment of an antigenic polypeptide, such as an HIV antigen (such as a gp41 or gp120 polypeptide), without disruption of the structure, aggregation (multimerization) or activity of the self-aggregating polypeptide component. Typically, a linear linking peptide consists of between two and 25 amino acids. Usually, the linear linking peptide is between two and 15 amino acids in length. In one example, the linker polypeptide is two to three amino acids in length, such as a serine and an arginine, or two serine residues and an arginine residue, or two arginine residues and a serine residue.

In other examples, the linear linking peptide can be a short sequence of alternating glycines and prolines, such as the amino acid sequence glycine-proline-glycine-proline. A linking peptide can also consist of one or more repeats of the sequence glycine-glycine-serine. Alternatively, the linear linking peptide can be somewhat longer, such as the glycine (4)-serine spacer described by Chaudhary et al., *Nature* 339: 394-397, 1989.

Directly or indirectly adjacent to the remaining end of the linear linking peptide (that is, the end of the linear linking peptide not attached to the self-aggregating polypeptide component of the fusion protein) is a polypeptide sequence including at least one antigenic epitope of HIV-1, such as an epitope of gp41, such as at least one antigenic epitope of the membrane proximal region. The antigenic polypeptide can be a short peptide sequence including a single epitope. For example the antigenic polypeptide can be a sequence of amino acids as short as eight or nine amino acids, sufficient in length to provide an antigenic epitope in the context of presentation by a cellular antigen presenting complex, such as the major histocompatibility complex (MHC). The antigenic polypeptide can also be of sufficient in length to induce antibodies, such as neutralizing antibodies. Larger peptides, in excess of 10 amino acids, 20 amino acids or 30 amino acids are also suitable antigenic polypeptides, as are much larger polypeptides provided that the antigenic polypeptide does not disrupt the structure or aggregation of the HBsAg polypeptide component.

In some examples, the variant HBsAg includes one or more epitopes of the envelope protein of HIV-1 or major CTLs of HIV or SIV Gag, and is about 20 to about 200 amino acids in length, such as about 25 to about 150 amino acids in length, such as about 25 to about 100 amino acids in length. In several additional examples, the antigenic polypeptide includes one or more antigenic epitopes of HIV-1 gp41, such as the membrane proximal region (MPR) of gp41.

Exemplary sequences for HIV-1, as well as the amino acid sequence for full-length gp41 and gp120 and CTLs of Gag can be found on Genbank, EMBL and SwissProt websites. Exemplary non-limiting sequence information can be found for example, as SwissProt Accession No. P04578, (includes gp41 and gp120, initial entry Aug. 13, 1987, last modified on Jul. 15, 1999); Genbank Accession No. HIVHXB2CG (full length HIV-1, including RNA sequence and encoded proteins, Oct. 21, 2002); Genbank Accession No. CAD23678 (gp41, Apr. 15, 2005); Genbank Accession No. CAA65369 (Apr. 18, 2005); all of which are incorporated herein by reference. Similar information is available for HIV-2.

Suitable Env proteins are known in the art and include, for example, gp160, gp120, gp41, and gp140. Any clade of HIV is appropriate for antigen selection, including HIV clades A, B, C, and the like. HIV Gag, Pol, Nef and/or Env proteins from HIV clades A, B, C, as well as nucleic acid sequences encoding such proteins and methods for the manipulation and insertion of such nucleic acid sequences into vectors, are known (see, for example, HIV Sequence Compendium, Division of AIDS, National Institute of Allergy and Infectious Diseases, 2003, HIV Sequence Database (on the world wide web at hiv-web.lanl.gov/content/hiv-db/mainpage.html), Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Association. Exemplary Env polypeptides, for example, corresponding to clades A, B and C are represented by the sequences of Genbank® Accession Nos. U08794, K03455 and AF286227, respectively.

Variant HBsAgs can form a self-aggregating multimeric spherical or rod-shaped structure upon expression in a host cell. Similarly, the variant HBsAgs can assemble spontaneously (self-aggregate) when placed in suspension in a solution of physiological pH (for example, a pH of about 7.0 to 7.6). Thus, in the present disclosure, wherever a single or monomeric variant HBsAg is disclosed, polymeric forms are also considered to be described.

In some embodiments, an isolated rubella viral vector includes a variant HBsAg with one or more transmembrane domains of the HBsAg replaced with a gp41 antigenic insert. The gp41 antigenic insert can include (a) an antigenic polypeptide fragment of gp41 and (b) a transmembrane spanning region of gp41. In an example, the gp41 antigenic insert includes (a) an antigenic polypeptide fragment, such as an antigenic polypeptide fragment with the amino acid sequence set forth in SEQ ID NO:1 and is between 28 and 150 amino acids in length and (b) a transmembrane spanning gp41 region, such as a transmembrane spanning gp41 region with the amino acid sequence set forth in SEQ ID NO: 25 (in which wherein $X_1$, $X_2$ and $X_3$ are any amino acid; and $X_4$, $X_5$, and $X_6$ are any hydrophobic amino acid) and is between 22 and 40 amino acids in length.

In one example, the antigenic polypeptide includes the amino acid sequence of NEX$_1$X$_2$LLX$_3$LDKWASLWN (SEQ ID NO: 1). In this sequence, $X_1$, $X_2$ and $X_3$ are any amino acid. The antigenic epitope can include repeats of this sequence, such as one to five copies of SEQ ID NO: 1. As noted above, the antigenic peptide includes one or more epitopes of the envelope protein of HIV-1, and, including SEQ ID NO: 1, about 10 to about 200 amino acids in length, such as from about 16 to about 160 amino acids, such as from about 28 to about 150 amino acids in length, such as from about 28 to about 140 amino acids in length.

In several examples, the antigenic polypeptide includes one or more of the amino acid sequences set forth in SEQ ID NOs: 2-22, 30, 81 or 89. A single copy of one of SEQ ID NOs: 2-22, 30, 81 or 89 can be included as the antigenic polypeptide. Alternatively, multiple copies of one of SEQ ID NOs: 2-22, 30, 81 or 89 can be included as the antigenic polypeptide. Thus, one, two, three, four or five copies of one of the amino acid sequences set forth as SEQ ID NOs: 2-22, 30, 81 or 89 can be included as the antigenic polypeptide.

In additional embodiments, more than one of these sequences can be included in the antigenic polypeptide. Thus, in several examples, two, three, four or five of the amino acid sequences set forth as SEQ ID NOs: 2-22, 30, 81 and 89 can be included as the antigenic polypeptide in tandem. Each amino acid sequence included in the antigenic polypeptide can be present only a single time, or can be repeated.

The HBsAg variants can include one or more transmembrane spanning domains that include one of the amino acid sequences set forth as SEQ ID NOs: 26-28. A single gp41 transmembrane can be included in the variant HBsAg. Alternatively, multiple gp41 transmembrane domains with amino acid sequences set forth as SEQ ID NOs: 26-28 can be included within the variant HBsAg. Thus, one, two, three, four or five gp41 transmembrane domains with one of the amino acid sequences set forth as SEQ ID NOs: 26-28 can be included in the variant HBsAg.

In one particular embodiment, an isolated rubella viral construct includes a variant HBsAg in which the first transmembrane spanning domain of the HBsAg is replaced by a gp41 antigenic insert. For example, the gp41 antigenic insert replaces at least the first 29 amino acid residues of SEQ ID NO:20, for example amino acid residues 1-35 of SEQ ID NO: 31. In another example, the gp41 antigenic insert replaces amino acid residues 1-32 of SEQ ID NO: 31. In yet another example, the gp41 antigenic insert replaces amino acid residues 1-29 of SEQ ID NO: 31. In a particular example, an isolated construct includes a variant HBsAg in which the first transmembrane spanning domain of the HBsAg is replaced by a gp41 antigenic insert that has the amino acid sequence set forth as SEQ ID NO: 29.

In another particular embodiment, an isolated construct includes a variant HBsAg in which the third transmembrane spanning domain of the HBsAg is replaced by a gp41 antigenic insert. For example, the gp41 antigenic insert replaces at least 29 amino acids residues of SEQ ID NO: 31, for example amino acid residues 150-190 of SEQ ID NO: 31. In another example, the gp41 antigenic insert replaces amino acid residues 153-187 of SEQ ID NO: 31. In yet another example, the gp41 antigenic insert replaces amino acid residues 156-185 of SEQ ID NO: 31. In a particular example, an isolated construct includes a variant HBsAg in which the third transmembrane spanning domain of the HBsAg is replaced by a gp41 antigenic insert has the amino acid sequence set forth as SEQ ID NO: 59.

In an even more particular embodiment, an isolated rubella viral construct includes a variant HBsAg in which more than one transmembrane spanning domains of HBsAg have been replaced with an antigenic insert. In one example, an isolated construct includes a variant HBsAg in which the first and the third transmembrane spanning domains of the HBsAg are replaced by a gp41 antigenic insert. For example, the gp41 antigenic insert replaces amino acid residues 1-35 and 150-190 of SEQ ID NO: 31. In another example, the gp41 antigenic insert replaces amino acid residues 1-32 and 153-187 of SEQ ID NO: 31. In yet another example, the gp41 antigenic insert replaces amino acid residues 1-29 and 156-185 of SEQ ID NO: 31. In a particular example, an isolated construct including a variant HBsAg in which the third transmembrane spanning domain of the HBsAg is replaced by a gp41 antigenic insert has the amino acid sequence set forth as:

(SEQ ID NO: 59)
MKTIIALSYIFCLVFAQDLPGNDNNSEFITSGFLGPLLVLQAGFFLLTR

ILTIPQSLDSWWTSLNFLGGSPVCLGQNSQSPTSNHSPTSCPPICPGYR

WMCLRRFIIFLFILLLCLIFLLVLLDYQGMLPVCPLIPGSTTTSTGPCK

TCTTPAQGNSKFPSCCCTKPTDGNCTCININEKELLELDKWASLWNWFD

ITNWLWYIRLFIMIVGGLIGLRIVFAVLSIVVGLSPTVWLSAIWMMWYW

GPSLYSIVSPFIPLLPIFFCLWVYIG.

In one example of an isolated construct, in which the first transmembrane domain of HBsAg is replaced with the MPR and transmembrane domain of gp41 has the amino acid sequence set forth as:

(SEQ ID NO: 29)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIP

IPSSWAFAKYLWEWASVRFSWLSLLVPFVQWFVGLSPTVWLSAIWMMWYW

GPSLYSIVSPFIPLLPIFFCLWVYIG.

In one example of the isolated construct, the third transmembrane domain of HBsAg is replaced with the MPR and transmembrane domain of gp41 has the amino acid sequence set forth as:

(SEQ ID NO: 59)
MKTIIALSYIFCLVFAQDLPGNDNNSEFITSGFLGPLINLQAGFFLLTR

ILTIPQSLDSWWTSLNFLGGSPVCLGQNSQSPTSNHSPTSCPPICPGYR

WMCLRRFIIFLFILLLCLIFLLVLLDYQGMLPVCPLIPGSTTTSTGPCK

TCTTPAQGNSKFPSCCCTKPTDGNCTCININEKELLELDKWASLWNWFD

ITNWLWYIRLFIMIVGGLIGLRIVFAVLSIVVGLSPTVWLSAIWMMWYW

GPSLYSIVSPFIPLLPIFFCLWVYIG.

In an example, an isolated construct is provided in which the first transmembrane domain and third domain of HBsAG is each replaced with the MPR and transmembrane domain of gp41 and has the amino acid sequence set forth as:

(SEQ ID NO: 58)
MKTIIALSYIFCLVFAQDLPGNDNNSEFNEKELLELDKWASLWNWFDITN

WLWYIRLFIMIVGGLIGLRIVFAVLSIPQSLDSWWTSLNFLGGSPVCLGQ

NSQSPTSNHSPTSCPPICPGYRWMCLRRFIIFLFILLLCLIFLLVLLDYQ

GMLPVCPLIPGSTTTSTGPCKTCTTPAQGNSKFPSCCCTKPTDGNCTCIP

INEKELLELDKWASLWNWFDITNWLWYIRLFIMIVGGLIGLRIVFAVLSI

VVGLSPTVWLSAIWMMWYWGPSLYSIVSPFIPLLPIFFCLWVYIG.

In one example, an isolated construct is provided in which the first transmembrane domain of HBsAg is replaced with the MPR and transmembrane domain of gp41 and an additional MPR is inserted just proximal to the third membrane spanning domain of HBsAg. In another example, an isolated construct is provided in which multiple MPRs are inserted within the HBsAg, such as two, three, four or more MPRs are inserted just proximal to the third membrane spanning domain of HBsAg. In yet another example, an isolated construct is provided in which a MPR and transmembrane domain of gp41 is inserted following the fourth HBsAg membrane spanning domain.

The variant HBsAg can optionally include additional elements, such as a leader sequence or a suitable T cell epitope. Generally, a T cell epitope is about eight to about ten amino acids in length, such as about nine amino acid in length, and binds major histocompatibility complex (MHC), such as HLA 2, for example, HLA 2.2. Examples of suitable T cell epitopes include, but are not limited to, ASLWNWFNITNWLWY (SEQ ID NO: 32) and IKLFIMIVGGLVGLR (SEQ ID NO: 33).

The variant HBsAg may also include a CAAX (SEQ ID NO: 34) sequence, for isoprenyl addition in vivo. In this sequence, C is cysteine, A is an aliphatic amino acid and X is any amino acid. The X residue determines which isoprenoid will be added to the cysteine. When X is a methionine or serine, the farnesyl-transferase transfers a farnesyl, and when X is a leucine or isoleucine, the geranygeranyl-transferase I transfers a geranylgeranyl group. In general, aliphatic amino acids have protein side chains containing only carbon or hydrogen atoms. Aliphatic amino acids include proline (P), glycine (G), alanine (A), valine (V), leucine (L), and isoleucine (I), presented in order from less hydrophobic to more hydrophobic. Although methionine has a sulphur atom in its side-chain, it is largely non-reactive, meaning that methionine effectively substitutes well with the true aliphatic amino acids.

B. Therapeutic Methods and Pharmaceutical Compositions

The disclosed isolated rubella viral vector constructs including antigenic inserts, such as HIV polypeptides (e.g., Gag, gp41 or gp120) or HBsAgs polypeptides (natural and recombinant) described herein can be used to produce pharmaceutical compositions, including compositions suitable for prophylactic and/or therapeutic administration. These compositions can be used to induce an immune response to HIV, SIV or Hepatitis B, such as a protective immune response. However, the compositions can also be used in various assays, such as in assays designed to detect an HIV-1 or Hepatitis B infection.

The disclosed isolated rubella viral constructs including can be administered to a subject in order to generate an immune response to HIV-1, SIV or Hepatitis B. In one example, the immune response is a protective immune response. Thus, the constructs disclosed herein can be used in a vaccine, such as a vaccine to inhibit subsequent infection with HIV, SIV or Hepatitis B. In some examples the disclosed constructs are administered as a virus like particle.

A therapeutically effective amount of a rubella viral construct, a virus-like particle including this construct, or a composition including the construct or virus-like particle can be administered to a subject to prevent, inhibit or to treat a condition, symptom or disease, such as AIDS. As such, the constructs can be administered as vaccines to prophylactically or therapeutically induce or enhance an immune response. For example, the pharmaceutical compositions described herein can be administered to stimulate a protective immune response against HIV, such as a HIV-1, SIV or Hepatitis B. In some examples, a disclosed composition is administered to a subject either alone or in combination with other HIV, SIV or Hepatitis B therapeutic agents. A single administration can be utilized to prevent or treat an HIV or Hepatitis B infection, or multiple sequential administrations can be performed.

In exemplary applications, compositions are administered to a subject infected with HIV or Hepatitis B, or likely to be exposed to an infection, in an amount sufficient to raise an immune response to HIV or Hepatitis B. Administration induces a sufficient immune response to reduce viral load, to prevent or lessen a later infection with the virus, or to reduce a sign or a symptom of HIV or Hepatitis B infection. Amounts effective for this use will depend upon various clinical parameters, including the general state of the subject's health, and the robustness of the subject's immune system, amongst other factors. A therapeutically effective amount of the compound is that which provides either subjective relief of one or more symptom(s) of HIV or Hepatitis B infection, an objectively identifiable improvement as noted by the clinician or other qualified observer, a decrease in viral load, an increase in lymphocyte count, such as an increase in CD4 cells, or inhibition of development of symptoms associated with infection. In one particular example, the administration of the composition will result in in vivo protein expression of the proteins encoded by the open reading frames contained in the expression vector construct. For example, the administration of the composition will result in the induction of immunity against the viruses whose proteins are encoded by the open reading frames.

The compositions can be administered by any means known to one of skill in the art (see Banga, A., "Parenteral Controlled Delivery of Therapeutic Peptides and Proteins," in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated.

In some examples, the compositions are administered in a formulation including a carrier or excipient. A wide variety of suitable excipients are known in the art, including physiological phosphate buffered saline (PBS), and the like. Optionally, the formulation can include additional components, such as aluminum hydroxylphophosulfate, alum, diphtheria $CRM_{197}$, or liposomes. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle. A particulate carrier based on a synthetic polymer has been shown to act as an adjuvant to enhance the immune response, in addition to providing a controlled release. Aluminum salts may also be used as adjuvants to produce an immune response.

In a specific example, the composition is administered as a vaccine subcutaneously at a concentration range from 102 to 104 $TCID_{50}$/person (TCID is an abbreviation for tissue culture infectious doses). For example, the vaccine is provided to the physician in a lyophilized form, reconstituted in an appropriate solvent such as deionized water or saline, and administered as a single injection.

In one embodiment, the construct is mixed with an adjuvant containing two or more of a stabilizing detergent, a micelle-forming agent, and an oil. Suitable stabilizing detergents, micelle-forming agents, and oils are detailed in U.S. Pat. No. 5,585,103; U.S. Pat. No. 5,709,860; U.S. Pat. No. 5,270,202; and U.S. Pat. No. 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly (oxy-1,2-ethanediyl; manufactured by ICI Americas, Wilmington, Del.), TWEEN 40™, TWEEN 20™, TWEEN 60™, ZWITTERGENT™ 3-12, TEEPOL HB7™, and SPAN 85™. These detergents are usually provided in an amount of approximately 0.05 to 0.5%, such as at about 0.2%. A micelle forming agent is an agent which is able to stabilize the emulsion formed with the other components such that a micelle-like structure is formed. Such agents generally cause some irritation at the site of injection in order to recruit macrophages to enhance the cellular response. Examples of such agents include polymer surfactants described by BASF Wyandotte publications, for example, Schmolka, *J. Am. Oil. Chem. Soc.* 54:110, 1977; and Hunter et al., *J. Immunol.* 129:1244, 1981, PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167, 1984. The agent can be provided in an effective amount, for example between 0.5 and 10%, or in an amount between 1.25 and 5%.

The oil included in the composition is chosen to promote the retention of the antigen in oil-in-water emulsion, such as to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, or between 2.5 and 5%. The oil should be both biodegradable and biocompatible so that the body can break down the oil over time, and so that no adverse affects, such as granulomas, are evident upon use of the oil.

An adjuvant can be included in the composition. In one example, the adjuvant is a water-in-oil emulsion in which antigen solution is emulsified in mineral oil (such as Freund's incomplete adjuvant or montanide-ISA). In one embodiment, the adjuvant is a mixture of stabilizing detergents, micelle-forming agent, and oil available under the name PROVAX® (IDEC Pharmaceuticals, San Diego, Calif.). Other examples of suitable adjuvants are listed in the terms section of this specification.

Actual methods for preparing administrable compositions will be known or apparent to those skilled in the art and are described in more detail in such publications as *Remingtons: The Science and Practice of Pharmacy*, University of the Sciences in Philadelphia, Lippincott Williams & Wilkins, Philadelphia, Pa., 21st Edition (2005). The compositions can be administered, either systemically or locally, for therapeutic treatments, such as to treat an HIV infection. In therapeutic applications, a therapeutically effective amount of the composition is administered to a subject infected with HIV, such as, but not limited to, a subject exhibiting signs or symptoms of AIDS. Single or multiple administrations of the compositions can be administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of the HIV infection without producing unacceptable toxicity to the subject.

Controlled release parenteral formulations can be made as implants, oily injections, or as particulate systems. For a broad overview of protein delivery systems, see Banga, *Therapeutic Peptides and Proteins: Formulation, Processing, and Delivery Systems*, Technomic Publishing Company, Inc., Lancaster, Pa. (1995). Particulate systems include microspheres, microparticles, microcapsules, nanocapsules, nanospheres, and nanoparticles. Microcapsules contain the therapeutic protein as a central core. In microspheres, the therapeutic agent is dispersed throughout the particle. Particles, microspheres, and microcapsules smaller than about 1 µm are generally referred to as nanoparticles, nanospheres, and nanocapsules, respectively. Capillaries have a diameter of approximately 5 µm so that only nanoparticles are administered intravenously. Microparticles are typically around 100 µm in diameter and are administered subcutaneously or intramuscularly (see Kreuter, *Colloidal Drug Delivery Systems*, J. Kreuter, ed., Marcel Dekker, Inc., New York, N.Y., pp. 219-342 (1994); Tice & Tabibi, *Treatise on Controlled Drug Delivery*, A. Kydonieus, ed., Marcel Dekker, Inc. New York, N.Y., pp. 315-339 (1992)). In one example, virus like particles are in the range of 10-30 nm.

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44 (2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (e.g., U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

C. Immunodiagnostic Reagents and Kits

In addition to the therapeutic methods provided above, any of the disclosed rubella viral constructs herein can be utilized to produce antigen specific immunodiagnostic reagents, for example, for serosurveillance. Immunodiagnostic reagents can be designed from any of the constructs including antigenic polypeptides described herein. For example, the presence of serum antibodies to HIV, SIV or Hepatitis B can be monitored using the isolated immunogens disclosed herein, such as to detect an HIV, SIV or Hepatitis B infection. Generally, the method includes contacting a sample from a subject, such as, but not limited to a blood, serum, plasma, urine or sputum sample from the subject with one or more of the variant molecules disclosed herein and detecting binding of antibodies in the sample to the variant molecule. For example, the method can include contacting a sample from a subject, such as, but not limited to a blood, serum, plasma, urine or sputum sample from the subject with one or more of the constructs disclosed herein and detecting binding of antibodies in the sample to the antigenic insert. The binding can be detected by any means known to one of skill in the art, including the use of labeled secondary antibodies that specifically bind the antibodies from the sample. Labels include radiolabels, enzymatic labels, and fluorescent labels.

Any such immunodiagnostic reagents can be provided as components of a kit. Optionally, such a kit includes additional components including packaging, instructions and various other reagents, such as buffers, substrates, antibodies or ligands, such as control antibodies or ligands, and detection reagents.

Methods are further provided for a diagnostic assay to monitor HIV-1 induced disease in a subject and/or to monitor the response of the subject to immunization by an HIV vaccine. By "HIV-1 induced disease" is intended any disease caused, directly or indirectly, by HIV. An example of an HIV-1 induced disease is acquired autoimmunodeficiency syndrome (AIDS). The method includes contacting a disclosed construct with a sample of bodily fluid from the subject, and detecting binding of antibodies in the sample to the disclosed antigens. In addition, the detection of the HIV-1 binding antibody also allows the response of the subject to immunization by a HIV vaccine to be monitored. In still other embodiments, the titer of the HIV-1 binding antibodies is determined. The binding can be detected by any means known to one of skill in the art, including the use of labeled secondary antibodies that specifically bind the antibodies from the sample. Labels include radiolabels, enzymatic labels, and fluorescent labels. In other embodiments, a disclosed construct is used to isolate antibodies present in a subject or biological sample obtained from a subject.

The provided isolated viral vectors can also be used in screening antiviral drugs. In one example, methods of screening antiviral drugs including methods of identifying protease inhibitors are disclosed. Viral inhibitory peptides correspond to the sequence of a protease target site for rubella. Inhibitory peptides contain synthetic amino acids, such as dehydroalanine, on either side of the expected cleavage site. When these groups are attacked by the active site cysteine of the protease, they react with it and form a covalent bond. This attaches irreversibly to the free SH-group of the active site of the enzyme and results in non-competitive inhibition of the protease.

In one particular example, a method of identifying protease inhibitors is provided that utilizes a disclosed rubella-GFP construct to detect the effect of protease inhibition. Typically, in the absence of a protease inhibitor, GFP is expressed well by days 3 to 7 of infection. However, when an inhibitory peptide is added, the virus fails to cleave its nonstructural protein precursor into two fragments: P150 and active RNA polymerase. Without this cleavage, no RNA transcription can occur, either of the negative strand template RNA, or of the positive strand RNA coding for the nonstructural and structural proteins. In particular, protease inhibition prevents expression of GFP linked to P150, as manifested by a loss of green fluorescence. Therefore, a protease inhibitor is identified by detecting a decrease or inhibition of GFP expression or a decrease or inhibition in expression of one or more of the rubella nonstructural and structural proteins, such as a 10%, 20%, 30% 40%, 50%, 60%, 70%, 80%, 90% or more reduction in expression. In one particular example, a method of identifying a protease inhibitor includes contacting a cell expressing one or more of the disclosed rubella-GFP viral constructs with one or more test agents and with an amount of an agent capable of inhibiting protease activity. Expression of GFP or one or more of the rubella nonstructural and/or structural proteins is subsequently measured, whereby a decrease in expression of one or more of this proteins indicates that the agent is a protease inhibitor.

Besides reducing GFP expression, protease inhibitors disrupt the localization of P150-GFP to viral replicating centers in the cytoplasm. P150-GFP preserves the normal functions of P150 and localizes correctly to sites of viral RNA synthesis as noted by P150-GFP localizing to these centers as intensely fluorescent dots in the cytoplasm. When protease is inhibited, even partially, this is detected as a reduction in replicating centers. It is believed that rubella will be just as sensitive to protease inhibitors as is HIV as both viruses work by similar mechanisms. Additionally, other alphaviruses, such as VEE, have a similar requirement for protease activation of RNA replication, and their inhibitory peptides can be designed similarly, based on the known targets for viral protease.

The disclosure is illustrated by the following non-limiting Examples.

EXAMPLES

Example 1

Materials and Methods

This example describes the materials and methods used in Example 2.

Construction of rubella expression plasmids and mutant viruses. A full length, infectious cDNA clone coding for wild type rubella of the Therien strain (GenBank accession M15240), called Robo 302, was kindly provided by Dr. Teryl Frey of Georgia State University (Pugachev et al., *J. Virol.* 71, 562-568, 1999). For the generation of pRubΔNot 1, Robo 302 was digested with Not I and re-ligated, resulting in deletion of a 507 bp fragment from the non-structural region (bp 3661-4168 of the plasmid), without disruption of the reading frame (FIG. 1). For the generation of pRubΔNot 1-GFP, a 3807 bp Hind III-Sca 1 fragment from pRubΔNot 1 was cloned into pBR322, resulting in plasmid pBR322-3818ΔNot1.

This construct contained a single Not I site. *Zoanthus* sp. green fluorescent protein (zGFP) was PCR-amplified from pZsGreen1-C1 (Cat. No. 632447, Clontech Laboratories, Inc. Mountain View, Calif.) using upstream primer 5' CGGCG-GCCGCACCGGTCGCCACCATGGC-CCAGTCCAAGCACGGCCTGAC C-3' (SEQ ID NO: 75) and downstream primer 5'-TGGCGGCCGCTCTAGATC-CGGTGGATCCCGGGCCCGCGGTACCGTCG-3' (SEQ ID NO: 76) and the resulting 804 bp product was digested with Not I and ligated into the Not 1 site of pBR322-3818 ΔNot 1 in frame with the non structural sequence, generating pBR322-3818ΔNotI-GFP. A 4096 bp Bsu36 I-Sca 1 restriction fragment from pBR322-3818ΔNotI-GFP, comprising GFP cloned into the Not I deletion in Rub non-structural coding sequences, was cloned into corresponding sites of Robo302 to generate pRub-ΔNotI-GFP.

Vero Cell Culture. African Green monkey kidney (Vero) cells were maintained in DMEM containing L-Glutamine, penicillin/streptomycin (MediaTech, Inc. Herndon Va.) and 10% fetal bovine serum at 37° C. and 5% $CO_2$ in a humidified incubator. All microscopy was carried out using an inverted Nikon Diaphot microscope equipped for fluorescence detection and digital image capture.

Generation of capped, infectious Rubella virus RNA and cell transfection. In each of the pRub plasmids, the viral genome is located downstream of an SP6 promoter. The plasmids were linearized by digestion with Spe I and transcribed using the RiboMAX Large scale RNA Production System (Promega Corp., Madison Wis.). The transcription reaction contained 1×SP6 transcription buffer, 0.8 U RNAsin, 5 mM rATP, 5 mM rCTP, 5 mM rUTP, 1 mM rGTP, 2 mM Ribo m7G(5')ppp(5')G cap analog, 5-10 μg linear ds-DNA template and 1 μL of SP6 RNA polymerase. The reaction mixture was incubated at 37° C. for 3 hours, followed by another hour in the presence of 1 μl of RNAse-free DNAse. Capped infectious rubella RNA was transfected into Vero cells as follows. The RNA was combined with 1 mL of OptiMEM, while 14 μL of DMRIEC lipid reagent (Invitrogen Corporation Carlsbad, Calif.) was added to 1 mL of OptiMEM. The two mixtures were combined and mixed gently. Cells were seeded 12-18 hours before and were washed twice with OptiMEM before being overlaid with the transfection mixture and incubated for 6-12 hours at 37° C. and 5% $CO_2$ in a humidified incubator.

Western Blot Analyses. Rubella structural proteins were detected by western blot. Vero cell lysates in RIPA buffer were sonicated for 30 seconds and then electrophoresed on a denaturing Nupage 4-12% acrylamide Bis-Tris gel (Invitrogen Corporation, Carlsbad, Calif.). Proteins were transferred to 0.2 μm Nitrocellulose filters followed by blocking for 30 min in TBS with 3% bovine serum albumin at room temperature on a rocking platform. Primary antibody binding was performed with polyclonal goat anti-rubella antibodies at a 1:400 dilution (Fitzgerald Industries International, Inc. Concord, Mass. Cat#20-RG04) in TBS with 0.2% Tween, 0.3% BSA at 4° C. overnight on a rocking platform. Blots were washed 3 times with 10 ml TBS with 0.2% Tween for 10 minutes each on an orbital shaker. Horseradish peroxidase-conjugated rabbit anti-goat IgG at a dilution of 1:5000 (Santa Cruz Biotechnology, Santa Cruz, Calif.) was added in TBS with 0.2% Tween for 40 minutes at room temperature on a rocking platform, followed by the same washing procedure as above. Proteins were visualized by enhanced chemiluminescence (Amersham Biosciences, Buckinghamshire, England) and autoradiography.

Analysis of the zGFP insert in viral RNA. Viral RNA was extracted by treating infected cells or pelleted virus with TRIzol (Invitrogen Corporation, Carlsbad, Calif.) and purified according to the manufacturer's instructions. Reverse transcription was performed using a SuperScript III kit (Invitrogen Corporation, Carlsbad, Calif.) and random hexamers. The cDNA was PCR amplified using an Advantage-GC PCR kit (Clonetech Laboratories, Mountain View, Calif.) and primers specific for rubella sequences flanking the insert. The 5' primer Robo-55 was 5'-CCATTAAGCGGTTCCTCGG-TAGC (SEQ ID NO: 23), and the 3' primer was 5'-GAGTGC-CGCGAGCGTCCGAGTGC (SEQ ID NO: 24), resulting in a product of 1.2 Kb. Amplified cDNA was analyzed by gel electrophoresis, purified using a Qiagen kit, and sequenced using the same PCR primers. To analyze zGFP function, the amplified cDNA was cloned into *E. coli* and each colony was examined for fluorescence. The cDNA was PCR amplified using a puReTaq Ready-To-Go PCR kit (GE Healthcare) and 5' primers containing an NcoI restriction site and 3' primers containing an EcoRI restriction site. The purified PCR products and a pZsGreen plasmid (Clontech Laboratories, Mountain View, Calif.) were cleaved using NcoI and EcoRI restriction endonucleases (NEB), gel purified, and ligated together to produce a functional zGFP plasmid. The products were transformed into competent DH5-α cells (Invitrogen Corporation, Carlsbad, Calif.), plated overnight in LB/Amp medium containing 100 uM IPTG, and visualized in an inverted fluorescent Nikon Diaphot microscope. Fifty five to 76 colonies per passage were analyzed for green fluorescence. Representative colonies of either type were grown in LB/Amp medium, and the plasmid was isolated (Qiagen Mini-prep kit) and sequenced (FDA core facility).

Example 2

Stable Expression of GFP Insert in a Rubella Vector

This example illustrates that a foreign gene, zGFP, can be inserted into the Not I site in the nonstructural gene nsP150 of a rubella vector, resulting in an infectious rubella hybrid that expresses the foreign protein for many generations. Although this example utilizes the foreign gene zGFP, it is contemplated that other foreign genes such as HIV antigens or HBsAgs can also be incorporated in a similar manner.

FIG. 1A provides an illustration of the pRobo 302 plasmid coding for full length, infectious rubella virus. Rubella nonstructural proteins (nsPs) are expressed as a polyprotein precursor, which is cleaved to produce nsP150 and nsP90. The structural proteins, capsid, E2 and E1, are expressed from a subgenomic promoter and cleaved to produce proteins that assemble into mature virions. Two Not I restriction sites are located in nsP150 at bp 1685 and 2192 (FIG. 1B).

To determine if a deletion of 507 bp between two Not I restriction sites was permissive for subgenomic transcription and viral replication, each full length rubella cDNA was transcribed, capped, and transfected into Vero cells as described above. Expression of rubella structural proteins was detected by western blot of the $P_0$ cell lysates on day 12. Wild type rubella expressed capsid, E2 and E1 proteins (FIG. 2, lane 5) at the same level as Not I deleted rubella (FIG. 2, lane 4).

Normal expression of the structural proteins indicated that viral RNA polymerase made negative strand template RNA, followed by plus strand subgenomic RNA coding for the structural proteins. The deletion was located in a region of unknown function, and created a potential space for insertion of a foreign gene without interfering with essential viral functions. The reporter gene zGFP was inserted into the site of the Not I deletion. This added 792 bp of DNA, for a net increase of 285 bp, and preserved the open reading frame. Vero cells were transfected with capped viral RNA, and viral supernatants were transferred onto fresh cultures. The rubella-GFP hybrid virus expressed normal levels of rubella structural proteins, as shown by western blot (FIG. 2, lanes 1 and 2 showing two independent clones). zGFP expression was detected as fluorescence of infected Vero cells. The initial transfection with infectious RNA resulted in multiple foci of bright fluorescence (FIG. 3, $P_0$ left panel). The supernatants of these cultures contained infectious virus that produced bright fluorescent foci on Vero cells.

Stability of GFP expression was tested during serial passage of culture supernatants on Vero cells. Typical results are shown at the fifth and tenth passage (FIG. 3). GFP expression was manifested by multiple bright fluorescent foci that appeared by day 4 and spread throughout the culture by day 7 to 10. Each intermediate passage showed GFP expression, and there was no fluorescence from an uninfected control run in parallel. Stable expression of the inserted gene would be needed for vaccine production in vitro, followed by sufficient replication in the host to elicit an immune response.

Genetic stability of zGFP was examined by recovering viral RNA from culture supernatants or infected cells after passages 5, 6, 10, and 11 and generating cDNA by RT-PCR of the insert. The overall GFP sequence was unchanged at passages 5 and 6, but showed a deletion of 27 bp at passages 10 and 11 (FIG. 4). This finding contrasted with fluorescence observed at later passages and suggested the possibility of a mixed population of wild type viruses giving fluorescence and mutants giving the observed sequence. To test this, the cDNAs were cloned into *E. coli* and individual colonies were examined for GFP expression. At passage 5, 76% of colonies (42 out of 55) were fluorescent, but by passages 10 and 11 only 5% of colonies (5 out of 100) expressed functional GFP.

Several clones of each phenotype were sequenced. At passage 5, four non-fluorescing clones constituted a swarm of different mutants. Two clones had point mutations Leu 46 to Pro or Phe 83 to Ser, while two others had deletions of 9 or 54 bp coding for amino acids Ile 79-Asp 81 or Lys 39-Phe 56. The deletion mutant that predominated at later passages was not detected at this passage. By passage 11, all five non-fluorescing clones had deletions ranging from 9 to 27 bp. Three had the predominant 27 bp deletion coding for amino acids Phe 83-Tyr 91 that was identical to the bulk culture. Two others had deletions coding for Asp 78-Val 80 or Thr 73-Asp 81. In contrast, two fluorescent clones at passage 11 showed the full wild type zGFP sequence. The loss of 9, 27, or 54 bp suggests persistent selective pressure to reduce the size of the zGFP insert. However, the emergence after 10 passages of a predominant clone with a 27 bp deletion that preserves the reading frame suggests that zGFP may achieve stability at a size of about 765 bp.

Rubella-GFP allowed the host range and sensitivity to interferon to be examined. FIG. 5 shows that infection was limited to Vero cells, as the virus did not grow well or at all on fibroblasts, osteocytes, epithelial cells, or a glioma. This finding may be due to cells that do not support infection lacking receptors for rubella. Alternatively, since rubella replication proceeds via a double stranded RNA intermediate that strongly elicits interferon, the growth pattern may reflect the inability of Vero cells to produce interferon, while the other cells resist infection by producing interferon.

These studies support the notion that rubella can be a vector for delivering vaccine antigens, since it can express genes as large as most viral antigens, while growing to high enough titers for vaccine production and immunization. For example, the current insert size of 792 bp (or 765 bp after deletion) is larger than hepatitis B surface antigen (680 bp) and most HIV antigens, including p24 (660 bp) and the gp41 ectodomain (570 bp). In addition, rubella hybrids can achieve sufficiently high titers for efficient vaccine production. After four passages on Vero cells, the titer reached $4\times10^6$ fluorescent foci per ml. Live attenuated rubella is one of the most efficient vaccines, with a recommended human dose of 5,000 PFU (Plotkin et al., *Rubella Vaccine*. In: Plotkin, S. A., and Orenstein W. A. (Eds.), Vaccines, $4^{th}$ ed. Saunders, Philadelphia, pp. 707-7432004), so this culture supernatant could provide 800 doses per ml.

Example 3

Treatment of HIV in a Human Subject

This example describes a particular method that can be used to treat HIV in a human subject by administration of one or more compositions that includes an effective amount of any of the disclosed isolated immunogens. Although particular methods, dosages, and modes of administrations are provided, one skilled in the art will appreciate that variations can be made without substantially affecting the treatment.

Based upon the teaching disclosed herein, HIV, such as HIV type 1, can be treated by administering a therapeutically effective amount of a composition that includes a viral-like particle produced by an isolated rubella viral vector with an HIV antigenic insert to reduce or eliminate HIV infection, replication or a combination thereof. The method can include screening subjects to Assessment Following the administration of one or more therapies, subjects having HIV (for example, HIV-1 or HIV-2) can be monitored for reductions in HIV levels, increases in a subjects CD4+ T cell count, or reductions in one or more clinical symptoms associated with HIV. In particular examples, subjects are analyzed one or more times, starting 7 days following treatment. Subjects can be monitored using any method known in the art. For example, biological samples from the subject, including blood, can be obtained and alterations in HIV or CD4+ T cell levels evaluated.

Additional Treatments

In particular examples, if subjects are stable or have a minor, mixed or partial response to treatment, they can be re-treated after re-evaluation with the same schedule and preparation of agents that they previously received for the desired amount of time, including the duration of a subject's lifetime. A partial response is a reduction, such as at least a 10%, at least 20%, at least 30%, at least 40%, at least 50%, or at least 70% in HIV infection, HIV replication or combination thereof. A partial response may also be an increase in CD4+ T cell count such as at least 350 T cells per microliter.

Example 4

Method of Monitoring Serum Antibodies to HIV or Hepatitis B

This example illustrates the methods of monitoring serum antibodies to HIV or Hepatitis B.

Based upon the teachings disclosed herein, the presence of serum antibodies to HIV or Hepatitis B can be monitored using the isolated rubella viral vector construct platforms disclosed herein, such as to detect an HIV or Hepatitis B infection. Generally, the method includes contacting a sample from a subject, such as, but not limited to a blood, serum, plasma, urine or sputum sample from the subject with one or more of the disclosed compositions including one or more rubella viral vector constructs with an HIV or Hepatitis B antigenic insert and detecting binding of antibodies in the sample to the one or more constructs. The binding can be detected by any means known to one of skill in the art, including the use of labeled secondary antibodies that specifically bind the antibodies from the sample. Labels include radiolabels, enzymatic labels, and fluorescent labels.

Example 5

Binding of HIVIgG and Human Sera from HIV-1 Positive Patients to Disclosed Rubella Viral Vector Constructs Based upon the teaching herein, the utility of a rubella viral vector construct with an HIV antigenic insert to identify sera that contain neutralizing antibodies against the HIV antigenic insert included with the rubella viral vector construct can be determined by screening a set of weakly and broadly neutralizing human HIV-1 positive sera and HIV-IgG for binding to one or more of the disclosed constructs or virus like particles that include one or more disclosed viral constructs. Human sera from HIV-1 positive patients and antibodies specific for HIV antigens can be serially diluted and analyzed for binding to HIV antigens and particles containing such polypeptides in ELISA format.

Example 6

Immunization of Subjects with HIV

Based upon the teaching herein, subjects are immunized with a dose of 1 pg to 1 ng and given at 0, 1, and 6 months of the disclosed rubella viral vector including one or more HIV antigens or virus-like particles containing the disclosed vector including one or more of such antigens by intramuscular route. Sera from the subject is analyzed for binding to one or more of the HIV antibodies by ELISA.

In addition, the sera can be checked for their neutralizing ability in a viral neutralization assay using luciferase-based HIV entry assay. If the neutralizing titers are high enough, the subject is challenged with SHIV virus bearing the same envelope glycoproteins as HIV. Alternatively, SIV antigens can be incorporated into the disclosed viral vector, monkeys can be immunized with rubella-SIV, and challenged with virulent SIV strains. In one particular example, the subject is a rhesus monkey.

Example 7

Stable Expression of SIV and HIV Antigens in a Rubella Vector

This example illustrates that SIV and HIV antigens can be inserted into the Not I site of a rubella vector, resulting in an infectious rubella hybrid that expresses the foreign protein for multiple generations.

In a first set of studies, full length RNA coding for the rubella vector plus the insert was transcribed, capped, and the vector genes were transfected into Vero cells (passage 0) as described previously in Example 1. Growth of vector with the insert was then determined by measuring rubella proteins by Western blot analysis. Alternatively, expression of the insert gene product was determined by Western blot using antibodies specific for the insert. For example, this could be the Gag genes of SIV or the MPER antigen of HIV.

In a second set of studies, Vero cells were transfected as in the original method with rubella viral constructs containing SIV or HIV sequences inserted at the Not I site. These cells were called passage P0. After 7 days, virus and cells were transferred together as a cell suspension. The suspension was made by scraping a quarter of the cell monolayer, and then diluting the cell suspension to 2 ml, followed by transferring 0.1 to 0.2 ml directly onto a new monolayer of Vero cells to make passage P1. This procedure was repeated for multiple passages.

Figure 5:
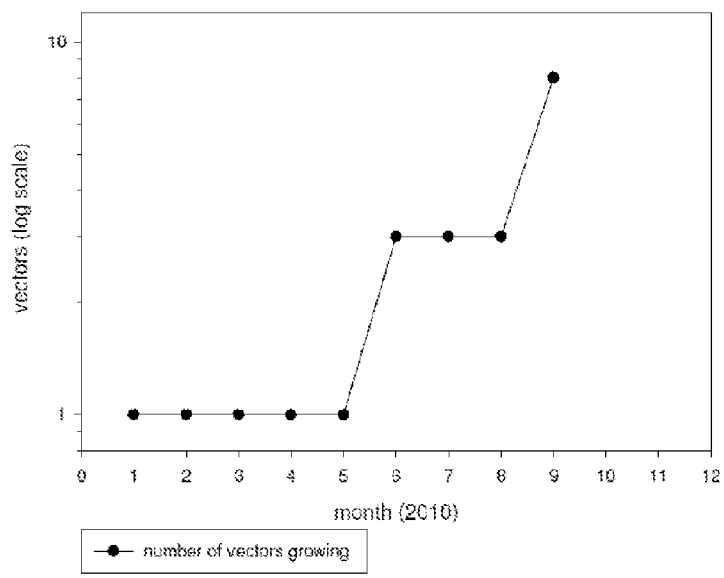
FIG. 5 is a graph of a time course illustrating rubella vector growth over a number of months.
Figure 6:
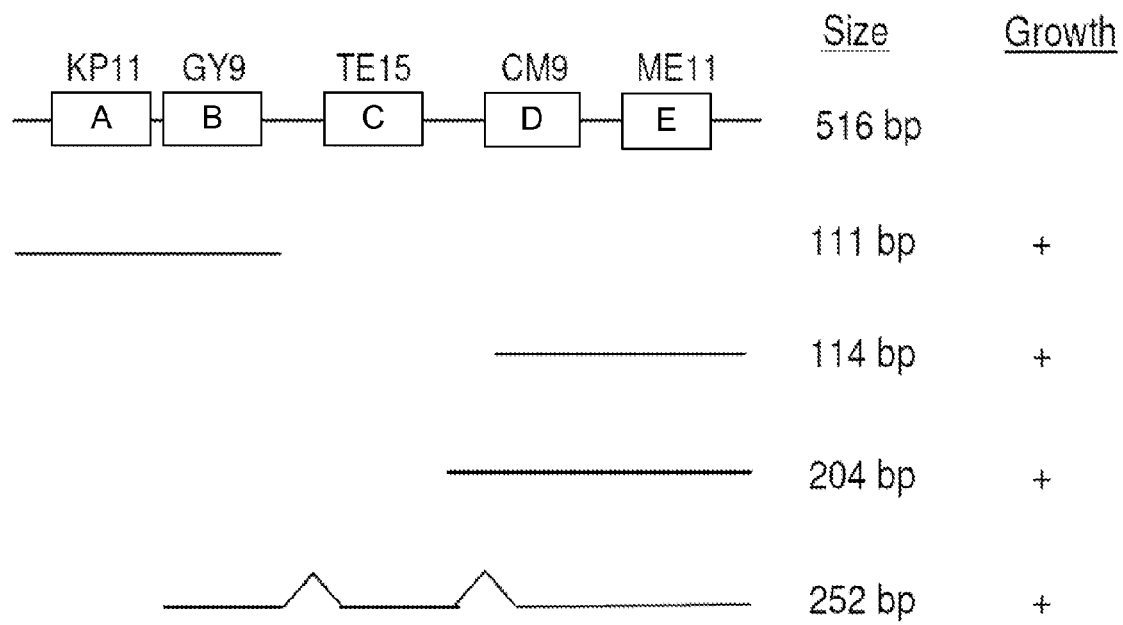
FIG. 6 is a schematic illustrating the arrangement of various Gag epitopes expressed in a rubella vector.
Figure 7:
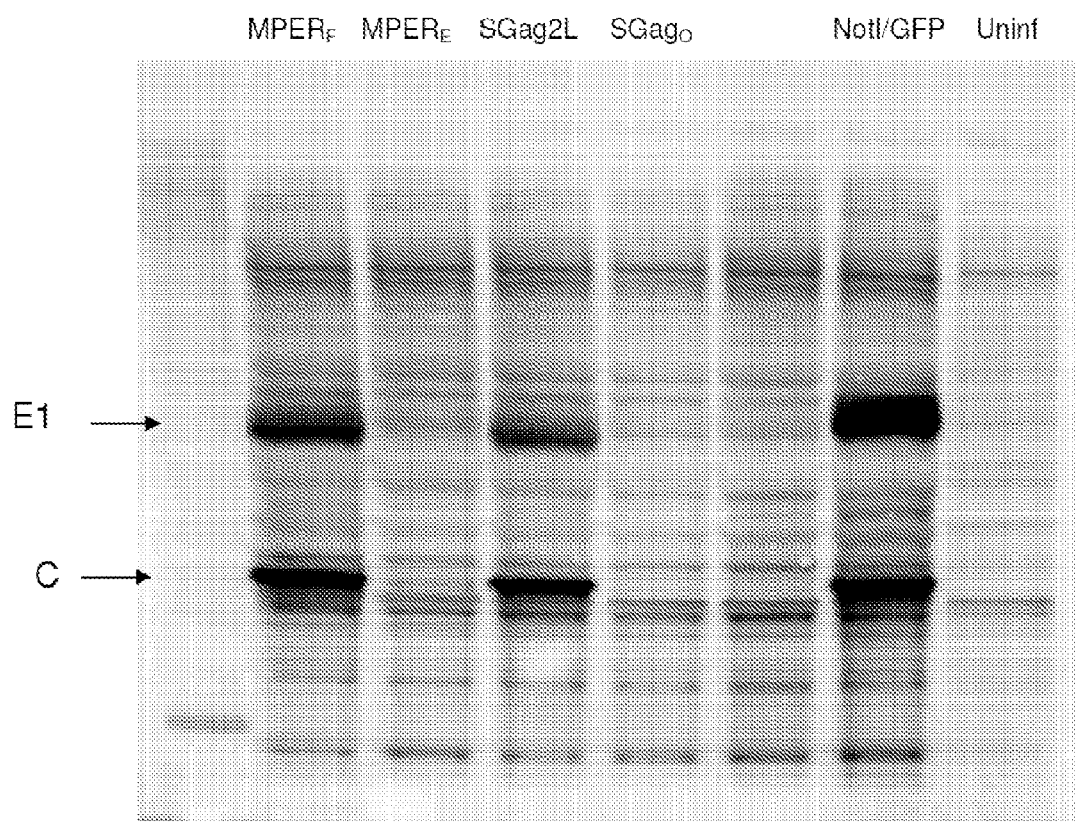
FIG. 7 is a digital image illustrating growth of two rubella vectors and rubella-GFP control as detected by western blot of rubella proteins E1 and C.
Figure 8:
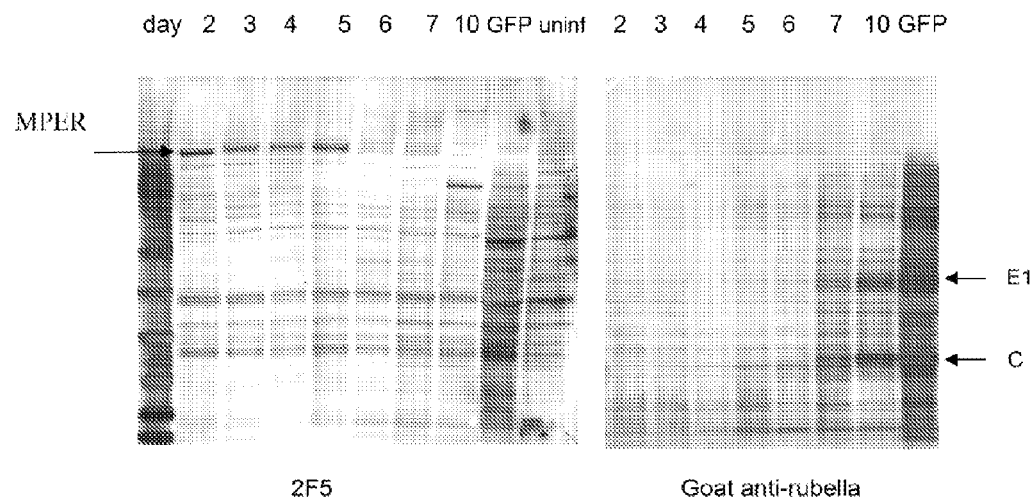
FIG. 8 is a digital image of a western blot illustrating a time course of MPER expression by rubella-$MPER_F$ vector as detected with anti-MPER monoclonal 2F5 or anti-rubella polyclonal antibodies.
Figure 9:
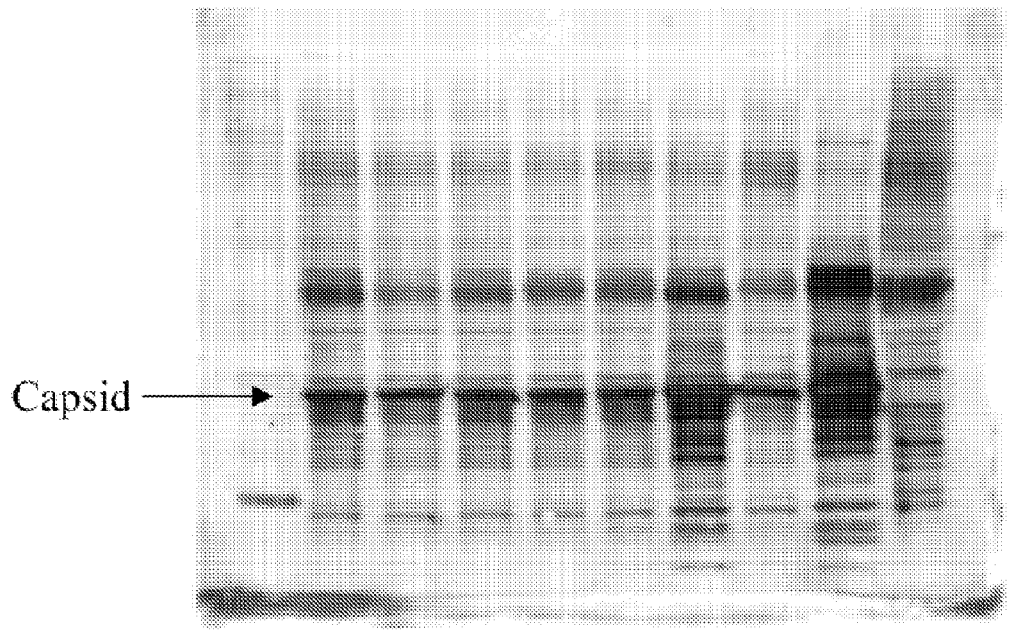
FIG. 9 is a digital image of a western blot illustrating growth of seven rubella-sGag vectors at passage 2, as detected with antibodies to rubella capsid.

FIG. 5 illustrates the number of vectors expressed within cells that were able to grow over a period of months by using the second rubella viral cell culture method. FIG. 6 illustrates the size and position of various Gag epitopes expressed in live rubella vectors. Table 3 provides the amino acid sequences, insert name and size of inserts which were expressed in live rubella vectors. Western blot analyses presented in FIGS. 7-9 illustrate successful vector growth and expression of rubella proteins when the vector includes various Gag and MPR epitopes with both cell culture methods.

TABLE 3

SIV Gag and HIV MPR sequences expressed in live rubella vectors

| Insert name | Bp | Insert Amino acid sequence | SEQ ID NO. |
|---|---|---|---|
| SGAG1-1 | 111 | REGSQKILSVLAPLVPTGSENLKSLYNTVSVIWSIHAED | 82 |
| SGAG2 | 114 | FQALSEGCTPYDINQMLNCVGDHQAAMQIIRDIINEEA | 83 |
| SGAG2L | 204 | LPLSPRTLNAWVKLIEEKKFGAEVVPGFQALSEGCTPYDINQMLNCVGDHQAAMQIIRDIINEEA | 84 |
| SGAG2L-A | 249 | LPLSPRTLNAWVKLIEEKKFGAEVVPGFQALSEGCTPYDINQMLNCVGDHQAAMQIIRDIINEEATRSQKILSVLAPLVPT | 85 |
| SGAG2L-B | 243 | LPLSPRTLNAWVKLIEEKKFGAEVVPGFQALSEGCTPYDINQMLNCVGDHQAAMQIIRDIINEEATRTGSENLKSLYNT | 86 |
| SGAG2L-C | 267 | LPLSPRTLNAWVKLIEEKKFGAEVVPGFQALSEGCTPYDINQMLNCVGDHQAAMQIIRDIINEEATRHTEEAKQIVQRHLVVETGTT | 87 |
| BC-SGAG2 | 252 | VPTGSENLKSLYNTVTRVKHTEEAKQIVQRHLVVETGTTSDAFQALSEGCTPYDINQMLNCVGDHQAAMQIIRDIINEEA | 88 |
| MPR-E | | PSWNWFDITNWLWYIRLDA | 89 |
| MPR-F | 70 | PSAQEKNEKELLELDKWASLWN | 30 |
| ABC-SGAG2 | 335 | LDRFGLAESLLENKEGSQKILSVLAPLVPTGSENLKSLYNTVTRVKHTEEAKQIVQRHLVVETGTTETSDAFQALSEGCTPYDINQMLNCVGDHQAAMQIIRDIINEEA | 90 |
| ABC-SGAG2L | 411 | LDRFGLAESLLENKEGSQKILSVLAPLVPTGSENLKSLYNTVTRVKHTEEAKQIVQRHLVVETGTTETRLPLSPRTLNAWVKLIEEKKFGAEVVPGFQALSEGCTPYDINQMLNCVGDHQAAMQIIRDIINEEA | 91 |

For example, FIG. 7 illustrates growth of two rubella vectors (made by the first method) and rubella-GFP control detected by western blot of rubella proteins E1 and C. As illustrated in FIG. 7, two different epitopes of SIV gag were expressed (SGAG2L and SGAG$_0$). SGAG$_0$ has the same amino acid sequence as wild type SGAG; its RNA sequence is different, since it has been codon optimized. Besides giving better expression, the codon optimized insert appeared more like the GC rich rubella RNA surrounding it.

Further, FIG. 8 shows the time course of MPR expression in which MPER$_f$ was expressed as part of an early gene of the rubella virus, from days 2 to 5 of infection.

FIG. 9 illustrates successful expression of seven rubella-sGag vectors at passage 2 (made by the second method) vs. a rubella-GFP control in second lane from the right and uninfected cells in last lane, as detected by western blot with antibodies to rubella capsid. Arrow indicates the capsid band (Lane 1, Molecular weight; Lane 2, SGAG2; Lane 3, SGAG2L; Lane 4, SGAG2L-A; Lane 5,SGAG2L-B; Lane 6, SGAG2L-C; Lane 7, BC-SGAG2; Lane 8, SGAG1-1; Lane 9, GFP insert; Lane 10, uninfected control).

These studies show stable expression of SIV and HIV epitopes in a rubella vector resulting in an infectious rubella hybrid that expresses the foreign protein for sufficient generations to allow expansion in a fermentor, followed by propagation and expression as a vaccine antigen in the immunized host.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as my invention all that comes within the scope and spirit of these claims.

We claim:

1. An isolated rubella viral vector, comprising a rubella non-structural protein open reading frame (ORF) with an in-frame deletion between two NotI restriction enzyme sites, a rubella structural protein ORF, and a heterologous antigenic insert, wherein the heterologous antigenic insert is positioned within the rubella non-structural protein ORF and consists of the amino acid sequence set forth as one of:

(SEQ ID NO: 82)
REGSQKILSVLAPLVPTGSENLKSLYNTVSVIWSIHAED;

(SEQ ID NO: 83)
FQALSEGCTPYDINQMLNCVGDHQAAMQIIRDIINEEA;

(SEQ ID NO: 84)
LPLSPRTLNAWVKLIEEKKFGAEVVPGFQALSEGCTPYDINQMLNCVGDHQAAM
QIIRDIINEEA;

(SEQ ID NO: 85)
LPLSPRTLNAWVKLIEEKKFGAEVVPGFQALSEGCTPYDINQMLNCVGDHQAAM
QIIRDIINEEATRSQKILSVLAPLVPT;

(SEQ ID NO: 86)
LPLSPRTLNAWVKLIEEKKFGAEVVPGFQALSEGCTPYDINQMLNCVGDHQAAM
QIIRDIINEEATRTGSENLKSLYNT;

(SEQ ID NO: 87)
LPLSPRTLNAWVKLIEEKKFGAEVVPGFQALSEGCTPYDINQMLNCVGDHQAAM
QIIRDIINEEATRHTEEAKQIVQRHLVVETGTT;

-continued (SEQ ID NO: 88)
VPTGSENLKSLYNTVTRVKHTEEAKQIVQRHLVVETGTTSDAFQALSEGCTPYDI

NQMLNCVGDHQAAMQIIRDIINEEA.

2. An isolated host cell transformed with the isolated rubella viral vector of claim 1.

3. A composition comprising the isolated rubella viral vector of claim 1.

4. The composition of claim 3, further comprising an adjuvant.

* * * * *

SEQUENCE LISTING

```
<160> NUMBER OF SEQ ID NOS: 103

<210> SEQ ID NO 1
<211> LENGTH: 16
<212> TYPE: PRT
<213> ORGANISM: Human immunodeficiency virus
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid
```

```
<400> SEQUENCE: 1

Asn Glu Xaa Xaa Leu Leu Xaa Leu Asp Lys Trp Ala Ser Leu Trp Asn
1               5                   10                  15

<210> SEQ ID NO 2
<211> LENGTH: 28
<212> TYPE: PRT
<213> ORGANISM: Human immunodeficiency virus

<400> SEQUENCE: 2

Asn Glu Gln Glu Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 3
<211> LENGTH: 28
<212> TYPE: PRT
<213> ORGANISM: Human immunodeficiency virus

<400> SEQUENCE: 3

Asn Glu Gln Asp Leu Leu Ala Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 4
<211> LENGTH: 28
<212> TYPE: PRT
<213> ORGANISM: Human immunodeficiency virus

<400> SEQUENCE: 4

Asn Glu Gln Asp Leu Leu Ala Leu Asp Lys Trp Ala Asn Leu Trp Asn
1               5                   10                  15

Trp Phe Asp Ile Ser Asn Trp Leu Trp Tyr Ile Lys
            20                  25

<210> SEQ ID NO 5
<211> LENGTH: 28
<212> TYPE: PRT
<213> ORGANISM: Human immunodeficiency virus

<400> SEQUENCE: 5

Asn Glu Gln Asp Leu Leu Ala Leu Asp Lys Trp Ala Asn Leu Trp Asn
1               5                   10                  15

Trp Phe Asn Ile Thr Asn Trp Leu Trp Tyr Ile Arg
            20                  25

<210> SEQ ID NO 6
<211> LENGTH: 28
<212> TYPE: PRT
<213> ORGANISM: Human immunodeficiency virus

<400> SEQUENCE: 6

Asn Glu Gln Glu Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 7
<211> LENGTH: 28
```

```
<212> TYPE: PRT
<213> ORGANISM: Human immunodeficiency virus

<400> SEQUENCE: 7

Asn Glu Lys Asp Leu Leu Ala Leu Asp Ser Trp Lys Asn Leu Trp Asn
1               5                   10                  15

Trp Phe Asp Ile Thr Asn Trp Leu Trp Tyr Ile Lys
            20                  25

<210> SEQ ID NO 8
<211> LENGTH: 28
<212> TYPE: PRT
<213> ORGANISM: Human immunodeficiency virus

<400> SEQUENCE: 8

Asn Glu Gln Asp Leu Leu Ala Leu Asp Ser Trp Glu Asn Leu Trp Asn
1               5                   10                  15

Trp Phe Asp Ile Thr Asn Trp Leu Trp Tyr Ile Lys
            20                  25

<210> SEQ ID NO 9
<211> LENGTH: 28
<212> TYPE: PRT
<213> ORGANISM: Human immunodeficiency virus

<400> SEQUENCE: 9

Asn Glu Gln Glu Leu Leu Glu Leu Asp Lys Trp Ala Ser Leu Trp Asn
1               5                   10                  15

Trp Phe Ser Ile Thr Gln Trp Leu Trp Tyr Ile Lys
            20                  25

<210> SEQ ID NO 10
<211> LENGTH: 28
<212> TYPE: PRT
<213> ORGANISM: Human immunodeficiency virus

<400> SEQUENCE: 10

Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 11
<211> LENGTH: 28
<212> TYPE: PRT
<213> ORGANISM: Human immunodeficiency virus

<400> SEQUENCE: 11

Asn Glu Gln Asp Leu Leu Ala Leu Asp Lys Trp Asp Asn Leu Trp Ser
1               5                   10                  15

Trp Phe Thr Ile Thr Asn Trp Leu Trp Tyr Ile Lys
            20                  25

<210> SEQ ID NO 12
<211> LENGTH: 28
<212> TYPE: PRT
<213> ORGANISM: Human immunodeficiency virus

<400> SEQUENCE: 12

Asn Glu Gln Asp Leu Leu Ala Leu Asp Lys Trp Ala Ser Leu Trp Asn
1               5                   10                  15

Trp Phe Asp Ile Thr Lys Trp Leu Trp Tyr Ile Lys
```

<210> SEQ ID NO 13
<211> LENGTH: 28
<212> TYPE: PRT
<213> ORGANISM: Human immunodeficiency virus

<400> SEQUENCE: 13

Asn Glu Gln Asp Leu Leu Ala Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 14
<211> LENGTH: 28
<212> TYPE: PRT
<213> ORGANISM: Human immunodeficiency virus

<400> SEQUENCE: 14

Asn Glu Lys Asp Leu Leu Glu Leu Asp Lys Trp Ala Ser Leu Trp Asn
1               5                   10                  15

Trp Phe Asp Ile Thr Asn Trp Leu Trp Tyr Ile Lys
            20                  25

<210> SEQ ID NO 15
<211> LENGTH: 28
<212> TYPE: PRT
<213> ORGANISM: Human immunodeficiency virus

<400> SEQUENCE: 15

Asn Glu Gln Glu Ile Leu Ala Leu Asp Lys Trp Ala Ser Leu Trp Asn
1               5                   10                  15

Trp Phe Asp Ile Ser Lys Trp Leu Trp Tyr Ile Lys
            20                  25

<210> SEQ ID NO 16
<211> LENGTH: 28
<212> TYPE: PRT
<213> ORGANISM: Human immunodeficiency virus

<400> SEQUENCE: 16

Asn Glu Gln Asp Leu Leu Ala Leu Asp Lys Trp Ala Asn Leu Trp Asn
1               5                   10                  15

Trp Phe Asn Ile Ser Asn Trp Leu Trp Tyr Ile Lys
            20                  25

<210> SEQ ID NO 17
<211> LENGTH: 28
<212> TYPE: PRT
<213> ORGANISM: Human immunodeficiency virus

<400> SEQUENCE: 17

Asn Glu Gln Asp Leu Leu Ala Leu Asp Lys Trp Ala Ser Leu Trp Ser
1               5                   10                  15

Trp Phe Asp Ile Ser Asn Trp Leu Trp Tyr Ile Lys
            20                  25

<210> SEQ ID NO 18
<211> LENGTH: 28
<212> TYPE: PRT
<213> ORGANISM: Human immunodeficiency virus

<400> SEQUENCE: 18

-continued

Asn Glu Lys Asp Leu Leu Ala Leu Asp Ser Trp Lys Asn Leu Trp Ser
1               5                   10                  15

Trp Phe Asp Ile Thr Asn Trp Leu Trp Tyr Ile Lys
            20                  25

<210> SEQ ID NO 19
<211> LENGTH: 28
<212> TYPE: PRT
<213> ORGANISM: Human immunodeficiency virus

<400> SEQUENCE: 19

Asn Glu Gln Glu Leu Leu Gln Leu Asp Lys Trp Ala Ser Leu Trp Asn
1               5                   10                  15

Trp Phe Ser Ile Thr Asn Trp Leu Trp Tyr Ile Lys
            20                  25

<210> SEQ ID NO 20
<211> LENGTH: 28
<212> TYPE: PRT
<213> ORGANISM: Human immunodeficiency virus

<400> SEQUENCE: 20

Asn Glu Gln Asp Leu Leu Ala Leu Asp Lys Trp Ala Ser Leu Trp Asn
1               5                   10                  15

Trp Phe Asp Ile Ser Asn Trp Leu Trp Tyr Ile Lys
            20                  25

<210> SEQ ID NO 21
<211> LENGTH: 28
<212> TYPE: PRT
<213> ORGANISM: Human immunodeficiency virus

<400> SEQUENCE: 21

Asn Glu Gln Glu Leu Leu Ala Leu Asp Lys Trp Ala Ser Leu Trp Asn
1               5                   10                  15

Trp Phe Asp Ile Ser Asn Trp Leu Trp Tyr Ile Arg
            20                  25

<210> SEQ ID NO 22
<211> LENGTH: 28
<212> TYPE: PRT
<213> ORGANISM: Human immunodeficiency virus

<400> SEQUENCE: 22

Asn Glu Gln Glu Leu Leu Glu Leu Asp Lys Trp Ala Ser Leu Trp Asn
1               5                   10                  15

Trp Phe Asn Ile Thr Asn Trp Leu Trp Tyr Ile Lys
            20                  25

<210> SEQ ID NO 23
<211> LENGTH: 23
<212> TYPE: PRT
<213> ORGANISM: Human immunodeficiency virus

<400> SEQUENCE: 23

Cys Cys Ala Thr Thr Ala Ala Gly Cys Gly Gly Thr Thr Cys Cys Thr
1               5                   10                  15

Cys Gly Gly Thr Ala Gly Cys
            20

<210> SEQ ID NO 24

```
<211> LENGTH: 23
<212> TYPE: PRT
<213> ORGANISM: Human immunodeficiency virus

<400> SEQUENCE: 24

Gly Ala Gly Thr Gly Cys Cys Gly Cys Gly Ala Gly Cys Gly Thr Cys
1               5                   10                  15

Cys Gly Ala Gly Thr Gly Cys
            20

<210> SEQ ID NO 25
<211> LENGTH: 22
<212> TYPE: PRT
<213> ORGANISM: Human immunodeficiency virus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be any hydrophobic amino acid.
<220> FEATURE:
<221> NAME/KEY: MISC_FEATURE
<222> LOCATION: (10)..(10)
<223> OTHER INFORMATION: Xaa can be any hydrophobic amino acid.
<220> FEATURE:
<221> NAME/KEY: MISC_FEATURE
<222> LOCATION: (18)..(18)
<223> OTHER INFORMATION: Xaa can be any hydrophobic amino acid.

<400> SEQUENCE: 25

Xaa Phe Ile Met Ile Val Gly Gly Leu Xaa Gly Leu Arg Ile Val Phe
1               5                   10                  15

Thr Xaa Leu Ser Ile Val
            20

<210> SEQ ID NO 26
<211> LENGTH: 22
<212> TYPE: PRT
<213> ORGANISM: Human immunodeficiency virus

<400> SEQUENCE: 26

Ile Phe Ile Met Ile Val Gly Gly Leu Ile Gly Leu Arg Ile Val Phe
1               5                   10                  15

Thr Val Leu Ser Ile Val
            20

<210> SEQ ID NO 27
<211> LENGTH: 22
<212> TYPE: PRT
<213> ORGANISM: Human immunodeficiency virus

<400> SEQUENCE: 27

Leu Phe Ile Met Ile Val Gly Gly Leu Ile Gly Leu Arg Ile Val Phe
1               5                   10                  15

Thr Ala Leu Ser Ile Val
            20

<210> SEQ ID NO 28
<211> LENGTH: 22
<212> TYPE: PRT
<213> ORGANISM: Human immunodeficiency virus

<400> SEQUENCE: 28

Ile Phe Ile Met Ile Val Gly Gly Leu Val Gly Leu Arg Ile Val Phe
```

<210> SEQ ID NO 29
<211> LENGTH: 276
<212> TYPE: PRT
<213> ORGANISM: Human immunodeficiency virus

<400> SEQUENCE: 29

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Pro Ser Ser Trp Ala Phe Ala
        195                 200                 205

Lys Tyr Leu Trp Glu Trp Ala Ser Val Arg Phe Ser Trp Leu Ser Leu
    210                 215                 220

Leu Val Pro Phe Val Gln Trp Phe Val Gly Leu Ser Pro Thr Val Trp
225                 230                 235                 240

Leu Ser Ala Ile Trp Met Met Trp Tyr Trp Gly Pro Ser Leu Tyr Ser
                245                 250                 255

Ile Val Ser Pro Phe Ile Pro Leu Leu Pro Ile Phe Phe Cys Leu Trp
            260                 265                 270

Val Tyr Ile Gly
        275
```

<210> SEQ ID NO 30
<211> LENGTH: 22
<212> TYPE: PRT
<213> ORGANISM: Human immunodeficiency virus

<400> SEQUENCE: 30

```
Pro Ser Ala Gln Glu Lys Asn Glu Lys Glu Leu Leu Glu Leu Asp Lys
1               5                   10                  15

Trp Ala Ser Leu Trp Asn
```

<210> SEQ ID NO 31
<211> LENGTH: 226
<212> TYPE: PRT
<213> ORGANISM: Human immunodeficiency virus

<400> SEQUENCE: 31

```
Glu Phe Ile Thr Ser Gly Phe Leu Gly Pro Leu Leu Val Leu Gln Ala
1               5                   10                  15

Gly Phe Phe Leu Leu Thr Arg Ile Leu Thr Ile Pro Gln Ser Leu Asp
            20                  25                  30

Ser Trp Trp Thr Ser Leu Asn Phe Leu Gly Gly Ser Pro Val Cys Leu
        35                  40                  45

Gly Gln Asn Ser Gln Ser Pro Thr Ser Asn His Ser Pro Thr Ser Cys
    50                  55                  60

Pro Pro Ile Cys Pro Gly Tyr Arg Trp Met Cys Leu Arg Arg Phe Ile
65                  70                  75                  80

Ile Phe Leu Phe Ile Leu Leu Cys Leu Ile Phe Leu Leu Val Leu
                85                  90                  95

Leu Asp Tyr Gln Gly Met Leu Pro Val Cys Pro Leu Ile Pro Gly Ser
                100                 105                 110

Thr Thr Thr Ser Thr Gly Pro Cys Lys Thr Cys Thr Thr Pro Ala Gln
            115                 120                 125

Gly Asn Ser Lys Phe Pro Ser Cys Cys Cys Thr Lys Pro Thr Asp Gly
    130                 135                 140

Asn Cys Thr Cys Ile Ser Ile Pro Ser Ser Trp Ala Phe Ala Lys Tyr
145                 150                 155                 160

Leu Trp Glu Trp Ala Ser Val Arg Phe Ser Trp Leu Ser Leu Leu Val
                165                 170                 175

Pro Phe Val Gln Trp Phe Val Gly Leu Ser Pro Thr Val Trp Leu Ser
            180                 185                 190

Ala Ile Trp Met Met Trp Tyr Trp Gly Pro Ser Leu Tyr Ser Ile Val
        195                 200                 205

Ser Pro Phe Ile Pro Leu Leu Pro Ile Phe Phe Cys Leu Trp Val Tyr
    210                 215                 220

Ile Gly
225
```

<210> SEQ ID NO 32
<211> LENGTH: 15
<212> TYPE: PRT
<213> ORGANISM: Human immunodeficiency virus

<400> SEQUENCE: 32

```
Ala Ser Leu Trp Asn Trp Phe Asn Ile Thr Asn Trp Leu Trp Tyr
1               5                   10                  15
```

<210> SEQ ID NO 33
<211> LENGTH: 15
<212> TYPE: PRT
<213> ORGANISM: Human immunodeficiency virus

<400> SEQUENCE: 33

```
Ile Lys Leu Phe Ile Met Ile Val Gly Gly Leu Val Gly Leu Arg
1               5                   10                  15
```

<210> SEQ ID NO 34

```
<211> LENGTH: 4
<212> TYPE: PRT
<213> ORGANISM: Human immunodeficiency virus
<220> FEATURE:
<221> NAME/KEY: misc_feature
<222> LOCATION: (4)..(4)
<223> OTHER INFORMATION: Xaa can be any naturally occurring amino acid

<400> SEQUENCE: 34

Cys Ala Ala Xaa
1

<210> SEQ ID NO 35
<211> LENGTH: 7
<212> TYPE: PRT
<213> ORGANISM: Human immunodeficiency virus

<400> SEQUENCE: 35

Glu Leu Asp Lys Trp Ala Ser
1               5

<210> SEQ ID NO 36
<211> LENGTH: 6
<212> TYPE: PRT
<213> ORGANISM: Human immunodeficiency virus

<400> SEQUENCE: 36

Asn Trp Phe Asp Ile Thr
1               5

<210> SEQ ID NO 37
<211> LENGTH: 4
<212> TYPE: PRT
<213> ORGANISM: Human immunodeficiency virus

<400> SEQUENCE: 37

Gly Pro Gly Pro
1

<210> SEQ ID NO 38
<211> LENGTH: 18
<212> TYPE: DNA
<213> ORGANISM: Artificial sequence
<220> FEATURE:
<223> OTHER INFORMATION: Synthetic nucleic acid primer.

<400> SEQUENCE: 38
ggagctcgtc gacagcaa                                              18

<210> SEQ ID NO 39
<211> LENGTH: 23
<212> TYPE: DNA
<213> ORGANISM: Artificial sequence
<220> FEATURE:
<223> OTHER INFORMATION: Synthetic nucleic acid primer.

<400> SEQUENCE: 39
gctctagacc cgatgtacac cca                                        23

<210> SEQ ID NO 40
<211> LENGTH: 26
<212> TYPE: DNA
<213> ORGANISM: Artificial sequence
<220> FEATURE:
<223> OTHER INFORMATION: Synthetic nucleic acid primer.

<400> SEQUENCE: 40
```

```
gctctagaaa cgagcaggag ctgctg                                          26

<210> SEQ ID NO 41
<211> LENGTH: 36
<212> TYPE: DNA
<213> ORGANISM: Artificial sequence
<220> FEATURE:
<223> OTHER INFORMATION: Synthetic neucleic acid primer.

<400> SEQUENCE: 41
cgcggatcct caccccttga tgtaccacag ccactt                               36

<210> SEQ ID NO 42
<211> LENGTH: 33
<212> TYPE: DNA
<213> ORGANISM: Artificial sequence
<220> FEATURE:
<223> OTHER INFORMATION: Synthetic neucleic acid primer.

<400> SEQUENCE: 42
cgcggatcct caatggtgat ggtgatggtg ggg                                  33

<210> SEQ ID NO 43
<211> LENGTH: 26
<212> TYPE: DNA
<213> ORGANISM: Artificial sequence
<220> FEATURE:
<223> OTHER INFORMATION: Synthetic neucleic acid primer.

<400> SEQUENCE: 43
gctctagagc cgtggagcgg tacctg                                          26

<210> SEQ ID NO 44
<211> LENGTH: 33
<212> TYPE: DNA
<213> ORGANISM: Artificial sequence
<220> FEATURE:
<223> OTHER INFORMATION: Synthetic neucleic acid primer.

<400> SEQUENCE: 44
ctcggatcct caaatcatga tgaaaatctt gat                                  33

<210> SEQ ID NO 45
<211> LENGTH: 30
<212> TYPE: DNA
<213> ORGANISM: Artificial sequence
<220> FEATURE:
<223> OTHER INFORMATION: Synthetic neucleic acid primer.

<400> SEQUENCE: 45
ctcggatcct cacaccaggc caccaacaat                                      30

<210> SEQ ID NO 46
<211> LENGTH: 30
<212> TYPE: DNA
<213> ORGANISM: Artificial sequence
<220> FEATURE:
<223> OTHER INFORMATION: Synthetic neucleic acid primer.

<400> SEQUENCE: 46
ctcggatcct cacaccagcc tcaggcccac                                      30

<210> SEQ ID NO 47
<211> LENGTH: 21
<212> TYPE: DNA
```

<213> ORGANISM: Artificial sequence
<220> FEATURE:
<223> OTHER INFORMATION: Synthetic neucleic acid primer.

<400> SEQUENCE: 47
ctcggatcct caggcgggcg c                                              21

<210> SEQ ID NO 48
<211> LENGTH: 48
<212> TYPE: DNA
<213> ORGANISM: Artificial sequence
<220> FEATURE:
<223> OTHER INFORMATION: Synthetic neucleic acid primer.

<400> SEQUENCE: 48
ccctgcaaga cctgcaccac caccggtcag ggcaactcca agttcccc                 48

<210> SEQ ID NO 49
<211> LENGTH: 48
<212> TYPE: DNA
<213> ORGANISM: Artificial sequence
<220> FEATURE:
<223> OTHER INFORMATION: Synthetic neucleic acid primer.

<400> SEQUENCE: 49
ggggaacttg gagttgccct gaccggtggt ggtgcaggtc ttgcaggg                 48

<210> SEQ ID NO 50
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 50
ggcaccggta acgagcagga gctgctg                                        27

<210> SEQ ID NO 51
<211> LENGTH: 33
<212> TYPE: DNA
<213> ORGANISM: Artificial sequence
<220> FEATURE:
<223> OTHER INFORMATION: Synthetic neucleic acid primer.

<400> SEQUENCE: 51
ggcaccggtc cccttgatgt accacagcca ctt                                 33

<210> SEQ ID NO 52
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 52
agcgaattca acgagcagga gctgctg                                        27

<210> SEQ ID NO 53
<211> LENGTH: 27
<212> TYPE: DNA
<213> ORGANISM: Artificial sequence
<220> FEATURE:
<223> OTHER INFORMATION: Synthetic neucleic acid primer.

<400> SEQUENCE: 53
cgcggatcct cacccgatgt acaccca                                        27

<210> SEQ ID NO 54
<211> LENGTH: 45
<212> TYPE: DNA
<213> ORGANISM: Artificial sequence
<220> FEATURE:
<223> OTHER INFORMATION: Synthetic neucleic acid primer.

<400> SEQUENCE: 54
caggaagccg gaggtgatga acccttgat gtaccacagc cactt            45

<210> SEQ ID NO 55
<211> LENGTH: 45
<212> TYPE: DNA
<213> ORGANISM: Artificial sequence
<220> FEATURE:
<223> OTHER INFORMATION: Synthetic neucleic acid primer.

<400> SEQUENCE: 55
aagtggctgt ggtacatcaa ggggttcatc acctccggct tcctg            45

<210> SEQ ID NO 56
<211> LENGTH: 515
<212> TYPE: DNA
<213> ORGANISM: Artificial sequence
<220> FEATURE:
<223> OTHER INFORMATION: Neucleic acid sequence for recombinant
      antigenic insert peptide.

<400> SEQUENCE: 56
attagataga tttggattag cagaaagcct gttggagaac aaagaaggat gtcaaaaaat      60
actttcggtc ttagctccat tagtgccaac aggctcagaa atttaaaaa gcctttataa     120 tactgtctgc gtcatctggt gcattcacgc agaagagaaa gtgaaacaca ctgaggaagc     180
aaaacagata gtgcagagac acctagtggt ggaaacagga acaacagaaa ctatgccaaa     240
aacaagtaga ccaacagcac catctagcgg cagaggagga aattacccag tacaacaaat     300
aggtggtaac tatgtccacc tgccattaag cccgagaaca ttaaatgcct gggtaaaatt     360
gatagaggaa aagaaatttg gagcagaagt agtgccagga tttcaggcac tgtcagaagg     420
ttgcaccccc tatgacatta atcagatgtt aaattgtgtg ggagaccatc aagcggctat     480
gcagattatc agagatatta taaacgagga ggctg                                515

<210> SEQ ID NO 57
<211> LENGTH: 295
<212> TYPE: PRT
<213> ORGANISM: Artificial sequence
<220> FEATURE:
<223> OTHER INFORMATION: Recombinant antigenic insert peptide construct.

<400> SEQUENCE: 57

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
        35                  40                  45

Thr Asn Trp Leu Trp Tyr Ile Arg Leu Phe Ile Met Ile Val Gly Gly
    50                  55                  60

Leu Ile Gly Leu Arg Ile Val Phe Ala Val Leu Ser Ile Pro Gln Ser
65                  70                  75                  80

```
Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
            115                 120                 125

Phe Ile Ile Phe Leu Phe Ile Leu Leu Leu Cys Leu Ile Phe Leu Leu
        130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
            180                 185                 190

Asp Gly Asn Cys Thr Cys Ile Pro Ile Asn Glu Lys Glu Leu Leu Glu
        195                 200                 205

Leu Asp Lys Trp Ala Ser Leu Trp Asn Trp Phe Asp Ile Thr Asn Trp
210                 215                 220

Leu Trp Tyr Ile Arg Leu Phe Ile Met Ile Val Gly Gly Leu Ile Gly
225                 230                 235                 240

Leu Arg Ile Val Phe Ala Val Leu Ser Ile Val Val Gly Leu Ser Pro
                245                 250                 255

Thr Val Trp Leu Ser Ala Ile Trp Met Met Trp Tyr Trp Gly Pro Ser
            260                 265                 270

Leu Tyr Ser Ile Val Ser Pro Phe Ile Pro Leu Leu Pro Ile Phe Phe
        275                 280                 285

Cys Leu Trp Val Tyr Ile Gly
        290                 295

<210> SEQ ID NO 58
<211> LENGTH: 1730
<212> TYPE: DNA
<213> ORGANISM: Artificial sequence
<220> FEATURE:
<223> OTHER INFORMATION: Recombinant antigenic insert peptide.

<400> SEQUENCE: 58
ggtaccgtcg acagcaaaag caggggataa ttctattaac catgaagact atcattgctt      60
ccatggcagc tgtcgttttc gtcccctatt aagataattg gtacttctga tagtaacgaa     120
tgagctacat tttctgtctg gttttcgccc aagaccttcc aggaaatgac aacaacagcg     180
actcgatgta aagacagac caaaagcggg ttctggaagg tcctttactg ttgttgtcgc     240
aattcatcac ctccggcttc ctgggccccc tgctggtcct gcaggccggg ttcttcctgc     300
ttaagtagtg gaggccgaag gacccggggg acgaccagga cgtccggccc aagaaggacg     360
tgacccgcat cctcaccatc cccagtccc tggactcgtg gtggacctcc ctcaactttc     420
actgggcgta ggagtggtag ggggtcaggg acctgagcac cacctggagg agttgaaag     480 tgggggggctc ccccgtgtgt ctgggccaga actcccagtc cccacctcc aaccactccc     540 accccccgag ggggcacaca gacccggtct tgagggtcag ggggtggagg ttggtgaggg     600
ccacctcctg ccccccatc tgccccggct accgctggat gtgcctgcgc cgcttcatca     660
ggtggaggac gggggggtag acggggccga tggcgaccta cacggacgcg gcgaagtagt     720
tcttcctgtt catcctgctg ctgtgcctga tcttcctgct ggtgctgctg gactaccagg     780
agaaggacaa gtaggacgac gacacggact agaaggacga ccacgacgac ctgatggtcc     840
```

```
gcatgctgcc cgtgtgcccc ctgatccccg gctccaccac cacctccacc ggcccctgca    900
cgtacgacgg gcacacgggg gactaggggc cgaggtggtg gtggaggtgg ccggggacgt    960
agacctgcac caccccgcc cagggcaact ccaagttccc ctcctgctgc tgcaccaagc   1020
tctggacgtg gtggggcgg gtcccgttga ggttcaaggg gaggacgacg acgtggttcg   1080
ccaccgacgg caactgcacc tgcatcaata ttaatgaaaa agaattattg gaattggata   1140
ggtggctgcc gttgacgtgg acgtagttat aattactttt tcttaataac cttaacctat   1200
aatgggcaag tttgtggaat tggtttgaca taacaaactg gctgtggtat ataagattat   1260
ttacccgttc aaacaccta accaaactgt attgtttgac cgacaccata tattctaata   1320
tcataatgat agtaggaggc ttgataggtt taagaatagt ttttgctgta ctttctatag   1380
agtattacta tcatcctccg aactatccaa attcttatca aaaacgacat gaaagatatc   1440
tagtgggcct gtcccccacc gtgtggctgt ccgccatctg gatgatgtgg tactggggcc   1500
atcaccggga caggggtgg cacaccgaca ggcggtagac ctactacacc atgaccccgg   1560
cctccctgta ctccatcgtg tccccttca tcccctgct gcccatcttc ttctgcctgt   1620
ggagggacat gaggtagcac aggggggaagt aggggggacga cgggtagaag aagacggaca   1680
gggtgtacat ctgactagtg agctccccac atgtagactg atcactcgag               1730
```

<210> SEQ ID NO 59  
<211> LENGTH: 271  
<212> TYPE: PRT  
<213> ORGANISM: Artificial sequence  
<220> FEATURE:  
<223> OTHER INFORMATION: Recombinant antigenic insert peptide construct.

<400> SEQUENCE: 59

```
Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Ile Thr Ser Gly
            20                  25                  30

Phe Leu Gly Pro Leu Leu Val Leu Gln Ala Gly Phe Phe Leu Leu Thr
        35                  40                  45

Arg Ile Leu Thr Ile Pro Gln Ser Leu Asp Ser Trp Trp Thr Ser Leu
    50                  55                  60

Asn Phe Leu Gly Gly Ser Pro Val Cys Leu Gly Gln Asn Ser Gln Ser
65                  70                  75                  80

Pro Thr Ser Asn His Ser Pro Thr Ser Cys Pro Pro Ile Cys Pro Gly
                85                  90                  95

Tyr Arg Trp Met Cys Leu Arg Arg Phe Ile Ile Phe Leu Phe Ile Leu
            100                 105                 110

Leu Leu Cys Leu Ile Phe Leu Leu Val Leu Leu Asp Tyr Gln Gly Met
        115                 120                 125

Leu Pro Val Cys Pro Leu Ile Pro Gly Ser Thr Thr Thr Ser Thr Gly
    130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Asn
                165                 170                 175

Ile Asn Glu Lys Glu Leu Leu Glu Leu Asp Lys Trp Ala Ser Leu Trp
            180                 185                 190

Asn Trp Phe Asp Ile Thr Asn Trp Leu Trp Tyr Ile Arg Leu Phe Ile
        195                 200                 205
```

```
Met Ile Val Gly Gly Leu Ile Gly Leu Arg Ile Val Phe Ala Val Leu
    210                 215                 220

Ser Ile Val Val Gly Leu Ser Pro Thr Val Trp Leu Ser Ala Ile Trp
225                 230                 235                 240

Met Met Trp Tyr Trp Gly Pro Ser Leu Tyr Ser Ile Val Ser Pro Phe
                245                 250                 255

Ile Pro Leu Leu Pro Ile Phe Phe Cys Leu Trp Val Tyr Ile Gly
        260                 265                 270

<210> SEQ ID NO 60
<211> LENGTH: 15
<212> TYPE: PRT
<213> ORGANISM: Human immunodeficiency virus

<400> SEQUENCE: 60

Asn Glu Lys Glu Leu Leu Glu Leu Asp Lys Trp Ala Ser Leu Trp
1               5                   10                  15

<210> SEQ ID NO 61
<211> LENGTH: 25
<212> TYPE: PRT
<213> ORGANISM: Human immunodeficiency virus

<400> SEQUENCE: 61

Asn Glu Lys Glu Leu Leu Glu Leu Asp Lys Trp Ala Ser Leu Trp Asn
1               5                   10                  15

Trp Phe Asp Ile Thr Asn Trp Leu Trp
            20                  25

<210> SEQ ID NO 62
<211> LENGTH: 300
<212> TYPE: PRT
<213> ORGANISM: Artificial sequence
<220> FEATURE:
<223> OTHER INFORMATION: Recombinant antigenic insert peptide construct.

<400> SEQUENCE: 62

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
            20                  25                  30

Leu Leu Glu Leu Asp Lys Trp Ala Ser Leu Trp Asn Trp Phe Asp Ile
            35                  40                  45

Thr Asn Trp Leu Trp Tyr Ile Arg Leu Phe Ile Met Ile Val Gly Gly
        50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
            100                 105                 110

Ser Cys Pro Pro Ile Cys Pro Gly Tyr Arg Trp Met Cys Leu Arg Arg
        115                 120                 125

Phe Ile Ile Phe Leu Phe Ile Leu Leu Leu Cys Leu Ile Phe Leu Leu
    130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
```

```
                165                 170                 175
Ala Gln Gly Asn Ser Lys Phe Pro Ser Cys Cys Cys Thr Lys Pro Thr
            180                 185                 190

Asp Gly Asn Cys Thr Cys Ile Ser Ile Asn Glu Lys Glu Leu Leu Glu
        195                 200                 205

Leu Asp Lys Trp Ala Ser Leu Trp Asn Trp Phe Asp Ile Thr Asn Trp
    210                 215                 220

Leu Trp Ser Ser Leu Trp Ala Ile Lys Tyr Leu Trp Glu Trp Ala Ser
225                 230                 235                 240

Val Arg Phe Ser Trp Leu Ser Leu Leu Val Pro Phe Val Gln Trp Phe
                245                 250                 255

Val Gly Leu Ser Pro Thr Val Trp Leu Ser Ala Ile Trp Met Met Trp
            260                 265                 270

Tyr Trp Gly Pro Ser Leu Tyr Ser Ile Val Ser Pro Phe Ile Pro Leu
        275                 280                 285

Leu Pro Ile Phe Ph

```
            225                 230                 235                 240
Ile Ala Phe Asn Gln Ser Ser Gly Gly Asp Pro Glu Ile Val Met His
                245                 250                 255

Ser Phe Asn Cys Gly Gly Glu Phe Phe Tyr Cys Asn Thr Ala Gln Leu
                260                 265                 270

Phe Asn Ser Thr Trp Asn Val Thr Gly Gly Thr Asn Thr Glu Gly
                275                 280                 285

Asn Asp Ile Ile Thr Leu Gln Cys Arg Ile Lys Gln Ile Ile Asn Met
                290                 295                 300

Trp Gln Lys Val Gly Lys Ala Met Tyr Ala Pro Pro Ile Thr Gly Gln
305                 310                 315                 320

Ile Arg Cys Ser Ser Asn Ile Thr Gly Leu Leu Leu Thr Arg Asp Gly
                325                 330                 335

Gly Asn Ser Thr Glu Thr Glu Thr Glu Ile Phe Arg Pro Gly Gly Gly
                340                 345                 350

Asp Met Arg Asp Asn Trp Arg Ser Glu Leu Tyr Lys Tyr Lys Val Val
                355                 360                 365

Arg Ile Glu Pro Ile Gly Val Ala Pro Thr Arg Ala Lys Arg
                370                 375                 380

<210> SEQ ID NO 64
<211> LENGTH: 337
<212> TYPE: PRT
<213> ORGANISM: Artificial sequence
<220> FEATURE:
<223> OTHER INFORMATION: Recombinant antigenic insert peptide construct.

<400> SEQUENCE: 64

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Asn Glu Lys Glu
                20                  25                  30

Leu Leu Glu Leu Asp Lys Trp Ala Ser Leu Trp Asn Trp Phe Asp Ile
                35                  40                  45

Thr Asn Trp Leu Trp Tyr Ile Arg Leu Phe Ile Met Ile Val Gly Gly
50                  55                  60

Leu Ile Gly Leu Arg Ile Val Phe Ala Val Leu Ser Ile Pro Gln Ser
65                  70                  75                  80

Leu Asp Ser Trp Trp Thr Ser Leu Asn Phe Leu Gly Gly Ser Pro Val
                85                  90                  95

Cys Leu Gly Gln Asn Ser Gln Ser Pro Thr Ser Asn His Ser Pro Thr
                100                 105                 110

Ser Cys Pro Pro Ile Cys Pro Gly Tyr Arg Trp Met Cys Leu Arg Arg
                115                 120                 125

Phe Ile Ile Phe Leu Phe Ile Leu Leu Leu Cys Leu Ile Phe Leu Leu
                130                 135                 140

Val Leu Leu Asp Tyr Gln Gly Met Leu Pro Val Cys Pro Leu Ile Pro
145                 150                 155                 160

Gly Ser Thr Thr Thr Ser Thr Gly Pro Cys Lys Thr Cys Thr Thr Pro
                165                 170                 175

Ala Gln Gly Asn Ser Lys Phe Pro Ser Cys Cys Cys Thr Lys Pro Thr
                180                 185                 190

Asp Gly Asn Cys Thr Cys Ile Ser Ile Asn Glu Lys Glu Leu Leu Glu
                195                 200                 205

Leu Asp Lys Trp Ala Ser Leu Trp Ala Ile Asn Glu Lys Glu Leu Leu
```

```
            210                 215                 220
Glu Leu Asp Lys Trp Ala Ser Leu Trp Ala Ile Asn Glu Lys Glu Leu
225                 230                 235                 240

Leu Glu Leu Asp Lys Trp Ala Ser Leu Trp Ala Ile Asn Glu Lys Glu
                245                 250                 255

Leu Leu Glu Leu Asp Lys Trp Ala Ser Leu Trp Ala Ile Lys Tyr Leu
                    260                 265                 270

Trp Glu Trp Ala Ser Val Arg Phe Ser Trp Leu Ser Leu Leu Val Pro
                275                 280                 285

Phe Val Gln Trp Phe Val Gly Leu Ser Pro Thr Val Trp Leu Ser Ala
            290                 295                 300

Ile Trp Met Met Trp Tyr Trp Gly Pro Ser Leu Tyr Ser Ile Val Ser
305                 310                 315                 320

Pro Phe Ile Pro Leu Leu Pro Ile Phe Phe Cys Leu Trp Val Tyr Ile
                325                 330                 335

Gly

<210> SEQ ID NO 65
<211> LENGTH: 313
<212> TYPE: PRT
<213> ORGANISM: Human immunodeficiency virus

<400> SEQUENCE: 65

Met Lys Thr Ile Ile Ala Leu Ser Tyr Ile Phe Cys Leu Val Phe Ala
1               5                   10                  15

Gln Asp Leu Pro Gly Asn Asp Asn Ser Glu Phe Ile Thr Ser Gly
                20                  25                  30

Phe Leu Gly Pro Leu Leu Val Leu Gln Ala Gly Phe Phe Leu Leu Thr
            35                  40                  45

Arg Ile Leu Thr Ile Pro Gln Ser Leu Asp Ser Trp Trp Thr Ser Leu
        50                  55                  60

Asn Phe Leu Gly Gly Ser Pro Val Cys Leu Gly Gln Asn Ser Gln Ser
65                  70                  75                  80

Pro Thr Ser Asn His Ser Pro Thr Ser Cys Pro Pro Ile Cys Pro Gly
                85                  90                  95

Tyr Arg Trp Met Cys Leu Arg Arg Phe Ile Ile Phe Leu Phe Ile Leu
                100                 105                 110

Leu Leu Cys Leu Ile Phe Leu Leu Val Leu Leu Asp Tyr Gln Gly Met
            115                 120                 125

Leu Pro Val Cys Pro Leu Ile Pro Gly Ser Thr Thr Thr Ser Thr Gly
        130                 135                 140

Pro Cys Lys Thr Cys Thr Thr Pro Ala Gln Gly Asn Ser Lys Phe Pro
145                 150                 155                 160

Ser Cys Cys Cys Thr Lys Pro Thr Asp Gly Asn Cys Thr Cys Ile Ser
                165                 170                 175

Ile Asn Glu Lys Glu Leu Leu Glu Leu Asp Lys Trp Ala Ser Leu Trp
                180                 185                 190

Ala Ile Asn Glu Lys Glu Leu Leu Glu Leu Asp Lys Trp Ala Ser Leu
            195                 200                 205

Trp Ala Ile Asn Glu Lys Glu Leu Leu Glu Leu Asp Lys Trp Ala Ser
        210                 215                 220

Leu Trp Ala Ile Asn Glu Lys Glu Leu Leu Glu Leu Asp Lys Trp Ala
225                 230                 235                 240

Ser Leu Trp Ala Ile Lys Tyr Leu Trp Glu Trp Ala Ser Val Arg Phe
```

```
                         245                 250                 255
Ser Trp Leu Ser Leu Leu Val Pro Phe Val Gln Trp Phe Val Gly Leu
            260                 265                 270

Ser Pro Thr Val Trp Leu Ser Ala Ile Trp Met Met Trp Tyr Trp Gly
            275                 280                 285

Pro Ser Leu Tyr Ser Ile Val Ser Pro Phe Ile Pro Leu Leu Pro Ile
            290                 295                 300

Phe Phe Cys Leu Trp Val Tyr Ile Gly
305                 310

<210> SEQ ID NO 66
<211> LENGTH: 373
<212> TYPE: PRT
<213> ORGANISM: Human immunodeficiency virus

<400> SEQUENCE: 66

Val Pro Val Trp Arg Glu Ala Thr Thr Thr Leu Phe Cys Ala Ser Asp
1               5                   10                  15

Ala Lys Ala Tyr Asp Thr Glu Val His Asn Val Trp Ala Thr His Ala
            20                  25                  30

Cys Val Pro Thr Asp Pro Asn Pro Gln Glu Val Val Leu Gly Asn Val
            35                  40                  45

Thr Glu Asn Phe Asn Met Trp Lys Asn Asn Met Val Asp Gln Met His
50                  55                  60

Glu Asp Ile Ile Ser Leu Trp Asp Glu Ser Leu Lys Pro Cys Val Lys
65                  70                  75                  80

Leu Thr Pro Leu Ser Val Gln Ala Cys Pro Lys Val Ser Phe Gln Pro
            85                  90                  95

Ile Pro Ile His Tyr Cys Val Pro Ala Gly Phe Ala Met Leu Lys Cys
            100                 105                 110

Asn Asn Lys Thr Phe Asn Gly Ser Gly Pro Cys Thr Asn Val Ser Thr
            115                 120                 125

Val Gln Cys Thr His Gly Ile Arg Pro Val Val Ser Thr Gln Leu Leu
            130                 135                 140

Leu Asn Gly Ser Leu Ala Glu Glu Asp Ile Val Ile Arg Ser Glu Asn
145                 150                 155                 160

Phe Thr Asp Asn Ala Lys Thr Ile Ile Val Gln Leu Asn Glu Ser Val
            165                 170                 175

Val Ile Asn Cys Thr Arg Pro Asn Asn Asn Thr Arg Arg Arg Leu Ser
            180                 185                 190

Ile Gly Pro Gly Arg Ala Phe Tyr Ala Arg Arg Asn Ile Ile Gly Asp
            195                 200                 205

Ile Arg Gln Ala His Cys Asn Ile Ser Arg Ala Lys Trp Asn Asn Thr
            210                 215                 220

Leu Gln Gln Ile Val Ile Lys Leu Arg Glu Lys Phe Arg Asn Lys Thr
225                 230                 235                 240

Ile Ala Phe Asn Gln Ser Ser Gly Gly Asp Pro Glu Ile Val Met His
            245                 250                 255

Ser Phe Asn Cys Gly Gly Glu Phe Phe Tyr Cys Asn Thr Ala Gln Leu
            260                 265                 270

Phe Asn Ser Thr Trp Asn Val Thr Gly Gly Thr Asn Gly Thr Glu Gly
            275                 280                 285

Asn Asp Ile Ile Thr Leu Gln Cys Arg Ile Lys Gln Leu Ala Met Tyr
            290                 295                 300
```

```
Ala Pro Pro Ile Thr Gly Gln Ile Arg Cys Ser Ser Asn Ile Thr Gly
305                 310                 315                 320

Leu Leu Leu Thr Arg Asp Gly Asn Ser Thr Glu Thr Glu Thr Glu
            325                 330                 335

Ile Phe Arg Pro Gly Gly Gly Asp Met Arg Asp Asn Trp Arg Ser Glu
            340                 345                 350

Leu Tyr Lys Tyr Lys Val Val Arg Ile Glu Pro Ile Gly Val Ala Pro
        355                 360                 365

Thr Arg Ala Lys Arg
    370
```

<210> SEQ ID NO 67
<211> LENGTH: 664
<212> TYPE: PRT
<213> ORGANISM: Human immunodeficiency virus

<400> SEQUENCE: 67

```
Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
            85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Met Cys Leu Arg Arg Phe Ile Ile Phe Leu Phe Ile
    130                 135                 140

Leu Leu Leu Cys Leu Ile Phe Leu Leu Val Leu Leu Asp Tyr Gln Gly
145                 150                 155                 160

Met Leu Pro Val Cys Pro Leu Ile Pro Gly Ser Thr Thr Thr Ser Thr
            165                 170                 175

Gly Pro Cys Lys Thr Cys Thr Thr Pro Ala Gln Gly Asn Ser Lys Phe
            180                 185                 190

Pro Ser Cys Cys Cys Thr Lys Pro Thr Asp Gly Asn Cys Thr Cys Ile
        195                 200                 205

Pro Ile Pro Ser Ser Trp Ala Phe Ala Lys Tyr Leu Trp Glu Trp Ala
    210                 215                 220

Ser Val Arg Phe Ser Trp Leu Ser Leu Leu Val Pro Phe Val Gln Trp
225                 230                 235                 240

Phe Val Gly Leu Ser Pro Thr Val Trp Leu Ser Ala Ile Trp Met Met
            245                 250                 255

Trp Tyr Trp Gly Pro Ser Leu Tyr Ser Ile Val Ser Pro Phe Ile Pro
            260                 265                 270

Leu Leu Pro Ile Phe Phe Cys Leu Trp Val Tyr Ile Gly Val Pro Val
        275                 280                 285

Trp Lys Glu Ala Thr Thr Thr Leu Phe Cys Ala Ser Asp Ala Lys Ala
    290                 295                 300
```

Tyr Asp Thr Glu Val His Asn Val Trp Ala Thr His Ala Cys Val Pro
305                 310                 315                 320

Thr Asp Pro Asn Pro Gln Glu Val Val Leu Glu Asn Val Thr Glu His
            325                 330                 335

Phe Asn Met Trp Lys Asn Asn Met Val Glu Gln Met Gln Glu Asp Ile
        340                 345                 350

Ile Ser Leu Trp Asp Gln Ser Leu Lys Pro Cys Val Lys Leu Thr Pro
    355                 360                 365

Leu Gln Ala Cys Pro Lys Ile Ser Phe Glu Pro Ile Pro Ile His Tyr
370                 375                 380

Cys Ala Pro Ala Gly Phe Ala Ile Leu Lys Cys Asn Asp Lys Thr Phe
385                 390                 395                 400

Asn Gly Lys Gly Pro Cys Lys Asn Val Ser Thr Val Gln Cys Thr His
                405                 410                 415

Gly Ile Arg Pro Val Val Ser Thr Gln Leu Leu Asn Gly Ser Leu
            420                 425                 430

Ala Glu Glu Glu Val Val Ile Arg Ser Asp Asn Phe Thr Asn Asn Ala
            435                 440                 445

Lys Thr Ile Ile Val Gln Leu Lys Glu Ser Val Glu Ile Asn Cys Thr
450                 455                 460

Arg Pro Asn Asn Asn Thr Arg Lys Ser Ile His Ile Gly Pro Gly Arg
465                 470                 475                 480

Ala Phe Tyr Thr Thr Gly Glu Ile Ile Gly Asp Ile Arg Gln Ala His
                485                 490                 495

Cys Asn Ile Ser Arg Ala Lys Trp Asn Asp Thr Leu Lys Gln Ile Val
            500                 505                 510

Ile Lys Leu Arg Glu Gln Phe Glu Asn Lys Thr Ile Val Phe Asn His
        515                 520                 525

Ser Ser Gly Gly Asp Pro Glu Ile Val Met His Ser Phe Asn Cys Gly
    530                 535                 540

Gly Glu Phe Phe Tyr Cys Asn Ser Thr Gln Leu Phe Asn Ser Thr Trp
545                 550                 555                 560

Asn Asn Asn Thr Glu Gly Ser Asn Asn Thr Gly Asn Thr Ile Thr
                565                 570                 575

Leu Pro Cys Arg Ile Lys Gln Leu Ala Met Tyr Ala Pro Pro Ile Arg
            580                 585                 590

Gly Gln Ile Arg Cys Ser Ser Asn Ile Thr Gly Leu Leu Leu Thr Arg
                595                 600                 605

Asp Gly Gly Ile Asn Glu Asn Gly Thr Glu Ile Phe Arg Pro Gly Gly
            610                 615                 620

Gly Asp Met Arg Asp Asn Trp Arg Ser Glu Leu Tyr Lys Tyr Lys Val
625                 630                 635                 640

Val Lys Ile Glu Pro Leu Gly Val Ala Pro Thr Lys Ala Lys Arg Leu
                645                 650                 655

Val Ala Ala Ala Phe Glu Ser Arg
                660

<210> SEQ ID NO 68
<211> LENGTH: 2000
<212> TYPE: DNA
<213> ORGANISM: Human immunodeficiency virus

<400> SEQUENCE: 68
ggattattca taccgtccca ccatcgggcg cggatcccgg tccgaagcgc gcggaattca    60

```
aaggcctacg tcgacagcaa aagcagggga taattctatt aaccatgaag actatcattg    120
ctttgagcta cattttatgt ctggttctcg ctcaaaaact tcccggaaat gacaacaaca    180
gcgaattcat cacctccggc ttcctgggcc cctgctggt gctgcaggcc ggcttcttcc     240
tgctgacccg catcctgacc atcccccagt ccctggactc ctggtggacc tccctgaact    300
tcctgggcgg ctccccgtg tgcctgggcc agaactccca gtcccccacc tccaaccact     360
cccccacctc ctgcccccccc atctgcccg gctaccgctg gatgtgcctg cgccgcttca    420
tcatcttcct gttcatcctg ctgctgtgcc tgatcttcct gctggtgctg ctggactacc    480
agggcatgct gcccgtgtgc ccctgatcc cggctccac caccacctcc accgccccct    540
gcaagacctg caccacccccc gcccagggca actccaagtt cccctcctgc tgctgcacca    600
agcccaccga cggcaactgc acctgcatcc ccatccctc ctcctgggcc ttcgccaagt     660
acctgtggga gtgggcctcc gtgcgcttct cctggctgtc cctgctggtg cccttcgtgc    720
agtggttcgt gggcctgtcc ccaccgtgt ggctgtccgc catctggatg atgtggtact     780
ggggcccctc cctgtactcc atcgtgtccc ccttcatccc cctgctgccc atcttcttct    840
gcctgtgggt gtacatcggg gtacctgtgt ggaaagaagc aaccaccact ctatttttgtg   900 catcagatgc taaagcatat gatacagagg tacataatgt ttgggccaca catgcctgtg    960
tacccacaga ccccaaccca caagaagtag tattggaaaa tgtaacagaa catttttaaca   1020 tgtggaaaaa taacatggta gaacagatgc aggaggatat aatcagttta tgggatcaaa    1080
gcctaaagcc atgtgtaaaa ttaaccccac tccaggcctg tccaaagata tcctttgagc    1140
caattcccat acattattgt gccccggctg gttttgcgat tctaaagtgt aatgataaga    1200
cgttcaatgg aaaaggacca tgtaaaaatg tcagcacagt acaatgtaca catggaatta    1260
ggccagtagt atcaactcaa ctgctgctaa atggcagtct agcagaagaa gaggtagtaa    1320
ttagatctga caatttcacg aacaatgcta aaaccataat agtacagctg aaagaatctg    1380
tagaaattaa ttgtacaaga cccaacaaca atacaagaaa aagtatacat ataggaccag    1440
ggagagcatt ttatactaca ggagaaataa taggagatat aagacaagca cattgtaaca    1500
ttagtagagc aaaatggaat gacactttaa acagatagt tataaaatta agagaacaat    1560
ttgagaataa aacaatagtc tttaatcact cctcaggagg ggacccagaa attgtaatgc    1620
acagttttaa ttgtggagga gaatttttct actgtaattc aacacaactg tttaatagta    1680
cttggaataa taatactgaa gggtcaaata cactgaagg aaatactatc acactcccat     1740
gcagaataaa acagctagca atgtatgccc ctcccatcag aggacaaatt agatgttcat    1800
caaatattac agggctgcta ttaacaagag atggtggtat taatgagaat gggaccgaga    1860
tcttcagacc tggaggagga gatatgaggg acaattggag aagtgaatta tataaatata    1920
aagtagtaaa aattgaacca ttaggagtag cacccaccaa ggcaagaga tgactagtcg     1980 cggccgcttt cgaatctaga                                                2000

<210> SEQ ID NO 69
<211> LENGTH: 665
<212> TYPE: PRT
<213> ORGANISM: Human immunodeficiency virus

<400> SEQUENCE: 69

Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
```

```
            20                  25                  30
Leu Thr Met Lys Thr Ile Ile Ala Leu Ser Tyr Ile Leu Cys Leu Val
            35                  40                  45

Leu Ala Gln Lys Leu Pro Gly Asn Asp Asn Asn Ser Glu Phe Ile Thr
50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
                100                 105                 110

Gln Ser Pro Thr Ser Asn His Ser Pro Thr Ser Cys Pro Pro Ile Cys
            115                 120                 125

Pro Gly Tyr Arg Trp Met Cys Leu Arg Arg Phe Ile Ile Phe Leu Phe
            130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
                180                 185                 190

Phe Pro Ser Cys Cys Cys Thr Lys Pro Thr Asp Gly Asn Cys Thr Cys
            195                 200                 205

Ile Pro Ile Pro Ser Ser Trp Ala Phe Ala Lys Tyr Leu Trp Glu Trp
            210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
                260                 265                 270

Pro Leu Leu Pro Ile Phe Phe Cys Leu Trp Val Tyr Ile Gly Val Pro
            275                 280                 285

Val Trp Lys Glu Ala Thr Thr Thr Leu Phe Cys Ala Ser Asp Ala Lys
            290                 295                 300

Ala Tyr Asp Thr Glu Val His Asn Val Trp Ala Thr His Ala Cys Val
305                 310                 315                 320

Pro Thr Asp Pro Asn Pro Gln Glu Val Val Leu Glu Asn Val Thr Glu
                325                 330                 335

Asn Phe Asn Met Trp Lys Asn Asn Met Val Gln Met His Glu Asp
                340                 345                 350

Ile Ile Ser Leu Trp Asp Gln Ser Leu Lys Pro Cys Val Lys Leu Thr
            355                 360                 365

Pro Leu Gln Ala Cys Pro Lys Val Ser Phe Glu Pro Ile Pro Ile His
            370                 375                 380

Tyr Cys Thr Pro Ala Gly Phe Ala Ile Leu Lys Cys Lys Asp Lys Lys
385                 390                 395                 400

Phe Asn Gly Thr Gly Pro Cys Lys Asn Val Ser Thr Val Gln Cys Thr
                405                 410                 415

His Gly Ile Arg Pro Val Val Ser Thr Gln Leu Leu Leu Asn Gly Ser
            420                 425                 430

Leu Ala Glu Glu Glu Val Val Ile Arg Ser Ser Asn Phe Thr Asp Asn
            435                 440                 445
```

```
Ala Lys Asn Ile Ile Val Gln Leu Lys Glu Ser Val Glu Ile Asn Cys
    450                 455                 460
Thr Arg Pro Asn Asn Asn Thr Arg Lys Ser Ile His Ile Gly Pro Gly
465                 470                 475                 480
Arg Ala Phe Tyr Thr Thr Gly Glu Ile Ile Gly Asp Ile Arg Gln Ala
                485                 490                 495
His Cys Asn Ile Ser Arg Thr Lys Trp Asn Asn Thr Leu Asn Gln Ile
                    500                 505                 510
Ala Thr Lys Leu Lys Glu Gln Phe Gly Asn Asn Lys Thr Ile Val Phe
            515                 520                 525
Asn Gln Ser Ser Gly Gly Asp Pro Glu Ile Val Met His Ser Phe Asn
            530                 535                 540
Cys Gly Gly Glu Phe Phe Tyr Cys Asn Ser Thr Gln Leu Phe Asn Ser
545                 550                 555                 560
Thr Trp Asn Phe Asn Gly Thr Trp Asn Leu Thr Gln Ser Asn Gly Thr
                565                 570                 575
Glu Gly Asn Asp Thr Ile Thr Leu Pro Cys Arg Ile Lys Gln Leu Ala
                580                 585                 590
Met Tyr Ala Pro Pro Ile Arg Gly Gln Ile Arg Cys Ser Ser Asn Ile
            595                 600                 605
Thr Gly Leu Ile Leu Thr Arg Asp Gly Gly Asn Asn His Asn Asn Asp
610                 615                 620
Thr Glu Thr Phe Arg Pro Gly Gly Gly Asp Met Arg Asp Asn Trp Arg
625                 630                 635                 640
Ser Glu Leu Tyr Lys Tyr Lys Val Val Lys Ile Glu Pro Leu Gly Val
                645                 650                 655
Ala Pro Thr Lys Ala Lys Arg Leu Val
            660                 665

<210> SEQ ID NO 70
<211> LENGTH: 2000
<212> TYPE: DNA
<213> ORGANISM: Human immunodeficiency virus

<400> SEQUENCE: 70
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta cattttatgt ctggttctcg ctcaaaaact tcccggaaat gacaacaaca     180
gcgaattcat cacctccggc ttcctgggcc cctgctggt gctgcaggcc ggcttcttcc      240
tgctgacccg catcctgacc atccccagt ccctggactc ctggtggacc tccctgaact     300
tcctgggcgg ctccccgtg tgcctgggcc agaactccca gtcccccacc tccaaccact     360
cccccacctc ctgccccccc atctgccccg ctaccgctg atgtgcctg cgccgcttca      420 tcatcttcct gttcatcctg ctgctgtgcc tgatcttcct gctggtgctg ctggactacc     480
agggcatgct gcccgtgtgc ccctgatcc ccggctccac caccacctcc accggcccct     540
gcaagacctg caccaccccc gcccagggca actccaagtt ccctcctgc tgctgcacca     600 agcccaccga cggcaactgc acctgcatcc ccatcccctc ctcctgggcc ttcgccaagt     660
acctgtggga gtgggcctcc gtgcgcttct cctggctgtc cctgctggtg cccttcgtgc     720
agtggttcgt gggcctgtcc cccaccgtgt ggctgtccgc catctggatg atgtggtact     780
ggggcccctc cctgtactcc atcgtgtccc ccttcatccc cctgctgccc atcttcttct     840
```

```
gcctgtgggt gtacatcggg gtacctgtgt ggaaagaagc aaccaccact ctattttgtg    900
catcagatgc taaagcatat gatacagagg tacataatgt ttgggccaca catgcctgtg    960
tacccacaga ccccaaccca caagaagtag tattggaaaa tgtgacagaa aattttaaca   1020
tgtggaaaaa taacatggta gaacagatgc atgaggatat aatcagttta tgggatcaaa   1080
gcctaaagcc atgtgtaaaa ttaaccccac tccaggcctg tccaaggta tcctttgagc    1140 caattcccat acattattgt accccggctg gttttgcgat tctaaagtgt aaagacaaga   1200
agttcaatgg aacagggcca tgtaaaaatg tcagcacagt acaatgtaca catggaatta   1260
ggccagtagt gtcaactcaa ctgctgttaa atggcagtct agcagaagaa gaggtagtaa   1320
ttagatctag taatttcaca gacaatgcaa aaaacataat agtacagttg aaagaatctg   1380
tagaaattaa ttgtacaaga cccaacaaca atacaaggaa aagtatacat ataggaccag   1440
gaagagcatt ttatacaaca ggagaaataa taggagatat aagacaagca cattgcaaca   1500
ttagtagaac aaaatggaat aacactttaa atcaaatagc tacaaaatta aaagaacaat   1560
ttgggaataa taaaacaata gtctttaatc aatcctcagg aggggaccca gaaattgtaa   1620
tgcacagttt taattgtgga ggggaatttt tctactgtaa ttcaacacaa ctgttttaata   1680 gtacttggaa ttttaatggt acttggaatt taacacaatc gaatggtact gaaggaaatg   1740
acactatcac actcccatgt agaataaaac agctagcaat gtatgcccct cccatcagag   1800
gacaaattag atgctcatca atattacagg gctaatatt aacaagagat ggtggaaata   1860
accacaataa tgataccgag acctttagac ctggaggagg agatatgagg gacaattgga   1920
gaagtgaatt atataaatat aaagtagtaa aaattgaacc attaggagta gcacccacca   1980
aggcaaaaag atgactagtc                                              2000
```

<210> SEQ ID NO 71
<211> LENGTH: 665
<212> TYPE: PRT
<213> ORGANISM: Human immunodeficiency virus

<400> SEQUENCE: 71

Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
    130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser

-continued

```
                165                 170                 175
Thr Gly Pro Cys Lys Thr Cys Thr Thr Pro Ala Gln Gly Asn Ser Lys
            180                 185                 190

Phe Pro Ser Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
    210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
                260                 265                 270

Pro Leu Leu Pro Ile Phe Phe Cys Leu Trp Val Tyr Ile Gly Val Pro
            275                 280                 285

Val Trp Lys Glu Ala Thr Thr Thr Leu Phe Cys Ala Ser Asp Ala Lys
        290                 295                 300

Ala Tyr Asp Thr Glu Val His Asn Val Trp Ala Thr His Ala Cys Val
305                 310                 315                 320

Pro Thr Asp Pro Asn Pro Gln Glu Val Glu Leu Asn Val Thr Glu
                325                 330                 335

Asn Phe Asn Met Trp Lys Asn Asn Met Val Glu Gln Met His Glu Asp
            340                 345                 350

Ile Ile Ser Leu Trp Asp Gln Ser Leu Lys Pro Cys Val Lys Leu Thr
                355                 360                 365

Pro Leu Gln Ala Cys Pro Lys Ile Ser Phe Glu Pro Ile Pro Ile His
    370                 375                 380

Tyr Cys Ala Pro Ala Gly Phe Ala Ile Leu Lys Cys Lys Asp Lys Lys
385                 390                 395                 400

Phe Asn Gly Lys Gly Pro Cys Ser Asn Val Ser Thr Val Gln Cys Thr
                405                 410                 415

His Gly Ile Arg Pro Val Val Ser Thr Gln Leu Leu Leu Asn Gly Ser
            420                 425                 430

Leu Ala Glu Glu Glu Val Val Ile Arg Ser Glu Asn Phe Ala Asp Asn
        435                 440                 445

Ala Lys Thr Ile Ile Val Gln Leu Asn Glu Ser Val Glu Ile Asn Cys
    450                 455                 460

Thr Arg Pro Asn Asn Asn Thr Arg Lys Ser Ile His Ile Gly Pro Gly
465                 470                 475                 480

Arg Ala Leu Tyr Thr Thr Gly Glu Ile Ile Gly Asp Ile Arg Gln Ala
                485                 490                 495

His Cys Asn Leu Ser Arg Ala Lys Trp Asn Asp Thr Leu Asn Lys Ile
            500                 505                 510

Val Ile Lys Leu Arg Glu Gln Phe Gly Asn Lys Thr Ile Val Phe Lys
        515                 520                 525

His Ser Ser Gly Gly Asp Pro Glu Ile Val Thr His Ser Phe Asn Cys
    530                 535                 540

Gly Gly Glu Phe Phe Tyr Cys Asn Ser Thr Gln Leu Phe Asn Ser Thr
545                 550                 555                 560

Trp Asn Val Thr Glu Glu Ser Asn Asn Thr Val Glu Asn Asn Thr Ile
                565                 570                 575

Thr Leu Pro Cys Arg Ile Lys Gln Leu Ala Met Tyr Ala Pro Pro Ile
            580                 585                 590
```

```
Arg Gly Gln Ile Arg Cys Ser Ser Asn Ile Thr Gly Leu Leu Leu Thr
        595                 600                 605

Arg Asp Gly Gly Pro Glu Asp Asn Lys Thr Glu Val Phe Arg Pro Gly
    610                 615                 620

Gly Gly Asp Met Arg Asp Asn Trp Arg Ser Glu Leu Tyr Lys Tyr Lys
625                 630                 635                 640

Val Val Lys Ile Glu Pro Leu Gly Val Ala Pro Thr Lys Ala Lys Arg
                645                 650                 655

Leu Val Ala Ala Ala Phe Glu Ser Arg
            660                 665

<210> SEQ ID NO 72
<211> LENGTH: 2000
<212> TYPE: PRT
<213> ORGANISM: Human immunodeficiency virus

<400> SEQUENCE: 72

Gly Gly Ala Thr Thr Ala Thr Thr Cys Ala Thr Ala Cys Cys Gly Thr
1               5                   10                  15

Cys Cys Cys Ala Cys Cys Ala Thr Cys Gly Gly Gly Cys Gly Cys Gly
            20                  25                  30

Gly Ala Thr Cys Cys Cys Gly Gly Thr Cys Cys Gly Ala Ala Gly Cys
        35                  40                  45

Gly Cys Gly Cys Gly Gly Ala Ala Thr Thr Cys Ala Ala Ala Gly Gly
    50                  55                  60

Cys Cys Thr Ala Cys Gly Thr Cys Gly Ala Cys Ala Gly Cys Ala Ala
65                  70                  75                  80

Ala Ala Gly Cys Ala Gly Gly Gly Gly Ala Thr Ala Ala Thr Thr Cys
                85                  90                  95

Thr Ala Thr Thr Ala Ala Cys Cys Ala Thr Gly Ala Ala Gly Ala Cys
            100                 105                 110

Thr Ala Thr Cys Ala Thr Thr Gly Cys Thr Thr Thr Gly Ala Gly Cys
        115                 120                 125

Thr Ala Cys Ala Thr Thr Thr Thr Ala Thr Gly Thr Cys Thr Gly Gly
    130                 135                 140

Thr Thr Cys Thr Cys Gly Cys Thr Cys Ala Ala Ala Ala Ala Cys Thr
145                 150                 155                 160

Thr Cys Cys Cys Gly Gly Ala Ala Ala Thr Gly Ala Cys Ala Ala Cys
                165                 170                 175

Ala Ala Cys Ala Gly Cys Gly Ala Ala Thr Thr Cys Ala Thr Cys Ala
            180                 185                 190

Cys Cys Thr Cys Cys Gly Gly Cys Thr Thr Cys Cys Thr Gly Gly Gly
        195                 200                 205

Cys Cys Cys Cys Cys Thr Gly Cys Thr Gly Gly Thr Gly Cys Thr Gly
    210                 215                 220

Cys Ala Gly Gly Cys Cys Gly Gly Cys Thr Thr Cys Thr Thr Cys Cys
225                 230                 235                 240

Thr Gly Cys Thr Gly Ala Cys Cys Cys Gly Cys Ala Thr Cys Cys Thr
                245                 250                 255

Gly Ala Cys Cys Ala Thr Cys Cys Cys Cys Cys Ala Gly Thr Cys Cys
            260                 265                 270

Cys Thr Gly Gly Ala Cys Thr Cys Cys Thr Gly Gly Thr Gly Gly Ala
        275                 280                 285

Cys Cys Thr Cys Cys Cys Thr Gly Ala Ala Cys Thr Thr Cys Cys Thr
```

```
                290                 295                 300
Gly Gly Gly Cys Gly Gly Cys Thr Cys Cys Cys Cys Gly Thr Gly
305                 310                 315                 320

Thr Gly Cys Cys Thr Gly Gly Cys Ala Gly Ala Ala Cys Thr
                325                 330                 335

Cys Cys Cys Ala Gly Thr Cys Cys Cys Cys Ala Cys Cys Thr Cys
                340                 345                 350

Cys Ala Ala Cys Cys Ala Cys Thr Cys Cys Cys Cys Ala Cys Cys
                355                 360                 365

Thr Cys Cys Thr Gly Cys Cys Cys Cys Cys Ala Thr Cys Thr
370                 375                 380

Gly Cys Cys Cys Cys Gly Gly Cys Thr Ala Cys Cys Gly Cys Thr Gly
385                 390                 395                 400

Gly Ala Thr Gly Thr Gly Cys Cys Thr Gly Cys Gly Cys Cys Gly Cys
                405                 410                 415

Thr Thr Cys Ala Thr Cys Ala Thr Cys Thr Thr Cys Cys Thr Gly Thr
                420                 425                 430

Thr Cys Ala Thr Cys Cys Thr Gly Cys Thr Gly Cys Thr Gly Thr
                435                 440                 445

Cys Cys Thr Gly Ala Thr Cys Thr Thr Cys Cys Thr Gly Cys Thr Gly
450                 455                 460

Gly Thr Gly Cys Thr Gly Cys Thr Gly Gly Ala Cys Thr Ala Cys Cys
465                 470                 475                 480

Ala Gly Gly Gly Cys Ala Thr Gly Cys Thr Gly Cys Cys Gly Thr
                485                 490                 495

Gly Thr Gly Cys Cys Cys Cys Thr Gly Ala Thr Cys Cys Cys
                500                 505                 510

Gly Gly Cys Thr Cys Cys Ala Cys Cys Ala Cys Ala Cys Cys Thr
                515                 520                 525

Cys Cys Ala Cys Cys Gly Gly Cys Cys Cys Cys Thr Gly Cys Ala Ala
                530                 535                 540

Gly Ala Cys Cys Thr Gly Cys Ala Cys Ala Cys Cys Cys Cys
545                 550                 555                 560

Gly Cys Cys Cys Ala Gly Gly Cys Ala Ala Cys Thr Cys Cys Ala
                565                 570                 575

Ala Gly Thr Thr Cys Cys Cys Cys Thr Cys Cys Thr Gly Cys Thr Gly
                580                 585                 590

Cys Thr Gly Cys Ala Cys Cys Ala Ala Gly Cys Cys Cys Ala Cys Cys
                595                 600                 605

Gly Ala Cys Gly Gly Cys Ala Ala Cys Thr Gly Cys Ala Cys Cys Thr
                610                 615                 620

Gly Cys Ala Thr Cys Cys Cys Cys Ala Thr Cys Cys Cys Cys Thr Cys
625                 630                 635                 640

Cys Thr Cys Cys Thr Gly Gly Gly Cys Cys Thr Thr Cys Gly Cys Cys
                645                 650                 655

Ala Ala Gly Thr Ala Cys Cys Thr Gly Thr Gly Gly Ala Gly Thr
                660                 665                 670

Gly Gly Gly Cys Cys Thr Cys Cys Gly Thr Gly Cys Gly Cys Thr Thr
                675                 680                 685

Cys Thr Cys Cys Thr Gly Gly Cys Thr Gly Cys Cys Cys Thr Gly
                690                 695                 700

Cys Thr Gly Gly Thr Gly Cys Cys Cys Thr Thr Cys Gly Thr Gly Cys
705                 710                 715                 720
```

-continued

Ala Gly Thr Gly Gly Thr Thr Cys Gly Thr Gly Gly Cys Cys Thr
                725                 730                 735
Gly Thr Cys Cys Cys Cys Ala Cys Cys Gly Thr Gly Thr Gly Gly
                740                 745                 750
Cys Thr Gly Thr Cys Cys Gly Cys Cys Ala Thr Cys Thr Gly Gly Ala
                755                 760                 765
Thr Gly Ala Thr Gly Thr Gly Gly Thr Ala Cys Thr Gly Gly Gly Gly
                770                 775                 780
Cys Cys Cys Cys Thr Cys Cys Thr Gly Thr Ala Cys Thr Cys Cys
785                 790                 795                 800
Ala Thr Cys Gly Thr Gly Thr Cys Cys Cys Thr Cys Thr Cys Ala
                805                 810                 815
Thr Cys Cys Cys Cys Cys Thr Gly Cys Thr Gly Cys Cys Ala Thr
                820                 825                 830
Cys Thr Thr Cys Thr Thr Cys Thr Gly Cys Cys Thr Gly Thr Gly Gly
                835                 840                 845
Gly Thr Gly Thr Ala Cys Ala Thr Cys Gly Gly Gly Gly Thr Ala Cys
                850                 855                 860
Cys Thr Gly Thr Gly Thr Gly Gly Ala Ala Ala Gly Ala Ala Gly Cys
865                 870                 875                 880
Ala Ala Cys Cys Ala Cys Cys Ala Cys Thr Cys Thr Ala Thr Thr
                885                 890                 895
Thr Gly Thr Gly Cys Ala Thr Cys Ala Gly Ala Thr Gly Cys Thr Ala
                900                 905                 910
Ala Ala Gly Cys Ala Thr Ala Thr Gly Ala Thr Ala Cys Ala Gly Ala
                915                 920                 925
Gly Gly Thr Ala Cys Ala Thr Ala Ala Thr Gly Thr Thr Thr Gly Gly
                930                 935                 940
Gly Cys Cys Ala Cys Ala Cys Ala Thr Gly Cys Cys Thr Gly Thr Gly
945                 950                 955                 960
Thr Ala Cys Cys Cys Ala Cys Ala Gly Ala Cys Cys Cys Cys Ala Ala
                965                 970                 975
Cys Cys Cys Ala Cys Ala Ala Gly Ala Ala Gly Thr Ala Gly Ala Ala
                980                 985                 990
Thr Thr Gly Gly Ala Ala Ala Ala Thr Gly Thr Gly Ala Cys Ala Gly
                995                1000                1005
Ala Ala Ala Ala Thr Thr Thr Thr Ala Ala Cys Ala Thr Gly Thr
                1010                1015                1020
Gly Gly Ala Ala Ala Ala Ala Thr Ala Ala Cys Ala Thr Gly Gly
                1025                1030                1035
Thr Ala Gly Ala Ala Cys Ala Gly Ala Thr Gly Cys Ala Thr Gly
                1040                1045                1050
Ala Gly Gly Ala Thr Ala Thr Ala Ala Thr Cys Ala Gly Thr Thr
                1055                1060                1065
Thr Ala Thr Gly Gly Gly Ala Thr Cys Ala Ala Ala Gly Cys Cys
                1070                1075                1080
Thr Ala Ala Ala Gly Cys Cys Ala Thr Gly Thr Gly Thr Ala Ala
                1085                1090                1095
Ala Ala Thr Thr Ala Ala Cys Thr Cys Cys Ala Cys Thr Cys Cys
                1100                1105                1110
Ala Gly Gly Cys Cys Thr Gly Thr Cys Cys Ala Ala Ala Gly Ala
                1115                1120                1125

-continued

```
Thr Ala Thr Cys Cys Thr Thr Thr Gly Ala Gly Cys Cys Ala Ala
    1130                1135                1140

Thr Thr Cys Cys Cys Ala Thr Ala Cys Ala Thr Thr Ala Thr Thr
    1145                1150                1155

Gly Thr Gly Cys Cys Cys Gly Gly Cys Thr Gly Gly Thr Thr
    1160                1165                1170

Thr Thr Gly Cys Gly Ala Thr Thr Cys Thr Ala Ala Ala Gly Thr
    1175                1180                1185

Gly Thr Ala Ala Ala Gly Ala Thr Ala Ala Gly Ala Ala Gly Thr
    1190                1195                1200

Thr Cys Ala Ala Thr Gly Gly Ala Ala Ala Gly Gly Ala Cys
    1205                1210                1215

Cys Ala Thr Gly Thr Thr Cys Ala Ala Ala Thr Gly Thr Cys Ala
    1220                1225                1230

Gly Cys Ala Cys Ala Gly Thr Ala Cys Ala Ala Thr Gly Thr Ala
    1235                1240                1245

Cys Ala Cys Ala Thr Gly Gly Gly Ala Thr Thr Ala Gly Gly Cys
    1250                1255                1260

Cys Ala Gly Thr Ala Gly Thr Ala Thr Cys Ala Ala Cys Thr Cys
    1265                1270                1275

Ala Ala Cys Thr Gly Cys Thr Gly Thr Thr Ala Ala Ala Thr Gly
    1280                1285                1290

Gly Cys Ala Gly Thr Cys Thr Ala Gly Cys Ala Gly Ala Ala Gly
    1295                1300                1305

Ala Ala Gly Ala Gly Gly Thr Ala Gly Thr Ala Ala Thr Thr Ala
    1310                1315                1320

Gly Ala Thr Cys Cys Gly Ala Ala Ala Ala Thr Thr Thr Cys Gly
    1325                1330                1335

Cys Gly Gly Ala Cys Ala Ala Thr Gly Cys Thr Ala Ala Ala Ala
    1340                1345                1350

Cys Cys Ala Thr Ala Ala Thr Ala Gly Thr Ala Cys Ala Gly Cys
    1355                1360                1365

Thr Gly Ala Ala Thr Gly Ala Ala Thr Cys Thr Gly Thr Ala Gly
    1370                1375                1380

Ala Ala Ala Thr Thr Ala Ala Thr Thr Gly Thr Ala Cys Ala Ala
    1385                1390                1395

Gly Ala Cys Cys Cys Ala Ala Cys Ala Ala Cys Ala Ala Thr Ala
    1400                1405                1410

Cys Ala Ala Gly Ala Ala Ala Ala Ala Gly Thr Ala Thr Ala Cys
    1415                1420                1425

Ala Thr Ala Thr Ala Gly Gly Ala Cys Cys Ala Gly Gly Cys Ala
    1430                1435                1440

Gly Ala Gly Cys Ala Thr Thr Ala Thr Ala Thr Ala Cys Ala Ala
    1445                1450                1455

Cys Ala Gly Gly Ala Gly Ala Ala Ala Thr Ala Ala Thr Ala Gly
    1460                1465                1470

Gly Ala Gly Ala Thr Ala Thr Ala Ala Gly Ala Cys Ala Ala Gly
    1475                1480                1485

Cys Ala Cys Ala Thr Thr Gly Thr Ala Ala Cys Cys Thr Thr Ala
    1490                1495                1500

Gly Thr Ala Gly Ala Gly Cys Ala Ala Ala Ala Thr Gly Gly Ala
    1505                1510                1515

Ala Thr Gly Ala Cys Ala Cys Thr Thr Thr Ala Ala Ala Thr Ala
```

-continued

```
            1520                1525                1530
Ala Gly Ala Thr Ala Gly Thr Thr Ala Thr Ala Ala Ala Thr
        1535                1540                1545
Thr Ala Ala Gly Ala Gly Ala Ala Cys Ala Ala Thr Thr Thr Gly
    1550                1555                1560
Gly Gly Ala Ala Thr Ala Ala Ala Ala Cys Ala Ala Thr Ala Gly
    1565                1570                1575
Thr Cys Thr Thr Thr Ala Ala Gly Cys Ala Thr Thr Cys Cys Thr
    1580                1585                1590
Cys Ala Gly Gly Ala Gly Gly Gly Ala Cys Cys Cys Ala Gly
    1595                1600                1605
Ala Ala Ala Thr Thr Gly Thr Gly Ala Cys Gly Cys Ala Cys Ala
    1610                1615                1620
Gly Thr Thr Thr Thr Ala Ala Thr Thr Gly Thr Gly Gly Ala Gly
    1625                1630                1635
Gly Gly Gly Ala Ala Thr Thr Thr Thr Cys Thr Ala Cys Thr
    1640                1645                1650
Gly Thr Ala Ala Thr Thr Cys Ala Ala Cys Ala Cys Ala Ala Cys
    1655                1660                1665
Thr Gly Thr Thr Thr Ala Ala Thr Ala Gly Thr Ala Cys Thr Thr
    1670                1675                1680
Gly Gly Ala Ala Thr Gly Thr Thr Ala Cys Thr Gly Ala Ala Gly
    1685                1690                1695
Ala Gly Thr Cys Ala Ala Ala Thr Ala Ala Cys Ala Cys Thr Gly
    1700                1705                1710
Thr Ala Gly Ala Ala Ala Thr Ala Cys Ala Cys Ala Ala
    1715                1720                1725
Thr Cys Ala Cys Ala Cys Thr Cys Cys Cys Ala Thr Gly Cys Ala
    1730                1735                1740
Gly Ala Ala Thr Ala Ala Ala Cys Ala Gly Cys Thr Ala Gly
    1745                1750                1755
Cys Ala Ala Thr Gly Thr Ala Thr Gly Cys Cys Cys Cys Thr Cys
    1760                1765                1770
Cys Cys Ala Thr Cys Ala Gly Ala Gly Gly Ala Cys Ala Ala Ala
    1775                1780                1785
Thr Thr Ala Gly Ala Thr Gly Thr Thr Cys Ala Thr Cys Ala Ala
    1790                1795                1800
Ala Thr Ala Thr Thr Ala Cys Ala Gly Gly Gly Cys Thr Gly Cys
    1805                1810                1815
Thr Ala Thr Thr Ala Cys Ala Ala Gly Ala Gly Ala Thr Gly
    1820                1825                1830
Gly Thr Gly Gly Thr Cys Cys Ala Gly Ala Gly Gly Ala Cys Ala
    1835                1840                1845
Ala Cys Ala Ala Gly Ala Cys Cys Gly Ala Gly Gly Thr Cys Thr
    1850                1855                1860
Thr Cys Ala Gly Ala Cys Cys Thr Gly Gly Ala Gly Gly Ala Gly
    1865                1870                1875
Gly Ala Gly Ala Thr Ala Thr Gly Ala Gly Gly Gly Ala Cys Ala
    1880                1885                1890
Ala Thr Thr Gly Gly Ala Gly Ala Ala Gly Thr Gly Ala Ala Thr
    1895                1900                1905
Thr Ala Thr Ala Thr Ala Ala Ala Thr Ala Thr Ala Ala Ala Gly
    1910                1915                1920
```

```
Thr Ala Gly Thr Ala Ala Ala Ala Thr Thr Gly Ala Ala Cys
    1925            1930                1935

Cys Ala Thr Thr Ala Gly Gly Ala Gly Thr Ala Gly Cys Ala Cys
    1940            1945                1950

Cys Cys Ala Cys Cys Ala Ala Gly Gly Cys Ala Ala Ala Gly Ala
    1955            1960                1965

Gly Ala Thr Gly Ala Cys Thr Ala Gly Thr Cys Gly Cys Gly Gly
    1970            1975                1980

Cys Cys Gly Cys Thr Thr Thr Cys Gly Ala Ala Thr Cys Thr Ala
    1985            1990                1995

Gly Ala
    2000

<210> SEQ ID NO 73
<211> LENGTH: 665
<212> TYPE: PRT
<213> ORGANISM: Human immunodeficiency virus

<400> SEQUENCE: 73

Ile Ile His Thr Val Pro Pro Ser Gly Ala Asp Pro Gly Pro Lys Arg
1               5                   10                  15

Ala Glu Phe Lys Gly Leu Arg Arg Gln Gln Lys Gln Gly Ile Ile Leu
            20                  25                  30

Leu Thr Met Lys Thr Ile Ile Ala Leu Ser Tyr Ile Leu Cys Leu Val
        35                  40                  45

Leu Ala Gln Lys Leu Pro Gly Asn Asp Asn Asn Ser Glu Phe Ile Thr
    50                  55                  60

Ser Gly Phe Leu Gly Pro Leu Leu Val Leu Gln Ala Gly Phe Phe Leu
65                  70                  75                  80

Leu Thr Arg Ile Leu Thr Ile Pro Gln Ser Leu Asp Ser Trp Trp Thr
                85                  90                  95

Ser Leu Asn Phe Leu Gly Gly Ser Pro Val Cys Leu Gly Gln Asn Ser
            100                 105                 110

Gln Ser Pro Thr Ser Asn His Ser Pro Thr Ser Cys Pro Pro Ile Cys
        115                 120                 125

Pro Gly Tyr Arg Trp Met Cys Leu Arg Arg Phe Ile Ile Phe Leu Phe
    130                 135                 140

Ile Leu Leu Leu Cys Leu Ile Phe Leu Leu Val Leu Leu Asp Tyr Gln
145                 150                 155                 160

Gly Met Leu Pro Val Cys Pro Leu Ile Pro Gly Ser Thr Thr Thr Ser
                165                 170                 175

Thr Gly Pro Cys Lys Thr Cys Thr Thr Pro Ala Gln Gly Asn Ser Lys
            180                 185                 190

Phe Pro Ser Cys Cys Cys Thr Lys Pro Thr Asp Gly Asn Cys Thr Cys
        195                 200                 205

Ile Pro Ile Pro Ser Ser Trp Ala Phe Ala Lys Tyr Leu Trp Glu Trp
    210                 215                 220

Ala Ser Val Arg Phe Ser Trp Leu Ser Leu Leu Val Pro Phe Val Gln
225                 230                 235                 240

Trp Phe Val Gly Leu Ser Pro Thr Val Trp Leu Ser Ala Ile Trp Met
                245                 250                 255

Met Trp Tyr Trp Gly Pro Ser Leu Tyr Ser Ile Val Ser Pro Phe Ile
            260                 265                 270

Pro Leu Leu Pro Ile Phe Phe Cys Leu Trp Val Tyr Ile Gly Val Pro
```

```
            275                 280                 285
Val Trp Lys Glu Ala Thr Thr Thr Leu Phe Cys Ala Ser Asp Ala Lys
            290                 295                 300
Ala Tyr Asp Thr Glu Val His Asn Val Trp Ala Thr His Ala Cys Val
305                 310                 315                 320
Pro Thr Asp Pro Asn Pro Gln Glu Val Val Leu Val Asn Val Thr Glu
                325                 330                 335
Asn Phe Asn Met Trp Lys Asn Asp Met Val Glu Gln Met His Glu Asp
                340                 345                 350
Ile Ile Ser Leu Trp Asp Gln Ser Leu Lys Pro Cys Val Lys Leu Thr
            355                 360                 365
Pro Leu Ser Val Gln Ala Cys Pro Lys Val Ser Phe Glu Pro Ile Pro
        370                 375                 380
Ile His Tyr Cys Ala Pro Ala Gly Phe Ala Ile Leu Lys Cys Asn Asn
385                 390                 395                 400
Lys Thr Phe Asn Gly Thr Gly Pro Cys Thr Asn Val Ser Thr Val Gln
                405                 410                 415
Cys Thr His Gly Ile Arg Pro Val Val Ser Thr Gln Leu Leu Leu Asn
                420                 425                 430
Gly Ser Leu Ala Glu Glu Val Val Ile Arg Ser Val Asn Phe Thr
            435                 440                 445
Asp Asn Ala Lys Thr Ile Ile Val Gln Leu Asn Thr Ser Val Glu Ile
450                 455                 460
Asn Cys Thr Arg Pro Ser Val Asn Phe Thr Asp Asn Ala Lys Thr Ile
465                 470                 475                 480
Ile Val Gln Leu Asn Thr Ser Val Glu Ile Asn Cys Thr Arg Pro Met
                485                 490                 495
Arg Gln Ala His Cys Asn Ile Ser Arg Ala Lys Trp Asn Asn Thr Leu
                500                 505                 510
Lys Gln Ile Ala Ser Lys Leu Arg Glu Gln Phe Gly Asn Asn Lys Thr
            515                 520                 525
Ile Ile Phe Lys Gln Ser Ser Gly Gly Asp Pro Glu Ile Val Thr His
        530                 535                 540
Ser Phe Asn Cys Gly Gly Glu Phe Phe Tyr Cys Asn Ser Thr Gln Leu
545                 550                 555                 560
Phe Asn Ser Thr Trp Phe Asn Ser Thr Trp Ser Thr Glu Gly Ser Asn
                565                 570                 575
Asn Thr Glu Gly Ser Asp Thr Ile Thr Leu Pro Cys Arg Ile Lys Gln
                580                 585                 590
Ser Ile Ala Met Tyr Ala Pro Pro Ile Ser Gly Gln Ile Arg Cys Ser
            595                 600                 605
Ser Asn Ile Thr Gly Leu Leu Leu Thr Arg Asp Gly Gly Asn Ser Asn
        610                 615                 620
Asn Glu Ser Glu Ile Phe Arg Pro Gly Gly Gly Asp Met Arg Asp Asn
625                 630                 635                 640
Trp Arg Ser Glu Leu Tyr Lys Tyr Lys Val Val Lys Ile Glu Pro Leu
                645                 650                 655
Gly Val Ala Pro Thr Lys Ala Lys Arg
                660                 665

<210> SEQ ID NO 74
<211> LENGTH: 2000
<212> TYPE: DNA
<213> ORGANISM: Human immunodeficiency virus
```

<400> SEQUENCE: 74

```
ggattattca taccgtccca ccatcgggcg cggatcccgg tccgaagcgc gcggaattca      60
aaggcctacg tcgacagcaa aagcagggga taattctatt aaccatgaag actatcattg     120
ctttgagcta cattttatgt ctggttctcg ctcaaaaact tcccggaaat gacaacaaca     180
gcgaattcat cacctccggc ttcctgggcc cctgctggt gctgcaggcc ggcttcttcc      240
tgctgacccg catcctgacc atccccagt ccctggactc ctggtggacc tccctgaact     300
tcctgggcgg ctccccgtg tgcctgggcc agaactccca gtcccccacc tccaaccact     360
ccccacctc ctgccccccc atctgccccg gctaccgctg gatgtgcctg cgccgcttca     420
tcatcttcct gttcatcctg ctgctgtgcc tgatcttcct gctggtgctg ctggactacc     480
agggcatgct gcccgtgtgc ccctgatcc ccggctccac caccacctcc accgccccct     540
gcaagacctg caccaccccc gcccagggca actccaagtt ccctcctgc tgctgcacca     600
agcccaccga cggcaactgc acctgcatcc ccatcccctc ctcctgggcc ttcgccaagt     660
acctgtggga gtgggcctcc gtgcgcttct cctggctgtc cctgctggtg cccttcgtgc     720
agtggttcgt gggcctgtcc cccaccgtgt ggctgtccgc catctggatg atgtggtact     780
ggggcccctc cctgtactcc atcgtgtccc ccttcatccc cctgctgccc atcttcttct     840
gcctgtgggg gtacatcggg gtacctgtgt ggaaggaagc aaccaccact ctattttgtg     900
catcagatgc taaagcatat gatacagagg tacataatgt ttgggccaca catgcctgtg     960
tacccacaga ccccaaccca caagaagtag tattggtaaa tgtgacagaa aattttaaca    1020
tgtggaaaaa tgacatggta gaacagatgc atgaggatat aatcagttta tgggatcaaa    1080
gcctaaagcc atgtgtaaaa ttaaccccac tctcggtcca ggcctgtcca aggtatcct     1140
ttgagccaat tcccatacat tattgtgccc cggctggttt tgcgattcta aaatgtaata    1200
ataagacgtt caatggaaca ggaccatgta caaatgtcag cacagtacaa tgtacacatg    1260
gaattaggcc agtagtatca actcaactgc tgttaaatgg cagtctagca gaagaagagg    1320
tagtaattag atctgtcaat ttcacggaca atgctaaaac cataatagta cagctgaaca    1380
catctgtaga aattaattgt acaagaccct ctgtcaattt cacggacaat gctaaaacca    1440
taatagtaca gctgaacaca tctgtagaaa ttaattgtac aagacccatg agacaagcac    1500
attgtaacat tagtagagca aaatggaata acactttaaa acagatagct agcaaattaa    1560
gagaacaatt tggaaataat aaaacaataa tctttaagca atcctcagga ggggacccag    1620
aaattgtaac gcacagtttt aattgtggag gggaattttt ctactgtaat tcaacacaac    1680
tgtttaatag tacttggttt aatagtactt ggagtactga agggtcaaat aacactgaag    1740
gaagtgacac aatcaccctc ccatgcagaa taaaacaatc gatagcaatg tatgcccctc    1800
ccatcagtgg acaaattaga tgttcatcaa atattacagg gctgctatta acaagagatg    1860
gtggtaatag caacaatgag tccgagatct tcagacctgg aggaggagat atgagggaca    1920
attggagaag tgaattatat aaatataaag tagtaaaaat tgaaccatta ggagtagcac    1980
ccaccaaggc aaagagataa                                                2000
```

<210> SEQ ID NO 75
<211> LENGTH: 50
<212> TYPE: DNA
<213> ORGANISM: Artificial sequence
<220> FEATURE:
<223> OTHER INFORMATION: Synthetic neucleic acid primer.

-continued

<400> SEQUENCE: 75
cggcggccgc accggtcgcc accatggccc agtccaagca cggcctgacc         50

<210> SEQ ID NO 76
<211> LENGTH: 47
<212> TYPE: DNA
<213> ORGANISM: Artificial sequence
<220> FEATURE:
<223> OTHER INFORMATION: Synthetic neucleic acid primer.

<400> SEQUENCE: 76
tggcggccgc tctagatccg gtggatcccg ggcccgcggt accgtcg          47

<210> SEQ ID NO 77
<211> LENGTH: 366
<212> TYPE: PRT
<213> ORGANISM: Artificial sequence
<220> FEATURE:
<223> OTHER INFORMATION: Recombinant antigenic insert peptide construct.

<400> SEQUENCE: 77

Pro Gln Gly Ala Arg Met Ala Ser Thr Thr Pro Ile Thr Met Glu Asp
1               5                   10                  15

Leu Gln Lys Ala Leu Glu Ala Gln Ser Arg Ala Leu Arg Ala Asp Leu
            20                  25                  30

Ala Ala Gly Ala Ser Gln Ser Arg Arg Pro Arg Pro Arg Gln Arg
        35                  40                  45

Asp Ser Ser Thr Ser Gly Asp Asp Ser Arg Asp Ser Gly Gly Pro
    50                  55                  60

Arg Arg Arg Gly Asn Arg Gly Arg Gly Gln Arg Arg Asp Trp Ser
65                  70                  75                  80

Arg Ala Pro Pro Pro Glu Glu Arg Gln Glu Ser Arg Ser Gln Thr
            85                  90                  95

Pro Ala Pro Lys Pro Ser Arg Ala Pro Pro Gln Gln Pro Gln Pro Pro
            100                 105                 110

Arg Met Gln Thr Gly Arg Gly Gly Ser Ala Pro Arg Pro Glu Leu Gly
            115                 120                 125

Pro Pro Thr Asn Pro Phe Gln Ala Ala Val Ala Arg Gly Leu Arg Pro
        130                 135                 140

Pro Leu His Asp Pro Asp Thr Glu Ala Pro Thr Glu Ala Cys Val Thr
145                 150                 155                 160

Ser Trp Leu Trp Ser Glu Gly Glu Gly Ala Val Phe Tyr Arg Val Asp
            165                 170                 175

Leu His Phe Thr Asn Leu Gly Thr Pro Pro Leu Asp Glu Asp Gly Arg
            180                 185                 190

Trp Asp Pro Ala Leu Met Tyr Asn Pro Cys Gly Pro Glu Pro Pro Ala
            195                 200                 205

His Val Val Arg Ala Tyr Asn Gln Pro Ala Gly Asp Val Arg Gly Val
        210                 215                 220

Trp Gly Lys Gly Glu Arg Thr Tyr Ala Glu Gln Asp Phe Arg Val Gly
225                 230                 235                 240

Gly Thr Arg Trp His Arg Leu Leu Arg Met Pro Val Arg Gly Leu Asp
            245                 250                 255

Gly Asp Ser Ala Pro Leu Pro Pro Tyr Thr Thr Glu Arg Ile Glu Thr
            260                 265                 270

```
Arg Ser Ala Arg His Pro Trp Arg Ile Arg Phe Gly Ala Pro Gln Ala
        275                 280                 285

Phe Leu Ala Gly Leu Leu Leu Ala Thr Val Ala Val Gly Thr Ala Arg
        290                 295                 300

Ala Gly Leu Gln Pro Arg Ala Asp Met Ala Ala Pro Pro Thr Leu Pro
305                 310                 315                 320

Arg Ser Ala Gln Glu Lys Asn Glu Lys Glu Leu Leu Glu Leu Asp Lys
                325                 330                 335

Trp Ala Ser Leu Trp Asn Trp Phe Asp Ile Thr Asn Trp Leu Trp Tyr
        340                 345                 350

Ile Arg Leu Phe Ile Asp Ala Ser Thr Arg Ser Ala Arg His
        355                 360                 365

<210> SEQ ID NO 78
<211> LENGTH: 367
<212> TYPE: PRT
<213> ORGANISM: Artificial sequence
<220> FEATURE:
<223> OTHER INFORMATION: Recombinant antigenic insert peptide construct.

<400> SEQUENCE: 78

Asp Ser Ala Pro Leu Pro Pro His Thr Thr Glu Arg Ile Glu Thr Arg
1               5                   10                  15

Ser Ala Arg His Pro Trp Arg Ile Arg Phe Gly Ala Pro Gln Ala Phe
                20                  25                  30

Leu Ala Gly Leu Leu Leu Ala Thr Val Ala Val Gly Thr Ala Arg Ala
            35                  40                  45

Gly Pro Arg Ser Ala Gln Glu Lys Asn Glu Lys Glu Leu Leu Glu Leu
        50                  55                  60

Asp Lys Trp Ala Ser Leu Trp Asn Trp Phe Asp Ile Thr Asn Trp Leu
65                  70                  75                  80

Trp Tyr Ile Arg Leu Phe Ile Asp Ala Ser Ala Gly Leu Gln Pro Arg
                85                  90                  95

Ala Asp Met Ala Ala Pro Pro Thr Leu Pro Gln Pro Cys Ala His
                100                 105                 110

Gly Gln His Tyr Gly His His His Gln Leu Pro Phe Leu Gly His
            115                 120                 125

Asp Gly His His Gly Gly Thr Leu Arg Val Gly Gln His Tyr Arg Asn
        130                 135                 140

Ala Ser Asp Val Leu Pro Gly His Trp Leu Gln Gly Trp Gly Cys
145                 150                 155                 160

Tyr Asn Leu Ser Asp Trp His Gln Gly Thr His Val Cys His Thr Lys
                165                 170                 175

His Met Asp Phe Trp Cys Val Glu His Asp Arg Pro Pro Ala Thr
            180                 185                 190

Pro Thr Pro Leu Thr Thr Ala Ala Asn Ser Thr Thr Ala Ala Thr Pro
        195                 200                 205

Ala Thr Ala Pro Ala Pro Cys His Ala Gly Leu Asn Asp Ser Cys Gly
        210                 215                 220

Gly Phe Leu Ser Gly Cys Gly Pro Met Arg Leu Arg His Gly Ala Asp
225                 230                 235                 240
```

Thr Arg Cys Gly Arg Leu Ile Cys Gly Leu Ser Thr Thr Ala Gln Tyr
            245                 250                 255

Pro Pro Thr Arg Phe Gly Cys Ala Met Arg Trp Gly Leu Pro Pro Trp
            260                 265                 270

Glu Leu Val Val Leu Thr Ala Arg Pro Glu Asp Gly Trp Thr Cys Arg
            275                 280                 285

Gly Val Pro Ala His Pro Gly Ala Arg Cys Pro Glu Leu Val Ser Pro
            290                 295                 300

Met Gly Arg Ala Thr Cys Ser Pro Ala Ser Ala Leu Trp Leu Ala Thr
305                 310                 315                 320

Ala Asn Ala Leu Ser Leu Asp His Ala Leu Ala Ala Phe Val Leu Leu
                325                 330                 335

Val Pro Trp Val Leu Ile Phe Met Val Cys Arg Arg Ala Cys Arg Arg
            340                 345                 350

Arg Gly Ala Ala Ala Ala Leu Thr Ala Val Val Leu Gln Gly Tyr
            355                 360                 365

<210> SEQ ID NO 79
<211> LENGTH: 367
<212> TYPE: PRT
<213> ORGANISM: Artificial sequence
<220> FEATURE:
<223> OTHER INFORMATION: Recombinant antigenic insert peptide construct.

<400> SEQUENCE: 79

Ala Gly Leu Leu Leu Ala Thr Val Ala Val Gly Thr Ala Arg Ala Gly
1               5                   10                  15

Leu Gln Pro Arg Ala Asp Met Ala Ala Pro Thr Leu Pro Gln Pro
            20                  25                  30

Pro Cys Ala His Gly Gln His Tyr Gly His His His Gln Leu Pro
            35                  40                  45

Phe Leu Gly His Asp Gly His His Gly Gly Thr Leu Arg Val Gly Gln
            50                  55                  60

His Tyr Arg Asn Ala Ser Asp Val Leu Pro Gly His Trp Leu Gln Gly
65                  70                  75                  80

Gly Trp Gly Cys Tyr Asn Leu Ser Asp Trp His Gln Gly Thr His Val
                85                  90                  95

Cys His Thr Lys His Met Asp Phe Trp Cys Val Glu His Asp Arg Pro
            100                 105                 110

Pro Pro Ala Thr Pro Thr Pro Leu Thr Thr Ala Ala Asn Ser Thr Thr
            115                 120                 125

Ala Ala Thr Pro Ala Thr Ala Pro Ala Pro Cys His Ala Gly Leu Asn
            130                 135                 140

Asp Ser Cys Gly Gly Phe Leu Ser Gly Cys Gly Pro Met Arg Leu Arg
145                 150                 155                 160

His Gly Ala Asp Thr Arg Cys Gly Arg Leu Ile Cys Gly Leu Ser Thr
                165                 170                 175

Thr Ala Gln Tyr Pro Pro Thr Arg Phe Gly Cys Ala Met Arg Trp Gly
            180                 185                 190

Leu Pro Pro Trp Glu Leu Val Val Leu Thr Ala Arg Pro Glu Asp Gly
            195                 200                 205

```
Trp Thr Cys Arg Gly Val Pro Ala His Pro Gly Ala Arg Cys Pro Glu
    210                 215                 220

Leu Val Ser Pro Met Gly Arg Ala Thr Cys Ser Pro Ala Ser Ala Leu
225                 230                 235                 240

Trp Leu Ala Thr Ala Asn Ala Leu Ser Leu Asp His Ala Leu Ala Ala
                245                 250                 255

Phe Val Leu Val Pro Trp Val Leu Ile Phe Met Val Cys Arg Arg
                260                 265                 270

Ala Cys Arg Arg Arg Gly Ala Ala Ala Leu Thr Ala Val Val Leu
                275                 280                 285

Gln Gly Pro Arg Ser Ala Gln Glu Lys Asn Glu Lys Glu Leu Leu Glu
    290                 295                 300

Leu Asp Lys Trp Ala Ser Leu Trp Asn Trp Phe Asp Ile Thr Asn Trp
305                 310                 315                 320

Leu Trp Tyr Ile Arg Leu Phe Ile Asp Ala Ser Arg Arg Gly Ala
                325                 330                 335

Ala Ala Ala Leu Thr Ala Val Val Leu Gln Gly Tyr Asn Pro Pro Ala
                340                 345                 350

Tyr Gly Glu Glu Ala Phe Thr Tyr Leu Cys Thr Ala Pro Gly Cys
            355                 360                 365

<210> SEQ ID NO 80
<211> LENGTH: 566
<212> TYPE: PRT
<213> ORGANISM: Artificial sequence
<220> FEATURE:
<223> OTHER INFORMATION: Recombinant antigenic insert peptide construct.

<400> SEQUENCE: 80

Met Val Cys Arg Arg Ala Cys Arg Arg Gly Ala Ala Ala Leu
1               5                   10                  15

Thr Ala Val Val Leu Gln Gly Tyr Asn Pro Pro Ala Tyr Gly Glu Ala
                20                  25                  30

Pro Arg Ser Ala Gln Glu Lys Asn Glu Lys Glu Leu Leu Glu Leu Asp
                35                  40                  45

Lys Trp Ala Ser Leu Trp Asn Trp Phe Asp Ile Thr Asn Trp Leu Trp
    50                  55                  60

Tyr Ile Arg Leu Phe Ile Asp Ala Ser Leu Gln Gly Tyr Asn Pro Pro
65                  70                  75                  80

Ala Tyr Gly Glu Glu Ala Phe Thr Tyr Leu Cys Thr Ala Pro Gly Cys
                85                  90                  95

Ala Thr Gln Ala Pro Val Pro Val Arg Leu Ala Gly Val Arg Phe Glu
                100                 105                 110

Ser Lys Ile Val Asp Gly Gly Cys Phe Ala Pro Trp Asp Leu Glu Ala
                115                 120                 125

Thr Gly Ala Cys Ile Cys Glu Ile Pro Thr Asp Val Ser Cys Glu Gly
                130                 135                 140

Leu Gly Ala Trp Val Pro Ala Pro Cys Ala Arg Ile Trp Asn Gly
145                 150                 155                 160

Thr Gln Arg Ala Cys Thr Phe Trp Ala Val Asn Ala Tyr Ser Ser Gly
                165                 170                 175
```

```
Gly Tyr Ala Gln Leu Ala Ser Tyr Phe Asn Pro Gly Ser Tyr Tyr
            180                 185                 190

Lys Gln Tyr His Pro Thr Ala Cys Glu Val Glu Pro Ala Phe Gly His
            195                 200                 205

Ser Asp Ala Ala Cys Trp Gly Phe Pro Thr Asp Thr Val Met Ser Val
            210                 215                 220

Phe Ala Leu Ala Ser Tyr Val Gln His Pro His Lys Thr Val Arg Val
225                 230                 235                 240

Lys Phe His Thr Glu Thr Arg Thr Val Trp Gln Leu Ser Val Ala Gly
            245                 250                 255

Val Ser Cys Asn Val Thr Thr Glu His Pro Phe Cys Asn Thr Pro His
            260                 265                 270

Gly Gln Leu Glu Val Gln Val Pro Pro Asp Pro Gly Asp Leu Val Glu
            275                 280                 285

Tyr Ile Met Asn Tyr Thr Gly Asn Gln Gln Ser Arg Trp Gly Leu Gly
            290                 295                 300

Ser Pro Asn Cys His Gly Pro Asp Trp Ala Ser Pro Val Cys Gln Arg
305                 310                 315                 320

His Ser Pro Asp Cys Ser Arg Leu Val Gly Ala Thr Pro Glu Arg Pro
            325                 330                 335

Arg Leu Arg Leu Val Asp Ala Asp Pro Leu Leu Arg Thr Ala Pro
            340                 345                 350

Gly Pro Gly Glu Val Trp Val Thr Pro Val Ile Gly Ser Gln Ala Arg
            355                 360                 365

Lys Cys Gly Leu His Ile Arg Ala Gly Pro Tyr Gly His Ala Thr Val
370                 375                 380

Glu Met Pro Glu Trp Ile His Ala His Thr Thr Ser Asp Pro Trp His
385                 390                 395                 400

Pro Pro Gly Pro Leu Gly Leu Lys Phe Lys Thr Val Arg Pro Val Ala
            405                 410                 415

Leu Pro Arg Thr Leu Ala Pro Pro Arg Asn Val Arg Val Thr Gly Cys
            420                 425                 430

Tyr Gln Cys Gly Thr Pro Ala Leu Val Glu Gly Leu Ala Pro Gly Gly
            435                 440                 445

Gly Asn Cys His Leu Thr Val Asn Gly Glu Asp Leu Gly Ala Val Pro
450                 455                 460

Pro Gly Lys Phe Val Thr Ala Ala Leu Leu Asn Thr Pro Pro Tyr
465                 470                 475                 480

Gln Val Ser Cys Gly Gly Glu Ser Asp Arg Ala Thr Ala Arg Val Ile
            485                 490                 495

Asp Pro Ala Ala Gln Ser Phe Thr Gly Val Val Tyr Gly Thr His Thr
            500                 505                 510

Thr Ala Val Ser Glu Thr Arg Gln Thr Trp Ala Glu Trp Ala Ala Ala
            515                 520                 525

His Trp Trp Gln Leu Thr Leu Gly Ala Ile Cys Ala Leu Pro Leu Ala
            530                 535                 540

Gly Leu Leu Ala Cys Cys Ala Lys Cys Leu Tyr Tyr Leu Arg Gly Ala
545                 550                 555                 560
```

```
Ile Ala Pro Arg Trp Ala
            565

<210> SEQ ID NO 81
<211> LENGTH: 34
<212> TYPE: PRT
<213> ORGANISM: Artificial sequence
<220> FEATURE:
<223> OTHER INFORMATION: Recombinant antigenic insert peptide.

<400> SEQUENCE: 81

Gln Glu Lys Asn Glu Lys Glu Leu Leu Glu Leu Asp Lys Trp Ala Ser
1               5                   10                  15

Leu Trp Asn Trp Phe Asp Ile Thr Asn Trp Leu Trp Tyr Ile Arg Leu
            20                  25                  30

Phe Ile

<210> SEQ ID NO 82
<211> LENGTH: 39
<212> TYPE: PRT
<213> ORGANISM: Artificial sequence
<220> FEATURE:
<223> OTHER INFORMATION: Recombinant antigenic insert peptide.

<400> SEQUENCE: 82

Arg Glu Gly Ser Gln Lys Ile Leu Ser Val Leu Ala Pro Leu Val Pro
1               5                   10                  15

Thr Gly Ser Glu Asn Leu Lys Ser Leu Tyr Asn Thr Val Ser Val Ile
            20                  25                  30

Trp Ser Ile His Ala Glu Asp
        35

<210> SEQ ID NO 83
<211> LENGTH: 38
<212> TYPE: PRT
<213> ORGANISM: Artificial sequence
<220> FEATURE:
<223> OTHER INFORMATION: Recombinant antigenic insert peptide.

<400> SEQUENCE: 83

Phe Gln Ala Leu Ser Glu Gly Cys Thr Pro Tyr Asp Ile Asn Gln Met
1               5                   10                  15

Leu Asn Cys Val Gly Asp His Gln Ala Ala Met Gln Ile Ile Arg Asp
            20                  25                  30

Ile Ile Asn Glu Glu Ala
        35

<210> SEQ ID NO 84
<211> LENGTH: 65
<212> TYPE: PRT
<213> ORGANISM: Artificial sequence
<220> FEATURE:
<223> OTHER INFORMATION: Recombinant antigenic insert peptide.

<400> SEQUENCE: 84

Leu Pro Leu Ser Pro Arg Thr Leu Asn Ala Trp Val Lys Leu Ile Glu
1               5                   10                  15
```

```
Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala
65

<210> SEQ ID NO 85
<211> LENGTH: 81
<212> TYPE: PRT
<213> ORGANISM: Artificial sequence
<220> FEATURE:
<223> OTHER INFORMATION: Recombinant antigenic insert peptide.

<400> SEQUENCE: 85

Leu Pro Leu Ser Pro Arg Thr Leu Asn Ala Trp Val Lys Leu Ile Glu
1               5                   10                  15

Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala Thr Arg Ser Gln Lys Ile Leu Ser Val Leu Ala Pro Leu Val Pro
65                  70                  75                  80

Thr

<210> SEQ ID NO 86
<211> LENGTH: 79
<212> TYPE: PRT
<213> ORGANISM: Artificial sequence
<220> FEATURE:
<223> OTHER INFORMATION: Recombinant antigenic insert peptide.

<400> SEQUENCE: 86

Leu Pro Leu Ser Pro Arg Thr Leu Asn Ala Trp Val Lys Leu Ile Glu
1               5                   10                  15

Glu Lys Lys Phe Gly Ala Glu Val Val Pro Gly Phe Gln Ala Leu Ser
                20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala Thr Arg Thr Gly Ser Glu Asn Leu Lys Ser Leu Tyr Asn Thr
65                  70                  75

<210> SEQ ID NO 87
<211> LENGTH: 87
<212> TYPE: PRT
<213> ORGANISM: Artificial sequence
<220> FEATURE:
<223> OTHER INFORMATION: Recombinant antigenic insert peptide.

<400> SEQUENCE: 87

Leu Pro Leu Ser Pro Arg Thr Leu Asn Ala Trp Val Lys Leu Ile Glu
1               5                   10                  15

Glu Lys Lys Phe Gly Ala Glu Val Val Pro Gly Phe Gln Ala Leu Ser
```

```
                    20                  25                  30

Glu Gly Cys Thr Pro Tyr Asp Ile Asn Gln Met Leu Asn Cys Val Gly
            35                  40                  45

Asp His Gln Ala Ala Met Gln Ile Ile Arg Asp Ile Ile Asn Glu Glu
        50                  55                  60

Ala Thr Arg His Thr Glu Ala Lys Gln Ile Val Gln Arg His Leu
65                  70                  75                  80

Val Val Glu Thr Gly Thr Thr
                85

<210> SEQ ID NO 88
<211> LENGTH: 80
<212> TYPE: PRT
<213> ORGANISM: Artificial sequence
<220> FEATURE:
<223> OTHER INFORMATION: Recombinant antigenic insert peptide.

<400> SEQUENCE: 88

Val Pro Thr Gly Ser Glu Asn Leu Lys Ser Leu Tyr Asn Thr Val Thr
1               5                   10                  15

Arg Val Lys His Thr Glu Glu Ala Lys Gln Ile Val Gln Arg His Leu
                20                  25                  30

Val Val Glu Thr Gly Thr Thr Ser Asp Ala Phe Gln Ala Leu Ser Glu
            35                  40                  45

Gly Cys Thr Pro Tyr Asp Ile Asn Gln Met Leu Asn Cys Val Gly Asp
        50                  55                  60

His Gln Ala Ala Met Gln Ile Ile Arg Asp Ile Ile Asn Glu Glu Ala
65                  70                  75                  80

<210> SEQ ID NO 89
<211> LENGTH: 19
<212> TYPE: PRT
<213> ORGANISM: Human immunodeficiency virus

<400> SEQUENCE: 89

Pro Ser Trp Asn Trp Phe Asp Ile Thr Asn Trp Leu Trp Tyr Ile Arg
1               5                   10                  15

Leu Asp Ala

<210> SEQ ID NO 90
<211> LENGTH: 109
<212> TYPE: PRT
<213> ORGANISM: Artificial sequence
<220> FEATURE:
<223> OTHER INFORMATION: Recombinant antigenic insert peptide.

<400> SEQUENCE: 90

Leu Asp Arg Phe Gly Leu Ala Glu Ser Leu Leu Glu Asn Lys Glu Gly
1               5                   10                  15

Ser Gln Lys Ile Leu Ser Val Leu Ala Pro Leu Val Pro Thr Gly Ser
                20                  25                  30

Glu Asn Leu Lys Ser Leu Tyr Asn Thr Val Thr Arg Val Lys His Thr
            35                  40                  45

Glu Glu Ala Lys Gln Ile Val Gln Arg His Leu Val Val Glu Thr Gly
        50                  55                  60

Thr Thr Glu Thr Ser Asp Ala Phe Gln Ala Leu Ser Glu Gly Cys Thr
65                  70                  75                  80

Pro Tyr Asp Ile Asn Gln Met Leu Asn Cys Val Gly Asp His Gln Ala
                85                  90                  95
```

```
Ala Met Gln Ile Ile Arg Asp Ile Ile Asn Glu Glu Ala
            100                 105

<210> SEQ ID NO 91
<211> LENGTH: 134
<212> TYPE: PRT
<213> ORGANISM: Artificial sequence
<220> FEATURE:
<223> OTHER INFORMATION: Recombinant antigenic insert peptide.

<400> SEQUENCE: 91

Leu Asp Arg Phe Gly Leu Ala Glu Ser Leu Leu Glu Asn Lys Glu Gly
1               5                   10                  15

Ser Gln Lys Ile Leu Ser Val Leu Ala Pro Leu Val Pro Thr Gly Ser
            20                  25                  30

Glu Asn Leu Lys Ser Leu Tyr Asn Thr Val Thr Arg Val Lys His Thr
        35                  40                  45

Glu Glu Ala Lys Gln Ile Val Gln Arg His Leu Val Val Glu Thr Gly
    50                  55                  60

Thr Thr Glu Thr Arg Leu Pro Leu Ser Pro Arg Thr Leu Asn Ala Trp
65                  70                  75                  80

Val Lys Leu Ile Glu Glu Lys Lys Phe Gly Ala Glu Val Val Pro Gly
                85                  90                  95

Phe Gln Ala Leu Ser Glu Gly Cys Thr Pro Tyr Asp Ile Asn Gln Met
            100                 105                 110

Leu Asn Cys Val Gly Asp His Gln Ala Ala Met Gln Ile Ile Arg Asp
        115                 120                 125

Ile Ile Asn Glu Glu Ala
    130

<210> SEQ ID NO 92
<211> LENGTH: 9
<212> TYPE: PRT
<213> ORGANISM: Human immunodeficiency virus

<400> SEQUENCE: 92

Cys Thr Pro Tyr Asp Ile Asn Gln Met
1               5

<210> SEQ ID NO 93
<211> LENGTH: 9
<212> TYPE: PRT
<213> ORGANISM: Human immunodeficiency virus

<400> SEQUENCE: 93

Gly Ser Glu Asn Leu Lys Ser Leu Tyr
1               5

<210> SEQ ID NO 94
<211> LENGTH: 11
<212> TYPE: PRT
<213> ORGANISM: Human immunodeficiency virus

<400> SEQUENCE: 94

Lys Ile Leu Ser Val Leu Ala Pro Leu Val Pro
1               5                   10

<210> SEQ ID NO 95
<211> LENGTH: 16
<212> TYPE: PRT
<213> ORGANISM: Human immunodeficiency virus
```

```
<400> SEQUENCE: 95

Thr Glu Glu Ala Lys Gln Ile Val Gln Arg His Leu Val Val Glu Thr
1               5                   10                  15

<210> SEQ ID NO 96
<211> LENGTH: 11
<212> TYPE: PRT
<213> ORGANISM: Human immunodeficiency virus

<400> SEQUENCE: 96

Met Gln Ile Ile Arg Asp Ile Ile Asn Glu Glu
1               5                   10

<210> SEQ ID NO 97
<211> LENGTH: 9
<212> TYPE: PRT
<213> ORGANISM: Human immunodeficiency virus

<400> SEQUENCE: 97

Thr Arg Ala Asn Ser Pro Thr Arg Arg
1               5

<210> SEQ ID NO 98
<211> LENGTH: 8
<212> TYPE: PRT
<213> ORGANISM: Human immunodeficiency virus

<400> SEQUENCE: 98

Asn Ser Pro Thr Arg Arg Glu Leu
1               5

<210> SEQ ID NO 99
<211> LENGTH: 9
<212> TYPE: PRT
<213> ORGANISM: Human immunodeficiency virus

<400> SEQUENCE: 99

Pro Thr Arg Arg Glu Leu Gln Val Trp
1               5

<210> SEQ ID NO 100
<211> LENGTH: 9
<212> TYPE: PRT
<213> ORGANISM: Human immunodeficiency virus

<400> SEQUENCE: 100

Pro Thr Ser Arg Glu Leu Gln Val Trp
1               5

<210> SEQ ID NO 101
<211> LENGTH: 9
<212> TYPE: PRT
<213> ORGANISM: Human immunodeficiency virus

<400> SEQUENCE: 101

Ala Gly Ala Glu Arg Gln Gly Thr Leu
1               5

<210> SEQ ID NO 102
<211> LENGTH: 9
<212> TYPE: PRT
<213> ORGANISM: Human immunodeficiency virus

<400> SEQUENCE: 102
```

```
Phe Ser Phe Pro Gln Ile Thr Leu Trp
1               5

<210> SEQ ID NO 103
<211> LENGTH: 171
<212> TYPE: PRT
<213> ORGANISM: Human immunodeficiency virus

<400> SEQUENCE: 103

Leu Asp Arg Phe Gly Leu Ala Glu Ser Leu Leu Glu Asn Lys Glu Gly
1               5                   10                  15

Cys Gln Lys Ile Leu Ser Val Leu Ala Pro Leu Val Pro Thr Gly Ser
                20                  25                  30

Glu Asn Leu Lys Ser Leu Tyr Asn Thr Val Cys Val Ile Trp Cys Ile
            35                  40                  45

His Ala Glu Glu Lys Val Lys His Thr Glu Glu Ala Lys Gln Ile Val
        50                  55                  60

Gln Arg His Leu Val Val Glu Thr Gly Thr Thr Glu Thr Met Pro Lys
65                  70                  75                  80

Thr Ser Arg Pro Thr Ala Pro Ser Ser Gly Arg Gly Gly Asn Tyr Pro
                85                  90                  95

Val Gln Gln Ile Gly Gly Asn Tyr Val His Leu Pro Leu Ser Pro Arg
                100                 105                 110

Thr Leu Asn Ala Trp Val Lys Leu Ile Glu Glu Lys Lys Phe Gly Ala
            115                 120                 125

Glu Val Val Pro Gly Phe Gln Ala Leu Ser Glu Gly Cys Thr Pro Tyr
        130                 135                 140

Asp Ile Asn Gln Met Leu Asn Cys Val Gly Asp His Gln Ala Ala Met
145                 150                 155                 160

Gln Ile Ile Arg Asp Ile Ile Asn Glu Glu Ala
                165                 170
```